(12) United States Patent
Capet et al.

(10) Patent No.: US 9,266,867 B2
(45) Date of Patent: Feb. 23, 2016

(54) PIPERIDINYL MONOCARBOXYLIC ACIDS AS S1P1 RECEPTOR AGONISTS

(75) Inventors: Marc Capet, Melesse (FR); Isabelle Berrebi-Bertrand, Pace (FR); Philippe Robert, Pace (FR); Jean-Charles Schwartz, Paris (FR); Jeanne-Marie Lecomte, Paris (FR); Rajamannar Thennati, Vadodara (IN); Ranjan Kumar Pal, Vadodara (IN); Biswajit Samanta, Vadodara (IN); Muthukumaran Natarajan Pillai, Vadodara (IN); Japan Nitinkumar Desai, Vadodara (IN); Dijixa Chandubhai Rana, Vadodara (IN); Kaushik Dhanjubhai Prajapati, Pin (IN); Sandeep Pankajbhai Pathak, Vadodara (IN); Bhavesh M. Panchal, Nagar (IN); Jayraj D. Aradhye, Vadodara (IN)

(73) Assignees: BIOPROJET, Paris (FR); SUN PHARMA ADVANCED RESEARCH COMPANY LTD, Mumbai (IN)

( * ) Notice: Subject to any disclaimer, the term of this patent is extended or adjusted under 35 U.S.C. 154(b) by 0 days.

(21) Appl. No.: 14/111,438

(22) PCT Filed: Apr. 10, 2012

(86) PCT No.: PCT/EP2012/056470
§ 371 (c)(1),
(2), (4) Date: Dec. 19, 2013

(87) PCT Pub. No.: WO2012/140020
PCT Pub. Date: Oct. 18, 2012

(65) Prior Publication Data
US 2014/0099316 A1    Apr. 10, 2014

(30) Foreign Application Priority Data
Apr. 12, 2011   (EP) .................................. 11305433

(51) Int. Cl.
*C07D 413/10*   (2006.01)
*C07D 271/06*   (2006.01)
*A61K 31/454*   (2006.01)
*A61K 45/06*   (2006.01)

(52) U.S. Cl.
CPC ............ *C07D 413/10* (2013.01); *A61K 31/454* (2013.01); *A61K 45/06* (2013.01); *C07D 271/06* (2013.01)

(58) Field of Classification Search
CPC ... A61K 45/06; A61K 31/454; C07D 413/10; C07D 271/06
USPC ............................ 514/326; 546/209; 548/131
See application file for complete search history.

(56) References Cited

U.S. PATENT DOCUMENTS

| 7,199,142 B2 | 4/2007 | Chen et al. |
| 2008/0280876 A1* | 11/2008 | Hobson et al. ............ 514/210.18 |
| 2010/0249187 A1 | 9/2010 | Capet et al. |

FOREIGN PATENT DOCUMENTS

| WO | WO2008152149 | * 12/2008 |
| WO | WO 2010/064707 | * 6/2010 |
| WO | WO 2011/035900 | * 3/2011 |
| WO | WO 2011/113578 | * 9/2011 |
| WO | WO 2012/109108 | * 8/2012 |

OTHER PUBLICATIONS

International Search Report for PCT/EP2012/056470 dated May 25, 2012.
Alperovich, et al., "New immunosuppresor strategies in the treatment of murine lupus nephritis", 2007, pp. 18-24, vol. 16, Lupus.
An, et al., "Suppression of Experimental Autoimmune Optic Neuritis by the Novel Agent Fingolimod", 2013, pp. 143-148, vol. 33, J. Neuro-Ophthalmol.
Ando, et al., "FTY720 exerts a survival advantage through the prevention of end-stage glomerular inflammation in lupus-prone BXSB mice", 2010, pp. 804-810, vol. 394, Biochemical and Biophysical Research Communications.
Bajwa, et al., "Activation of Sphingosine-1-Phosphate 1 Receptor in the Proximal Tuble Protects Against Ischemia-Reperfusion Injury", 2010, pp. 955-965, vol. 21, J. Am Soc Nephrol.
Balatoni, et al., "FTY720 sustains and restores neuronal function in the DA rat model of MOG-induced experimental autoimmune encephalomyelitis", 2007, pp. 307-316, vol. 74, Brain Research Bulletin.
Brinkmann, et al., "Pulmonary and vascular pharmacology of sphingosine 1-phosphate", 2006, pp. 244-250, vol. 6, Current Opinion in Pharmacology.
Brinkmann, et al, "Fingolimod (FTY720): discovery and development of an oral drug to treat multiple sclerosis", Nov. 2010, pp. 883-897, vol. 9, Nature Reviews.

(Continued)

*Primary Examiner* — Janet L Andres
*Assistant Examiner* — Daniel Carcanague
(74) *Attorney, Agent, or Firm* — B. Aaron Schulman, Esq.; Stites & Harbison, PLLC

(57) ABSTRACT

The present invention relates to novel compounds acting as agonists at S1P (sphingosine-1-phosphate) receptors, compositions containing these compounds, use of these compounds in medicine and their process of preparation.

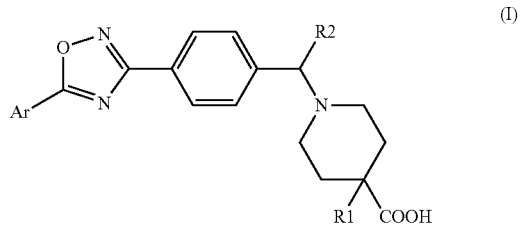

(I)

18 Claims, No Drawings

(56) References Cited

OTHER PUBLICATIONS

Choi, et al., "FTY720 (fingolimod) efficacy in an animal model of multiple sclerosis requires astrocyte sphingosine 1-phosphate receptor 1 ($S1P_1$) modulation", Jan. 11, 2011, pp. 751-756, vol. 108, No. 2, PNAS.

Copland, et al., "Therapeutic Dosing of Fingolimod (FTY720) Prevents Cell Infiltration, Rapidly Suppresses Ocular Inflammation, and Maintains the Blood-Ocular Barrier", Feb. 2012, pp. 673-681, vol. 180, No. 2, AJP.

Daniel, et al., "FTY720 ameliorates oxazolone colitis in mice by directly affecting T helper type 2 functions", 2007, pp. 3305-3316, vol. 44, Molecular Immunology.

Deguchi, et al., "The S1P receptor modulator FTY720 prevents the development of experimental colitis in mice", 2006, pp. 699-703, vol. 16, Oncology Reports.

Delbridge, et al., "FTY720 Reduces Extracellular Matrix Expansion Associated with Ischemia-Reperfusion Induced Injury", 2007, pp. 2992-2996, vol. 39, Transplantation Proceedings.

Diab, et al., "Stimulation of Sphingosine 1-Phosphate Signaling as an Alveolar Cell Survival Strategy in Emphysema", 2010, pp. 344-354, vol. 181, American Journal of Respiratory and Critical Care Medicine.

Egom, et al., "FTY720 prevents ischemia/reperfusion injury-associated arrhythmias in an ex vivo rat heart model via activation of Pak1/Akt signaling", 2010, pp. 406-414, vol. 48, Journal of Molecular and Cellular Cardiology.

Foster, et al., "Brain Penetration of the Oral Immunomodulatory Drug FTY720 and Its Phosphorylation in the Central Nervous System during Experimental Autoimmune Encephalomyelitis: Consequences for Mode of Action in Multiple Sclerosis", 2007, pp. 469-476, vol. 323, No. 2, The Journal of Pharmacology and Experimental Therapeutics.

Idzko, et al., "Local application of FTY720 to the lung abrogates experimental asthma by altering dendritic cell function", Nov. 2006, pp. 2935-2944, vol. 116, No. 11, The Journal of Clinical Investigation.

Graler, et al., "The role of sphingosine 1-phosphate in immunity and sepsis", 2012, pp. 90-100, vol. 1, No. 2, Am J Clin Exp Immunol.

Kluk, et al., "Sphingosine-1-phosphate receptor 1 in classical Hodgkin lymphoma: assessment of expression and role in cell migration", 2013, pp. 462-471, vol. 93, Laboratory Investigation.

Kohno, et al., a Novel Immunomodulator, FTY720, Prevents Spontaneous Dermatitis in NC/Nga Mice, 2004, pp. 1392-1396, vol. 27, No. 9, Biol. Pharm. Bull.

Hemmati, et al., "Neurorestorative effect of FTY720 in a rat model of Alzheimer's disease: Comparison with Memantine", 2013, pp. 415-421, Behavioural Brain Research.

Kaneko, et al., Sphingosine-1-phosphate receptor agonists suppress concanavalin A-induced hepatic injury in mice, 2006, pp. 85-92, vol. 345, Biochemical and Biophysical Research Communications.

Hofmann, et al., "Protective effects of sphingosine-1-phosphate receptor agonist treatment after myocardial ischaemia-reperfusion", 2009, pp. 285-293, vol. 83, Cardiovasular Research.

Ho, et al., "Effects of a novel immunomodulating agent, FTY720, on tumor growth and angiogenesis in hepatocellular carcinoma", 2005, pp. 1430-1438, vol. 4, Mol Cancer Ther.

Lamontagne, et al, "Antagonism of Sphingosine-1-Phosphate Receptors by FTY720 Inhibits Angiogenesis and Tumor Vascularization" 2006, pp. 221-231, vol. 66, Cancer Research.

Oldstone, et al., "Dissecting influenza virus pathogenesis uncovers a novel chemical approach to combat the infection", 2013, pp. 92-101, vol. 92, Virology.

Martini, et al., "S1P modulator FTY720 limits matrix expansion in acute anti-thy1 mesangioproliferative glomerulonephritis", 2007, pp. F1761-F1770, vol. 292, Am J Physiol Renl Physiol.

Matheu, et al., "Three Phases of CD8 T Cell Response in the Lung Following H1N1 Influenza Infection and Sphingosine Phosphate Agonist Therapy", Mar. 2013, pp. 1-15, vol. 8, No. 3, PLOS ONE.

Pan, et al., "A Monoselective Sphingosine-1-Phosphate Receptor-1 Agonist Prevents Allograft Rejection in a Stringent Rat Heart Transplantation Model", Nov. 2006, pp. 1227-1234, vol. 13, Chemistry & Biology.

Masuko, et al., "Sphingosine-1-phosphate modulates expression of vascular endothelial growth factor in human articular chondrocytes: a possible new role in arthritis", 2012, pp. 366-373, vol. 15, International Journal of Rheumatic Diseases.

Liu, et al., "FTY720 demonstrates promising preclinical activity for chronic lymphocytic leukemia and lymphoblastic leukemia/lymphoma", 2008, pp. 275-284, vol. 111, Blood.

Lien, et al., "$S1P_1$-selective agonist, SEW2871, ameliorates ischemic acute renal failure", 2006, pp. 1601-1608, vol. 69, Kidney International.

Peng, et al., "Protective Effects of Sphingosine 1-Phosphate in Murine Endotoxin-induced Inflammatory Lung Injury", 2004, pp. 1245-1251, vol. 169, American Journal of Respiratory and Critical Care Medicine.

Pewzner-Jung, et al., "Sphingoid long chain bases prevent lung infection by *Pseudomonas aeruginosa*", 2014, pp. 1205-1214, vol. 6, No. 9, EMBO Molecular Medicine.

Ogawa, et al., "A novel sphingosine-1-phosphate receptor agonist KRP-203 attenuates rat autoimmune myocarditis", 2007, pp. 621-628, vol. 361, Biochemical and Biophysical Research Communications.

Shah, et al., "Molecular profiling of LGL leukemia reveals role of sphingolipid signaling in survival of cytotoxic lymphocytes", 2008, pp. 770-781, vol. 112, Blood.

Schaper, et al., "Sphingosine-1-phosphate exhibits anti-proliferative and anti-inflammatory effects in mouse models of psoriasis", 2013, pp. 29-36, vol. 29, Journal of Dermatological Science.

Schmid, et al., "FTY720 Inhibits Tumor Growth and Angiogenesis", 2005, pp. 110-111, vol. 37, Transplantation Proceedings.

Shimizu, et al, "KRP-203, a Novel Synthetic Immunosuppressant, Prolongs Graft Survival and Attenuates Chronic Rejection in Rat Skin and Heart Allografts", 2005, pp. 222-229, vol. 111, Circulation.

Sawicka, et al., "Inhibition of Th1- and Th2-Mediated Airway Inflammation by the Sphingosine 1-Phosphate Receptor Agonist FTY720", 2003, pp. 6206-6214, vol. 171, J Immunol.

Sekiguchi, et al., "Role of Sphingosine 1-Phosphate in the Pathogenesis of Sjögren's Syndrome", 2008, pp. 1922-1928, The Journal of Immunology.

Song, et al., "A Novel Sphingosine 1-Phosphate Receptor Agonist, 2-Amino-2-propanediol Hydrochloride (KRP-203), Regulates Chronic Colitis in Inteleukin-10 Gene-Deficient Mice", 2008, vol. 324, No. 1, Journal of Pharmacology and Experimental Therapeutics.

Sui, et al., "The sphingosine-1-phosphate receptor agonist FTY720 prevents the development of anti-glomerular basement membrane glomerulonephritis", 2012, pp. 389-397, vol. 39, Mol Biol Rep.

Srinivasan, et al, "Sphingosine-1-Phosphate Reduces CD4+ T-Cell Activation in Type 1 Diabetes Through Regulation of Hypoxia-Inducible Factor Short Isoform I.1 and CD69", Feb. 2008, pp. 484-493, vol. 57, Diabetes.

Teijaro, et al., "Endothelial Cells are Central Orchestrators of Cytokine Amplification during Influenza Virus Infection", Sep. 16, 2011, pp. 980-991, vol. 146, Cell.

Sumi, et al, "Treatment with FTY720 during the induction or effector phase suppresses the development of experimental allergic conjunctivitis in mice", 2009, pp. 534-541, vol. 33, Cell Biology International.

Takasugi, et al., "FTY720/Fingolimod, a Sphingosine Analogue, Reduces Amyloid-β Production in Neurons", May 2013, pp. 1-8, vol. 8, No. 5, PLOS ONE.

Tsunemi, et al., "Effects of the novel immunosuppressant FTY720 in a murine rheumatoid arthritis model", 2010, pp. 197-204, vol. 136, Clinical Immunology.

Tolle, et al., "Sphingosine-l-phosphate and FTY720 as anti-atherosclerotic lipid compounds", 2007, pp. 171-179, vol. 37, European Journal of Clinical Investigation.

Yasui, et al., "FTY720 Induces Apoptosis in Multiple Myeloma Cells and Overcomes Drug Resistance", 2005, pp. 7478-7484, vol. 65, Cancer Res.

(56) References Cited

OTHER PUBLICATIONS

Wenderfer, et al., "Increased survival and reduced renal injury in MRL/lpr mice treated with a novel sphingosine-1-phosphate receptor agonist", 2008, pp. 1319-1326, vol. 74, Kidney International.

Walsh, et al, "Animal Model of Respiratory Syncytial Virus: CD8+ T Cells Cause a Cytokine Storm That is Chemically Tractable by Sphingosine-1-Phosphate 1 Receptor Agonist Therapy", 2014, pp. 6281-6293, vol. 88, No. 11.

Zhang, et al., "AUY954, a selective S1P1 modulator, prevents experimental autoimmune neuritis", 2009, pp. 59-65, vol. 216, Journal of Neuroimmunology.

Zhao, et al., "FTY720 Normalizes Hyperglycemia by Stimulating β-Cell in Vivo Regeneration in $db/db$ Mice through Regulation of Cyclin D3 and p57$^{KIP2}$", Feb. 17, 2012, pp. 5562-5573, vol. 287, No. 8, Journal of Biological Chemistry.

Wei, et al., "Fingolimod provides long-term protection in rodent models of cerebral ischemia", Jan. 2011, pp. 119-129, vol. 69, No. 1, Ann Neurol.

Karmouty-Quintana, et al., "Treatment with a sphingosine-1-phosphate analog inhibits airway remodeling following repeated allergen exposure", 2012, pp. L736-L745, vol. 302, Am J Physiol Lung Cell Mol Physiol.

Keul, et al., "The Sphingosine-1-Phosphate Analogue FTY720 Reduces Atherosclerosis in Apolipoprotein E-Deficient Mice", Mar. 2007, pp. 607-613, vol. 27, Arterioscler Thromb Vasc Biol.

Fujishiro, et al., "Use of Sphingosine-1-Phosphate 1 Receptor Agonist, KRP-203, in Combination with a Subtherapeutic Dose of Cyclosporine A for Rat Renal Transplantation", Sep. 27, 2006, pp. 804-812, vol. 82, No. 6, Transplantation.

Garg, et al., "Sphingosine 1-Phosphate Induces Antimicrobial Activity Both In Vitro and In Vivo", Jun. 1, 2004, pp. 2129-2138, vol. 189, JID.

Goncalves Commodaro, et al., "Evaluation of Experimental Autoimmune Uveitis in Mice Treated with FTY720", May 2010, pp. 2568-2574, vol. 51, No. 5, IOVS.

Kleinjan, et al., "Topical treatment targeting sphingosine-1-phosphate and sphingosine lyase abrogates experimental allergic rhinitis in a murine model", 2012, Allergy.

\* cited by examiner

PIPERIDINYL MONOCARBOXYLIC ACIDS AS S1P1 RECEPTOR AGONISTS

The present invention relates to novel compounds acting as agonists at S1P (sphingosine-1-phosphate) receptors, compositions containing these compounds, use of these compounds in medicine and their process of preparation.

S1P is a bioactive sphingolipid metabolite that is intimately involved in mediating various immunological processes by its actions on S1P receptors. S1P receptor, originally termed as endothelial differentiation gene (EDG) receptor, is a family of five related G-protein coupled receptors, namely S1P1/EDG1, S1P2/EDG5, S1P3/EDG3, S1P4/EDG6 and S1P5/EDG8. These receptors have wide spread cellular and tissue distribution and are well conserved in human and rodent species.

S1P is stored and released from platelets upon their activation, but can also be synthesized in a wide variety of cell types in response to extracellular stimuli like growth factors and cytokines. It is involved in a number of cellular functions including cell growth, differentiation, migration and apoptosis and thus may have an important role in pathophysiological disease states such as atherosclerosis and cancer. S1P exerts these diverse cellular effects depending on the expression of the specific S1P receptors subtypes and its coupling to these receptors.

EDG1 receptor was the first identified S1P receptor that was initially isolated as an orphan GPCR (G protein-coupled receptor) in human endothelial cells, and it was later shown to encode a high-affinity S1P receptor. Expression of EDG1 is pervasive, including spleen, brain, heart, lung, adipose tissues, liver, thymus, kidney, and skeletal muscle. EDG5 was first isolated as an orphan GPCR gene from rat cardiovascular and nervous systems. Its expression is widespread; it is present in heart, lung, thymus, brain, liver, kidney, spleen, adipose tissues in adult mouse, and in lung, heart, stomach, intestine, and adrenal glands in rats. EDG3 was isolated as an orphan GPCR gene by degenerate PCR-based cloning from a human genomic DNA library. Like EDG5, EDG3 is a high-affinity S1P receptor. The expression of EDG3 is widespread; it is present in the spleen, heart, lung, thymus, kidney, testis, brain, and skeletal muscle in adult mice and, in humans, in the heart, placenta, kidney, liver, pancreas, skeletal muscle, lung, and brain. Unlike EDG1, EDG5 and EDG3 receptors, EDG6 expression is restricted in human and mouse to lymph node, spleen, lung, and thymus. This expression pattern suggests potential roles of EDG6 in the immune system. In vivo roles and functions of EDG6 are still unknown. In rat brain, EDG8 is predominantly expressed in white matter tracts and cells of oligodendrocyte lineage, suggesting its potential roles in maturation and myelination of oligodendrocytes. The physiological roles for EDG8 have not been found in the published literature.

EDG1 receptor mediated responses play an essential role in modulating cell trafficking between the lymphatic system and blood. EDG1 receptor agonists cause sequestration of lymphocytes in secondary lymphoid organs which is associated with clinically useful immunosuppression. Immunosuppression is desirable to prevent and/or treat rejection after organ, tissue or cell transplantation and in the treatment of autoimmune disorders. Agents acting as immunosuppressants have been shown to be useful in a variety of autoimmune and inflammatory disorders like transplant rejection, tissue graft rejection, immune disorders, auto immune disorders, autoimmune uveitis, ischemia, rheumatoid arthritis, pollinosis, multiple sclerosis, sepsis, inflammatory bowel disease, asthma, diabetes mellitus, atherosclerosis, lupus erythematosus, myocarditis, multiorgan failure, glomerulonephritis, atopic dermatitis, lymphocytic leukemias, lymphomas, Alzheimer's disease, pneumonia, psoriasis as well as disorders related to impaired vascular integrity, cancers, disregulated angiogenesis or excessive neoangiogenesis.

Recently, FTY720 (Fingolimod), an EDG1 receptor agonist has been approved by FDA for treatment of patients with relapsing form of Multiple Sclerosis. However, there are certain studies which report FTY720 to have an adverse effect of asymptomatic bradycardia, which is reported to be due to nonselective agonism at the EDG3 receptor (*Bioorg. &Med. Chem. Lett.*, 2004, 14, 3501)

Thus, there is a continued interest in developing S1P receptor agonists showing receptor selectivity at EDG1 receptor, specifically, compounds which show low relative activity at EDG3 receptor expressed in cardiac tissues. (Hale et al, Bioorg. Med. Chem. Lett. 14, (2004), 3501-3505). Various EDG1 agonists have been disclosed in prior art references. For example WO2003105771 assigned to Merck discloses EDG1 agonists, which were oxadiazole compounds substituted by aryl group at the 3- and 5-positions. All the compounds disclosed in this application were either azetidinyl- or pyrrolidinyl carboxylic acids. WO2007132307, assigned to Pfizer, discloses EDG1 receptor agonist compounds having oxadiazole ring substituted at 3- and 5-position by aryl group. All the compounds disclosed in this application were aminocycloalkyl carboxylic acids, more specifically aminocyclobutanes substituted by carboxylic acid group. WO2008152149 relates to dicarboxylic acids as EDG1 agonists.

The present invention relates to certain novel piperidine monocarboxylic acids which are effective as agonists on human S1P1 receptors. The present invention relates to a compound of formula (I):

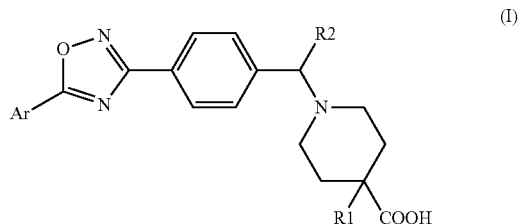

wherein:
Ar is an aryl group optionally substituted by one or more identical or different group(s) selected from halogen, alkyl, cycloalkyl, —Oalkyl, aryl wherein the alkyl, cycloalkyl, —Oalkyl, aryl may be further substituted with halogen, OH, Oalkyl, CN, $NH_2$, NHalkyl, $Nalkyl_2$, alkyl; R1 represents —X—(Y)$_n$
where
—X— is selected from -alkyl-, -alkenyl-, -alkynyl-, -aryl-, -alkylaryl-, Each Y, identical or different is selected from H, OH, halogen, —Oalkyl, —Oalkylaryl, —OalkylOalkyl, —Oaryl, heteroaryl, —Oaryl(Oalkyl), —Ocycloalkyl, -cycloalkyl, heterocyclyl;
n is 1 to 3;
R2 is selected from H, alkyl;
or one of its isomers, salts or esters thereof.

In a preferred embodiment, the present invention relates to the compound of formula (I), wherein Ar is a Phenyl group, more preferably Ar is a disubstituted Phenyl wherein the substituents are as defined above for formula (I).

Unless specified otherwise, the terms used hereabove or hereafter have the meaning ascribed to them below:

"Halo", "hal" or "halogen" refers to fluorine, chlorine, bromine or iodine atom.

"Alkyl" represents an aliphatic-hydrocarbon group which may be straight or branched having 1 to 20 carbon atoms in the chain unless specified otherwise. Preferred alkyl groups have 1 to 12 carbon atoms, more preferably have 1 to 8 carbon atoms in the chain, most preferably have 1 to 6 carbon atoms in the chain. In a particularly preferred embodiment the alkyl group has 1 to 4 carbon atoms in the chain. Exemplary alkyl groups include methyl, ethyl, n-propyl, iso-propyl, iso-butyl, n-butyl, tert-butyl, n-pentyl, 3-pentyl, octyl, nonyl, decyl.

"Cycloalkyl" refers to a non-aromatic mono- or polycyclic hydrocarbon ring system of 3 to 10 carbon atoms. More preferably the cycloalkyl group has of 4 to 10 carbon atoms, more preferably 4 to 8 carbon atoms and most preferably have 4 to 6 carbon atoms. Exemplary monocyclic cycloalkyl include cyclopropyl, cyclobutyl, cyclopentyl, cyclohexyl, cycloheptyl, and the like. Exemplary multicyclic cycloalkyl include 1-decalin, norbornyl, adamant-(1- or 2-)yl.

"Aryl" refers to an aromatic monocyclic, bicyclic or tricyclic hydrocarbon ring system of 6 to 14 carbon atoms. More preferably aryl refers to a nonocyclic or bicyclic ring containing 6 to 10 carbon atoms. Exemplary aryl groups include phenyl, naphthyl, indenyl, phenanthryl, biphenyl. Most preferably the aryl group is Phenyl.

"Alkenyl" refers to an aliphatic hydrocarbon group containing a carbon-carbon double bond and which may be straight or branched having 2 to 15 carbon atoms in the chain unless specified otherwise. Preferred alkenyl groups have 2 to 12 carbon atoms in the chain; more preferably about 2 to 8 carbon atoms in the chain and most preferably have 2 to 4 carbon atoms in the chain. Exemplary alkenyl groups include ethenyl, propenyl, n-butenyl, iso-butenyl, 3-methylbut-2-enyl, n-pentenyl, heptenyl, octenyl, nonenyl, decenyl.

"Alkynyl" refers to an aliphatic hydrocarbon group containing a carbon-carbon triple bond and which may be straight or branched having 2 to 15 carbon atoms in the chain unless specified otherwise. Preferred alkynyl groups have 2 to 12 carbon atoms in the chain; more preferably have 2 to 8 carbon atoms in the chain, most preferably have 2 to 4 carbon atoms in the chain. Exemplary alkynyl groups include ethynyl, propynyl, n-butynyl, 2-butynyl, 3-methyl-1-butynyl, n-pentynyl, 4,4-dimethyl-2-pentynyl, heptynyl, octynyl and decynyl.

"Arylalkyl" refers to an alkyl group substituted with an aryl group. The terms "alkyl" and "aryl" are as defined above.

"—Oarylalkyl" refers to a group wherein —O is attached to an alkyl group which is substituted with an aryl group. The terms "alkyl" and "aryl" are as defined above. Exemplary "Oarylalkyl" groups include —O—CH$_2$-Phenyl.

The term "heteroaryl" refers to a 5 to 14, preferably 5 to 10 membered aromatic mono-, bi- or multicyclic ring wherein at least one member of the ring is a hetero atom such as N, O, S. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl.

The terms "heterocycle", "heterocyclyl" or "heterocyclic" refer to a saturated or partially unsaturated non aromatic stable 3 to 14, preferably 5 to 10-membered mono, bi or multicyclic rings wherein at least one member of the ring is a hetero atom, such as N, O, S. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in the *Handbook of Chemistry and Physics*, 76th Edition, CRC Press, Inc., 1995-1996, pages 2-25 to 2-26, the disclosure of which is hereby incorporated by reference. Preferred non aromatic heterocyclic include, but are not limited to oxetanyl, tetraydrofuranyl, dioxolanyl, tetrahydropyranyl, dioxanyl, pyrrolidinyl, piperidyl, morpholinyl, imidazolidinyl, pyranyl. Preferred saturated heterocycles are chosen from tetrahydrofuranyl, dioxolanyl, tetrahydropyranyl, dioxanyl, pyrrolidinyl, piperidyl, morpholinyl, imidazolidinyl, more preferably tetrahydrofuranyl, dioxolanyl, tetrahydropyranyl.

"Alkyl", "cycloalkyl", "alkenyl", "alkynyl", "aryl", etc. . . . also refers to the corresponding divalent "alkylene", "cycloalkylene", "alkenylene", "alkynylene", "arylene", etc., which are formed by the removal of two hydrogen atoms.

The compounds of the present invention possess an acidic group and a basic group which may form corresponding salts. Thus the present invention includes salts of compounds of formula (I). The salts may preferably be pharmaceutically acceptable salts. The acidic group may form salts with bases. The base may be an organic amine base, for example trimethylamine, tert-butylamine, tromethamine, meglumine, epolamine, etc. The acidic group may also form salts with inorganic bases like sodium hydroxide, potassium hydroxide, etc. The basic group may form salts with inorganic acids like hydrochloric acid, sulfuric acid, hydrobromic acid, sulfamic acid, phosphoric acid, nitric acid etc and organic acids like acetic acid, propionic acid, succinic acid, tartaric acid, citric acid, methanesulfonic acid, benzenesulfonic acid, glucoronic acid, glutamic acid, benzoic acid, salicylic acid, toluenesulfonic acid, oxalic acid, fumaric acid, maleic acid etc. Further, compounds of formula (I) may form quaternary ammonium salts and salts with amino acids such as arginine, lysine, etc. Lists of suitable salts may be found in Remington's Pharmaceutical Sciences, 17th ed., Mack Publishing Company, Easton, Pa., 1985, p. 1418 and P. H. Stahl, C. G. Wermuth, *Handbook of Pharmaceutical salts—Properties, Selection and Use*, Wiley-VCH, 2002, the disclosures of which are hereby incorporated by reference.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, the expression "pharmaceutically acceptable" refers to those compounds, materials, compositions, or dosage forms which are, within the scope of sound medical judgment, suitable for contact with the tissues of human beings and animals without excessive toxicity, irritation, allergic response, or other problem complications commensurate with a reasonable benefit/risk ratio.

A preferred embodiment of compound of formula (I) is represented by a compound of formula (II):

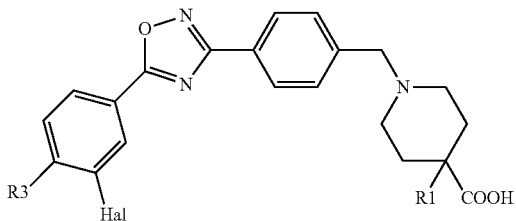

(II)

or one of its isomers, salts or esters thereof
wherein:
R1 is selected as in formula (I); and/or
R3 is selected from halogen, $C_{1-6}$ alkyl, $C_{3-7}$cycloalkyl, —O—$C_{1-6}$alkyl, aryl; More preferably R3 is selected from methyl, ethyl, n-propyl, isopropyl, n-butyl, isobutyl, secondary butyl, tertiary butyl, n-pentyl, isopentyl, n-hexyl, isohexyl, cyclopentyl, cyclohexyl, cycloheptyl, isopropoxy, phenyl. Most preferably R3 is selected from phenyl, cyclohexyl, cyclopentyl, isobutyl; and/or Hal represents a halogen, such as F, Cl, Br, I.

Another preferred embodiment of the present invention relates to compound of formula (II) wherein R1 is selected from $C_{1-6}$ alkyl, $C_{2-4}$ alkenyl, $C_{2-4}$ alkynyl, aryl and arylalkyl each being optionally substituted by one or more of OH, halogen, —Oalkyl, —Oarylalkyl, —OalkylOalkyl, Oaryl, heteroaryl, —Oaryl(Oalkyl), —Ocycloalkyl, -cycloalkyl, heterocyclyl.

More preferably R1 is selected from methyl, ethyl, n-propyl, isopropyl, n-butyl, isobutyl, secondary butyl, tertiary butyl, n-pentyl, isopentyl, n-hexyl, isohexyl, hydroxymethyl, hydroxyethyl, hydroxypropyl, methoxymethyl, ethoxymethyl, methoxyethyl, vinyl, allyl, methoxyethoxymethyl, ethoxyethoxymethyl, ethoxyethoxyethyl, Phenyl, benzyl, benzyloxymethyl, benzyloxyethyl, —$CH_2$-[Ph(o-F)], —$CH_2$-[Ph(m-F)], —$CH_2$-[Ph(p-F)], —$CH_2$-[Ph(o-OMe)], —$CH_2$-[Ph(m-OMe)], —$CH_2$-[Ph(p-OMe)], methoxybutyl, methoxyethoxymethyl, —$CH_2$-[Ph(o,o-$F_2$)], —$CH_2$-[Ph(m-$CF_3$)], —$CH_2$-furyl, —$CH_2$-pyridyl, (2-methoxy-phenoxy)-ethyl, 4-methoxy-benzyl, isopropoxymethyl, cyclopentyloxymethyl, thiophen-2-ylmethyl, cyclopropylmethyl, 2-morpholin-4-yl-ethyl, 3-piperidin-1-yl-propyl, 3-pyrrolidin-1-yl-propyl.

Still more preferably, R1 is selected from methyl, ethyl, n-propyl, hydroxymethyl, methoxymethyl, allyl, methoxyethoxymethyl, Phenyl, benzyl, benzyloxymethyl, —$CH_2$-[Ph(o-F)], —$CH_2$-[Ph(p-F)], —$CH_2$-[Ph(o-OMe)], —$CH_2$-[Ph(p-OMe)], methoxybutyl, methoxyethoxymethyl, —$CH_2$-[Ph(o,o-$F_2$)], —$CH_2$-[Ph(m-$CF_3$)], —$CH_2$-furyl, —$CH_2$-pyridyl, (2-methoxy-phenoxy)-ethyl, 4-methoxy-benzyl, isopropoxymethyl, cyclopentyloxymethyl, thiophen-2-ylmethyl, cyclopropylmethyl, 2-morpholin-4-yl-ethyl, 3-piperidin-1-yl-propyl, 3-pyrrolidin-1-yl-propyl.

wherein, p-F, o-F, p-OMe and o-OMe stands for para-fluoro, ortho-fluoro, para-methoxy and ortho-methoxy respectively.

More preferably, the invention relates to a compound of formula (I) or (II) above, wherein:
R1 is selected from —$CH_3$, —$C_2H_5$, -n-$C_3H_7$, —$CH_2$—O—$CH_3$, —$CH_2$—CH=$CH_2$, —$CH_2$—O—$CH_2$—$CH_2$—$OCH_3$, -Ph, —$CH_2$—O—$CH_2$-Ph, —$CH_2$-Ph, —$CH_2$-[Ph(p-F)], —$CH_2$-[Ph(o-F)], —$CH_2$-[Ph(p-OMe)], —$CH_2$-[Ph(o-OMe)] or —$CH_2OH$, methoxybutyl, methoxyethoxymethyl, methoxyethoxyethyl, —$CH_2$—$CH_2$—O-Ph, —$CH(CH_3)_2$, —$CH_2$-[Ph(o,o-$F_2$)], —$CH_2$-[Ph(m-$CF_3$)], —$CH_2$-furyl, —$CH_2$-pyridyl, (2-methoxy-phenoxy)-ethyl, 4-methoxy-benzyl, isopropoxymethyl, cyclopentyloxymethyl, thiophen-2-ylmethyl, cyclopropylmethyl, 2-morpholin-4-yl-ethyl, 3-piperidin-1-yl-propyl, 3-pyrrolidin-1-yl-propyl; and/or
R3 is selected from phenyl, cyclohexyl, cyclopentyl, isobutyl, isopropoxy; wherein, p-F, o-F, p-OMe and o-OMe stands for para-fluoro, ortho-fluoro, para-methoxy and ortho-methoxy respectively.

Still more preferably, the invention relates to a compound of formula (I) or (II) wherein
when R1 is —$CH_3$, —$C_2H_5$, -n-$C_3H_7$, —$CH_2$—O—$CH_3$, —$CH_2$—CH=$CH_2$, —$CH_2$—O—$CH_2$—$CH_2$—$OCH_3$, -Ph, —$CH_2$—O—$CH_2$-Ph, —$CH_2$-Ph, —$CH_2$-[Ph(p-F)], —$CH_2$-[Ph(o-F)], —$CH_2$-[Ph(p-OMe)], —$CH_2$-[Ph(o-OMe)], —$CH_2OH$, methoxybutyl, methoxyethoxymethyl, methoxyethoxyethyl, isopropoxymethyl, —$CH_2$—$CH_2$—O-Ph, —$CH(CH_3)_2$—$CH_2$-[Ph(o,o-$F_2$)], —$CH_2$-[Ph(m-$CF_3$)], —$CH_2$-furyl, —$CH_2$-pyridyl, (2-methoxy-phenoxy)-ethyl, 4-methoxy-benzyl, isopropoxymethyl, cyclopentyloxymethyl, thiophen-2-ylmethyl, cyclopropylmethyl, 2-morpholin-4-yl-ethyl, 3-piperidin-1-yl-propyl, 3-pyrrolidin-1-yl-propyl,
then R3 is isobutyl;
when R1 is —$CH_3$, —$C_2H_5$, -n-$C_3H_7$, —$CH_2$—O—$CH_3$, —$CH_2$—CH=$CH_2$, —$CH_2$—O—$CH_2$—$CH_2$—$OCH_3$, —$CH_2$—O—$CH_2$-Ph, —$CH_2$-pyridyl, $CH_2$-[Ph(OMe)], —$CH_2$-[Ph(F)], —$CH_2$-Ph or —$CH_2OH$ then R3 is -Ph;
when R1 is —$CH_3$, —$CH_2CH_3$, —$CH_2$—O—$CH_3$, $CH_2$-[Ph(OMe)], then R3 is -cyclohexyl;
when R1 is —$CH_3$ or —$CH_2$—O—$CH_3$ then R3 is cyclopentyl;
when R1 is —$CH_2$—$CH_3$, —$CH_2$—CH=$CH_2$, —$CH_2$—O—$CH_3$ or —$CH_2$—O—$CH_2$—$CH_2$—O—$CH_3$ then R3 is isopropoxy.

Following are examples of some of the representative compounds of the invention. These examples are for illustration purposes only and should not be considered to be limiting the invention.

1-{4-[5-(3-chloro-4-cyclohexylphenyl)-[1,2,4]-oxadiazol-3-yl]benzyl}-4-methylpiperidine-4-carboxylic acid
1-{4-[5-(3-chloro-4-isobutylphenyl)-[1,2,4]-oxadiazol-3-yl]benzyl}-4-methylpiperidine-4-carboxylic acid
1-{4-[5-(3-chloro-4-cyclopentylphenyl)-[1,2,4]-oxadiazol-3-yl]benzyl}-4-methylpiperidine-4-carboxylic acid
1-{4-[5-(2-chlorobiphenyl-4-yl)-[1,2,4]-oxadiazol-3-yl]benzyl}-4-methylpiperidine-4-carboxylic acid
1-{4-[5-(3-chloro-4-cyclopentylphenyl)-[1,2,4]-oxadiazol-3-yl]benzyl}-4-methoxymethylpiperidine-4-carboxylic acid
1-{4-[5-(3-chloro-4-cyclohexylphenyl)-[1,2,4]-oxadiazol-3-yl]benzyl}-4-methoxymethylpiperidine-4-carboxylic acid
1-{4-[5-(3-chloro-4-isobutylphenyl)-[1,2,4]-oxadiazol-3-yl]benzyl}-4-ethylpiperidine-4-carboxylic acid
4-allyl-1-{4-[5-(3-chloro-4-isobutylphenyl)-[1,2,4]-oxadiazol-3-yl]benzyl}piperidine-4-carboxylic acid
1-{4-[5-(3-chloro-4-isobutylphenyl)-[1,2,4]-oxadiazol-3-yl]benzyl}-4-propylpiperidine-4-carboxylic acid
1-{4-[5-(3-chloro-4-isobutylphenyl)-[1,2,4]-oxadiazol-3-yl]benzyl}-4-(2-methoxyethoxymethyl)piperidine-4-carboxylic acid
1-{4-[5-(3-chloro-4-isobutylphenyl)-[1,2,4]-oxadiazol-3-yl]benzyl}-4-hydroxymethylpiperidine-4-carboxylic acid
1-{4-[5-(3-Chloro-4-isobutylphenyl)-[1,2,4]oxadiazol-3-yl]-benzyl}-4-methoxymethylpiperidine-4-carboxylic acid 4-Allyl-1-{4-[5-(2-chlorobiphenyl-4-yl)-[1,2,4]-oxadiazol-3-yl]-benzyl}piperidine-4-carboxylic acid
1-{4-[5-(2-Chlorobiphenyl-4-yl)-[1,2,4]-oxadiazol-3-yl]-benzyl}-4-propylpiperidine-4-carboxylic acid
1-{4-[5-(2-Chlorobiphenyl-4-yl)-[1,2,4]-oxadiazol-3-yl]-benzyl}-4-(2-methoxyethoxymethyl)piperidine-4-carboxylic acid
4-Benzyloxymethyl-1-{4-[5-(2-chlorobiphenyl-4-yl)-[1,2,4]-oxadiazol-3-yl]-benzyl}piperidine-4-carboxylic acid
4-Benzyloxymethyl-1-{4-[5-(3-chloro-4-isobutylphenyl)-[1,2,4]-oxadiazol-3-yl]-benzyl}piperidine-4-carboxylic acid
1-{4-[5-(2-Chlorobiphenyl-4-yl)-[1,2,4]-oxadiazol-3-yl]-benzyl}-4-hydroxymethylpiperidine-4-carboxylic acid
1-{4-[5-(3-Chloro-4-isobutylphenyl)-[1,2,4]-oxadiazol-3-yl]-benzyl}-4-phenylpiperidine-4-carboxylic acid
4-Benzyl-1-{4-[5-(3-chloro-4-isobutylphenyl)-[1,2,4]-oxadiazol-3-yl]benzyl}-piperidine-4-carboxylic acid
1-{4-[5-(3-Chloro-4-isobutyl-phenyl)-[1,2,4]oxadiazol-3-yl]-benzyl}-4-(4-fluoro-benzyl)-piperidine-4-carboxylic acid
1-{4-[5-(3-Chloro-4-isobutyl-phenyl)-[1,2,4]oxadiazol-3-yl]-benzyl}-4-(2-fluoro-benzyl)-piperidine-4-carboxylic acid
1-{4-[5-(3-Chloro-4-isobutyl-phenyl)-[1,2,4]oxadiazol-3-yl]-benzyl}-4-(4-methoxy-benzyl)-piperidine-4-carboxylic acid
1-{4-[5-(3-Chloro-4-isobutyl-phenyl)-[1,2,4]oxadiazol-3-yl]-benzyl}-4-(2-methoxy-benzyl)-piperidine-4-carboxylic acid
1-{4-[5-(2-chlorobiphenyl-4-yl)-[1,2,4]-oxadiazol-3-yl]benzyl}-4-methoxymethylpiperidine-4-carboxylic acid
1-{4-[5-(2-Chlorobiphenyl-4-yl)-[1,2,4]-oxadiazol-3-yl]-benzyl}-4-ethylpiperidine-4-carboxylic acid
1-{4-[5-(4-Isobutyl-phenyl)-[1,2,4]-oxadiazol-3-yl]-benzyl}-4-methyl-piperidine-4-carboxylic acid
1-{4-[5-(3-Chloro-4-isobutyl-phenyl)-[1,2,4]-oxadiazol-3-yl]-benzyl}-4-(4-methoxy-butyl)-piperidine-4-carboxylic acid
1-{4-[5-(3-chloro-4-isobutylphenyl)-[1,2,4]-oxadiazol-3-yl]benzyl}-4-(2-methoxyethoxymethyl)piperidine-4-carboxylic acid
1-{4-[5-(3-Chloro-4-isobutyl-phenyl)-[1,2,4]-oxadiazol-3-yl]-benzyl}-4-(2-phenoxy-ethyl)-piperidine-4-carboxylic acid
1-{4-[5-(3-Chloro-4-isobutyl-phenyl)-[1,2,4]-oxadiazol-3-yl]-benzyl}-4-(2,6-difluoro-benzyl)-piperidine-4-carboxylic acid
1-{4-[5-(3-Chloro-4-isobutyl-phenyl)-[1,2,4]-oxadiazol-3-yl]-benzyl}-4-isobutyl-piperidine-4-carboxylic acid
1-{4-[5-(3-Chloro-4-isobutyl-phenyl)-[1,2,4]-oxadiazol-3-yl]-benzyl}-4-isopropyl-piperidine-4-carboxylic acid
1-{4-[5-(3-Chloro-4-isobutyl-phenyl)-[1,2,4]-oxadiazol-3-yl]-benzyl}-4-(3-trifluoro methyl-benzyl)-piperidine-4-carboxylic acid
1-{4-[5-(3-Chloro-4-isobutyl-phenyl)-[1,2,4]oxadiazol-3-yl]-benzyl}-4-furan-2-ylmethyl-piperidine-4-carboxylic acid
1-{4-[5-(3-Chloro-4-isobutyl-phenyl)-[1,2,4]-oxadiazol-3-yl]-benzyl}-4-pyridin-2-ylmethyl-piperidine-4-carboxylic acid
1-{4-[5-(3-Chloro-4-isobutyl-phenyl)-[1,2,4]-oxadiazol-3-yl]-benzyl}-4-[2-(2-methoxy-phenoxy)-ethyl]-piperidine-4-carboxylic acid
1-{4-[5-(3-Chloro-4-isobutyl-phenyl)-[1,2,4]-oxadiazol-3-yl]-benzyl}-4-pyridin-3-ylmethyl-piperidine-4-carboxylic acid
1-{4-[5-(3-Chloro-4-isobutyl-phenyl)-[1,2,4]-oxadiazol-3-yl]-benzyl}-4-pyridin-4-ylmethyl-piperidine-4-carboxylic acid
1-{4-[5-(3-Chloro-4-isopropoxy-phenyl)-[1,2,4]-oxadiazol-3-yl]-benzyl}-4-methyl-piperidine-4-carboxylic acid
1-{4-[5-(4-tert-Butyl-3-chloro-phenyl)-[1,2,4]-oxadiazol-3-yl]-benzyl}-4-methyl-piperidine-4-carboxylic acid
1-{4-[5-(3-Chloro-4-propyl-phenyl)-[1,2,4]-oxadiazol-3-yl]-benzyl}-4-methyl-piperidine-4-carboxylic acid
1-{4-[5-(3-Chloro-4-isopropoxy-phenyl)-[1,2,4]-oxadiazol-3-yl]-benzyl}-4-(2-methoxy-ethoxymethyl)-piperidine-4-carboxylic acid
1-{4-[5-(3-Chloro-4-isopropoxy-phenyl)-[1,2,4]-oxadiazol-3-yl]-benzyl}-4-ethyl-piperidine-4-carboxylic acid
4-Allyl-1-{4-[5-(3-chloro-4-isopropoxy-phenyl)-[1,2,4]-oxadiazol-3-yl]-benzyl}-piperidine-4-carboxylic acid
1-{4-[5-(2-Chloro-biphenyl-4-yl)-[1,2,4]-oxadiazol-3-yl]-benzyl}-4-pyridin-2-ylmethyl-piperidine-4-carboxylic acid
1-{4-[5-(2-Chloro-biphenyl-4-yl)-[1,2,4]-oxadiazol-3-yl]-benzyl}-4-(4-methoxy-benzyl)-piperidine-4-carboxylic acid
1-{4-[5-(2-Chloro-biphenyl-4-yl)-[1,2,4]-oxadiazol-3-yl]-benzyl}-4-(4-fluoro-benzyl)-piperidine-4-carboxylic acid
1-{4-[5-(3-Chloro-4-cyclohexylphenyl)-[1,2,4]-oxadiazol-3-yl]-benzyl}-4-(4-methoxy-benzyl)-piperidine-4-carboxylic acid
1-{4-[5-(3-Chloro-4-cyclohexylphenyl)-[1,2,4]-oxadiazol-3-yl]-benzyl}-4-ethyl-piperidine-4-carboxylic acid
4-Benzyl-1-{4-[5-(2-chloro-biphenyl-4-yl)-[1,2,4]-oxadiazol-3-yl]-benzyl}-piperidine-4-carboxylic acid
1-{4-[5-(3-Chloro-4-cyclohexyl-phenyl)-[1,2,4]-oxadiazol-3-yl]-benzyl}-4-pyridin-2-ylmethyl-piperidine-4-carboxylic acid
1-{4-[5-(3-Chloro-4-isopropoxy-phenyl)-[1,2,4]-oxadiazol-3-yl]-benzyl}-4-methoxymethyl-piperidine-4-carboxylic acid
1-{4-[5-(2-Chloro-biphenyl-4-yl)-[1,2,4]-oxadiazol-3-yl]-benzyl}-4-pyridin-3-ylmethyl-piperidine-4-carboxylic acid
1-{4-[5-(3-Chloro-4-isobutyl-phenyl)-[1,2,4]-oxadiazol-3-yl]-benzyl}-4-(2-ethoxy-ethoxymethyl)-piperidine-4-carboxylic acid
1-{4-[5-(3-Chloro-4-isobutyl-phenyl)-[1,2,4]-oxadiazol-3-yl]-benzyl}-4-isopropoxy methyl-piperidine-4-carboxylic acid
1-{4-[5-(3-Chloro-4-isobutyl-phenyl)-[1,2,4]-oxadiazol-3-yl]-benzyl}-4-cyclopentyloxymethyl-piperidine-4-carboxylic acid
1-{4-[5-(3-Chloro-4-isobutyl-phenyl)-[1,2,4]-oxadiazol-3-yl]-benzyl}-4-thiophen-2-ylmethyl-piperidine-4-carboxylic acid
1-{4-[5-(3-Chloro-4-isobutyl-phenyl)-[1,2,4]-oxadiazol-3-yl]-benzyl}-4-cyclopropylmethyl-piperidine-4-carboxylic acid
1-{4-[5-(3-Chloro-4-isobutyl-phenyl)-[1,2,4]-oxadiazol-3-yl]-benzyl}-4-(2-morpholin-4-yl-ethyl)-piperidine-4-carboxylic acid
1-{4-[5-(3-Chloro-4-isobutyl-phenyl)-[1,2,4]oxadiazol-3-yl]-benzyl}-4-(3-piperidin-1-yl-propyl)-piperidine-4-carboxylic acid
1-{4-[5-(3-Chloro-4-isobutyl-phenyl)-[1,2,4]oxadiazol-3-yl]-benzyl}-4-(3-pyrrolidin-1-yl-propyl)-piperidine-4-carboxylic acid
or one of their isomers, salts or esters thereof.

More preferable compounds of the invention include the following:

1-{4-[5-(3-chloro-4-cyclohexylphenyl)-[1,2,4]-oxadiazol-3-yl]benzyl}-4-methylpiperidine-4-carboxylic acid
1-{4-[5-(3-chloro-4-isobutylphenyl)-[1,2,4]-oxadiazol-3-yl]benzyl}-4-methylpiperidine-4-carboxylic acid, tert-butylamine salt
1-{4-[5-(3-chloro-4-isobutylphenyl)-[1,2,4]-oxadiazol-3-yl]benzyl}-4-methylpiperidine-4-carboxylic acid
1-{4-[5-(3-chloro-4-isobutylphenyl)-[1,2,4]-oxadiazol-3-yl]benzyl}-4-methylpiperidine-4-carboxylic acid, sodium salt
1-{4-[5-(3-chloro-4-isobutylphenyl)-[1,2,4]-oxadiazol-3-yl]benzyl}-4-methylpiperidine-4-carboxylic acid, arginine salt
1-{4-[5-(3-chloro-4-isobutylphenyl)-[1,2,4]-oxadiazol-3-yl]benzyl}-4-methylpiperidine-4-carboxylic acid, potassium salt
1-{4-[5-(3-chloro-4-cyclopentylphenyl)-[1,2,4]-oxadiazol-3-yl]benzyl}-4-methylpiperidine-4-carboxylic acid
1-{4-[5-(2-Chlorobiphenyl-4-yl)-[1,2,4]-oxadiazol-3-yl]benzyl}-4-methylpiperidine-4-carboxylic acid
1-{4-[5-(3-chloro-4-cyclopentylphenyl)-[1,2,4]-oxadiazol-3-yl]benzyl}-4-methoxymethylpiperidine-4-carboxylic acid, tert-butylamine salt
1-{4-[5-(3-chloro-4-cyclohexylphenyl)-[1,2,4]-oxadiazol-3-yl]benzyl}-4-methoxymethylpiperidine-4-carboxylic acid tert-butylamine salt
1-{4-[5-(3-chloro-4-isobutylphenyl)-[1,2,4]-oxadiazol-3-yl]benzyl}-4-ethylpiperidine-4-carboxylic acid tert-butylamine salt
4-allyl-1-{4-[5-(3-chloro-4-isobutylphenyl)-[1,2,4]-oxadiazol-3-yl]benzyl}piperidine-4-carboxylic acid tert-butylamine salt
1-{4-[5-(3-chloro-4-isobutylphenyl)-[1,2,4]-oxadiazol-3-yl]benzyl}-4-propylpiperidine-4-carboxylic acid tert-butylamine salt
1-{4-[5-(3-chloro-4-isobutylphenyl)-[1,2,4]-oxadiazol-3-yl]benzyl}-4-(2-methoxyethoxymethyl)piperidine-4-carboxylic acid tert-butylamine salt
1-{4-[5-(3-chloro-4-isobutylphenyl)-[1,2,4]-oxadiazol-3-yl]benzyl}-4-hydroxymethylpiperidine-4-carboxylic acid tert-butylamine salt
1-{4-[5-(3-Chloro-4-isobutylphenyl)-[1,2,4]oxadiazol-3-yl]-benzyl}-4-methoxymethylpiperidine-4-carboxylic acid tert-butylamine salt
4-Allyl-1-{4-[5-(2-chlorobiphenyl-4-yl)-[1,2,4]-oxadiazol-3-yl]-benzyl}piperidine-4-carboxylic acid tert-butylamine salt
1-{4-[5-(2-Chlorobiphenyl-4-yl)-[1,2,4]-oxadiazol-3-yl]-benzyl}-4-propylpiperidine-4-carboxylic acid tert-butylamine salt
1-{4-[5-(2-Chlorobiphenyl-4-yl)-[1,2,4]-oxadiazol-3-yl]-benzyl}-4-(2-methoxyethoxymethyl)piperidine-4-carboxylic acid tert-butylamine salt
4-Benzyloxymethyl-1-{4-[5-(2-chlorobiphenyl-4-yl)-[1,2,4]-oxadiazol-3-yl]-benzyl}piperidine-4-carboxylic acid tert-butylamine salt
4-Benzyloxymethyl-1-{4-[5-(3-chloro-4-isobutylphenyl)-[1,2,4]-oxadiazol-3-yl]-benzyl}piperidine-4-carboxylic acid tert-butylamine salt
1-{4-[5-(2-Chlorobiphenyl-4-yl)-[1,2,4]-oxadiazol-3-yl]-benzyl}-4-hydroxymethylpiperidine-4-carboxylic acid tert-butylamine salt
1-{4-[5-(3-Chloro-4-isobutylphenyl)-[1,2,4]-oxadiazol-3-yl]-benzyl}-4-phenylpiperidine-4-carboxylic acid tert-butylamine salt
4-Benzyl-1-{4-[5-(3-chloro-4-isobutylphenyl)-[1,2,4]-oxadiazol-3-yl]benzyl}-piperidine-4-carboxylic acid tert-butylamine salt
1-{4-[5-(3-Chloro-4-isobutyl-phenyl)-[1,2,4]oxadiazol-3-yl]-benzyl}-4-(4-fluoro-benzyl)-piperidine-4-carboxylic acid tert-butylamine salt
1-{4-[5-(3-Chloro-4-isobutyl-phenyl)-[1,2,4]oxadiazol-3-yl]-benzyl}-4-(2-fluoro-benzyl)-piperidine-4-carboxylic acid tert-butylamine salt
1-{4-[5-(3-Chloro-4-isobutyl-phenyl)-[1,2,4]oxadiazol-3-yl]-benzyl}-4-(4-methoxy-benzyl)-piperidine-4-carboxylic acid tert-butylamine salt
1-{4-[5-(3-Chloro-4-isobutyl-phenyl)-[1,2,4]oxadiazol-3-yl]-benzyl}-4-(2-methoxy-benzyl)-piperidine-4-carboxylic acid tert-butylamine salt
1-{4-[5-(2-chlorobiphenyl-4-yl)-[1,2,4]-oxadiazol-3-yl]benzyl}-4-methoxymethylpiperidine-4-carboxylic acid tert-butylamine salt
1-{4-[5-(2-Chlorobiphenyl-4-yl)-[1,2,4]-oxadiazol-3-yl]-benzyl}-4-ethylpiperidine-4-carboxylic acid tert-butylamine salt
1-{4-[5-(4-Isobutyl-phenyl)-[1,2,4]-oxadiazol-3-yl]-benzyl}-4-methyl-piperidine-4-carboxylic acid tert-butyl amine salt
1-{4-[5-(3-Chloro-4-isobutyl-phenyl)-[1,2,4]-oxadiazol-3-yl]-benzyl}-4-(4-methoxy-butyl)-piperidine-4-carboxylic acid tert-butyl amine salt
1-{4-[5-(3-chloro-4-isobutylphenyl)-[1,2,4]-oxadiazol-3-yl]benzyl}-4-(2-methoxyethoxymethyl)piperidine-4-carboxylic acid potassium salt
1-{4-[5-(3-Chloro-4-isobutyl-phenyl)-[1,2,4]-oxadiazol-3-yl]-benzyl}-4-(2-phenoxy-ethyl)-piperidine-4-carboxylic acid tert-butyl amine salt
1-{4-[5-(3-Chloro-4-isobutyl-phenyl)-[1,2,4]-oxadiazol-3-yl]-benzyl}-4-(2,6-difluoro-benzyl)-piperidine-4-carboxylic acid tert-butyl amine salt
1-{4-[5-(3-Chloro-4-isobutyl-phenyl)-[1,2,4]-oxadiazol-3-yl]-benzyl}-4-isobutyl-piperidine-4-carboxylic acid tert-butyl amine salt
1-{4-[5-(3-Chloro-4-isobutyl-phenyl)-[1,2,4]-oxadiazol-3-yl]-benzyl}-4-isopropyl-piperidine-4-carboxylic acid tert-butyl amine salt
1-{4-[5-(3-Chloro-4-isobutyl-phenyl)-[1,2,4]-oxadiazol-3-yl]-benzyl}-4-(3-trifluoro methyl-benzyl)-piperidine-4-carboxylic acid tert-butyl amine salt
1-{4-[5-(3-Chloro-4-isobutyl-phenyl)-[1,2,4]oxadiazol-3-yl]-benzyl}-4-furan-2-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-pyridin-2-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-[2-(2-methoxy-phenoxy)-ethyl]-piperidine-4-carboxylic acid tert-butyl amine salt
1-{4-[5-(3-Chloro-4-isobutyl-phenyl)-[1,2,4]-oxadiazol-3-yl]-benzyl}-4-pyridin-3-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-pyridin-4-ylmethyl-piperidine-4-carboxylic acid tert-butyl amine salt
1-{4-[5-(3-Chloro-4-isopropoxy-phenyl)-[1,2,4]-oxadiazol-3-yl]-benzyl}-4-methyl-piperidine-4-carboxylic acid tert-butyl amine salt
1-{4-[5-(4-tert-Butyl-3-chloro-phenyl)-[1,2,4]-oxadiazol-3-yl]-benzyl}-4-methyl-piperidine-4-carboxylic acid tert-butyl amine salt 1-{4-[5-(3-Chloro-4-propyl-phenyl)-[1,2,4]-oxadiazol-3-yl]-benzyl}-4-methyl-piperidine-4-carboxylic acid tert-butyl amine salt
1-{4-[5-(3-Chloro-4-isopropoxy-phenyl)-[1,2,4]-oxadiazol-3-yl]-benzyl}-4-(2-methoxy-ethoxymethyl)-piperidine-4-carboxylic acid tert-butyl amine salt
1-{4-[5-(3-Chloro-4-isopropoxy-phenyl)-[1,2,4]-oxadiazol-3-yl]-benzyl}-4-ethyl-piperidine-4-carboxylic acid tert-butyl amine salt
4-Allyl-1-{4-[5-(3-chloro-4-isopropoxy-phenyl)-[1,2,4]-oxadiazol-3-yl]-benzyl}-piperidine-4-carboxylic acid tert-butyl amine salt
1-{4-[5-(2-Chloro-biphenyl-4-yl)-[1,2,4]-oxadiazol-3-yl]-benzyl}-4-pyridin-2-ylmethyl-piperidine-4-carboxylic acid tert-butyl amine salt
1-{4-[5-(2-Chloro-biphenyl-4-yl)-[1,2,4]-oxadiazol-3-yl]-benzyl}-4-(4-methoxy-benzyl)-piperidine-4-carboxylic acid tert-butyl amine salt
1-{4-[5-(2-Chloro-biphenyl-4-yl)-[1,2,4]-oxadiazol-3-yl]-benzyl}-4-(4-fluoro-benzyl)-piperidine-4-carboxylic acid tert-butyl amine salt
1-{4-[5-(3-Chloro-4-cyclohexylphenyl)-[1,2,4]-oxadiazol-3-yl]-benzyl}-4-(4-methoxy-benzyl)-piperidine-4-carboxylic acid tert-butyl amine salt
1-{4-[5-(3-Chloro-4-cyclohexylphenyl)-[1,2,4]-oxadiazol-3-yl]-benzyl}-4-ethyl-piperidine-4-carboxylic acid tert-butyl amine salt
4-Benzyl-1-{4-[5-(2-chloro-biphenyl-4-yl)-[1,2,4]-oxadiazol-3-yl]-benzyl}-piperidine-4-carboxylic acid tert-butyl amine salt
1-{4-[5-(3-Chloro-4-cyclohexyl-phenyl)-[1,2,4]-oxadiazol-3-yl]-benzyl}-4-pyridin-2-ylmethyl-piperidine-4-carboxylic acid tert-butyl amine salt
1-{4-[5-(3-Chloro-4-isopropoxy-phenyl)-[1,2,4]-oxadiazol-3-yl]-benzyl}-4-methoxymethyl-piperidine-4-carboxylic acid tert-butyl amine salt
1-{4-[5-(2-Chloro-biphenyl-4-yl)-[1,2,4]-oxadiazol-3-yl]-benzyl}-4-pyridin-3-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-(2-ethoxy-ethoxymethyl)-piperidine-4-carboxylic acid tert-butyl amine salt
1-{4-[5-(3-Chloro-4-isobutyl-phenyl)-[1,2,4]-oxadiazol-3-yl]-benzyl}-4-isopropoxy methyl-piperidine-4-carboxylic acid tert-butyl amine salt
1-{4-[5-(3-Chloro-4-isobutyl-phenyl)-[1,2,4]-oxadiazol-3-yl]-benzyl}-4-cyclopentyloxymethyl-piperidine-4-carboxylic acid tert-butyl amine salt
1-{4-[5-(3-Chloro-4-isobutyl-phenyl)-[1,2,4]-oxadiazol-3-yl]-benzyl}-4-thiophen-2-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-cyclopropylmethyl-piperidine-4-carboxylic acid tert-butyl amine salt
or one of their isomers.

According to a further object, the present invention also concerns the process of preparation of the compound of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

In particular, the compounds of the present invention may be prepared from the processes described below. The intermediates used in the processes are either commercially available or may be synthesized in the laboratory from well-known starting materials and processes. The process of preparing the compounds of the present invention is apparent or readily obtainable from prior art references, eg. WO2003/105771, WO2008152149

According to a first embodiment, the process of preparation of a compound of formula (I) comprises saponifying a compound of formula (III):

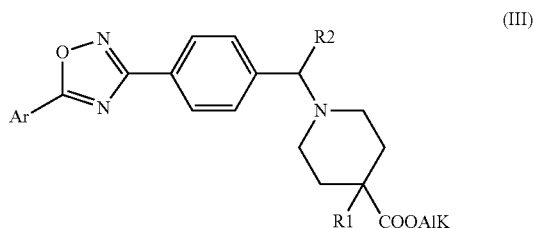

(III)

where Ar, R2, R1 are defined as in formula (I) and Alk represents an alkyl group, optionally followed by forming the desired addition salt.

The saponification reaction is generally conducted in the presence of a mineral base such as NaOH, KOH or their mixtures, preferably at a temperature comprised between the room temperature and the reflux temperature of the reaction mixture.

The addition salt is generally obtained by reacting the formed acid with a base corresponding to the desired addition salt. The added base can be organic including amines, such as tert-butylamine, or inorganic bases such as NaOH, KOH, etc.

Following addition of the base, the compound of formula (I) is generally in the form of the carboxylate salt, where the counter ion is the cation resulting from the addition of a proton to the base.

The acid form of the compound of formula (I) may be recovered from its base addition salt by acidifying said salt.

The compound of formula (III) may be obtained by coupling a compound of formula (IV):

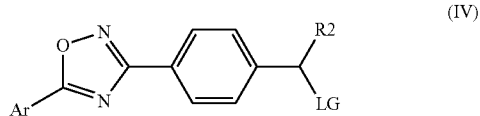

(IV)

with a corresponding compound of formula (V):

(V)

where Ar, R2, R1 are defined as in formula (I), Alk is defined as in formula (III) and LG is a leaving group such as a halogen atom, preferably Cl or the mesylate (O—SO2-CH3) group.

This reaction is generally conducted in the presence of a base. Where LG is a halogen atom, the base may be potassium carbonate to neutralize the formed acid.

When LG is mesylate the base may be organic, preferably N,N-diisopropylethylamine, triethyl amine or inorganic, preferably potassium, cesium or sodium carbonate.

Preferably, the reaction is conducted at a temperature comprised between the room temperature and the reflux temperature of the reaction mixture.

The compound of formula (IV) wherein LG is a halide or mesylate may be obtained by converting a compound of formula (VI):

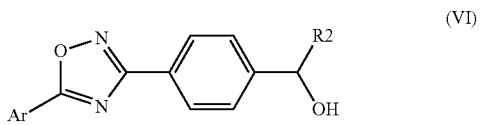

(VI)

where Ar and R2 are defined as in formula (I) into the desired halide or mesylate.

The substitution reaction may be conducted by reacting said compound of formula (VI) with usual halogenating agents such as thionyl halogenide, hydrohalogenide acid H-Hal, phosphorus trihalogenide, etc., preferably thionyl chloride. Alternatively, the mesylate derivative may be obtained by reacting said compound (VI) with mesyl chloride, in the presence of a base such as a tertiary amine, in particular triethylamine or an inorganic base, such as carbonate, hydrogenocarbonate.

According to a second embodiment, the compound of formula (I) may be obtained by reacting a compound of formula (VII):

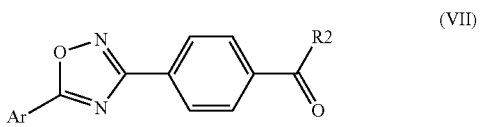

(VII)

with a compound of formula (VIII):

(VIII)

where Ar, R2, R1 are defined as in formula (I) and R may be H or alkyl, optionally followed by forming the desired addition salt.

This reaction is generally carried out in acidic medium (such as in the presence of acetic acid), followed by the addition of a reductive agent such as sodium cyanoborohydride.

If a base addition salt of the compound of formula (I) is desired, this reaction may be followed by the addition of a base, as discussed above.

The compound of formula (VII) may be obtained by oxidizing a compound of formula (VI):

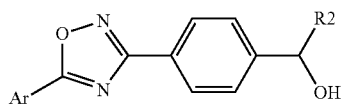
(VI)

where Ar and R2 are defined as in formula (I). This reaction may be carried out in known conditions generally used for oxidizing primary or secondary alcohol, as the case may be. In particular, this reaction may be conducted in the presence of pyridinium chlorochromate (PCC).

The compound of formula (VI) used in both embodiments above may be obtained by (a) reacting a compound of formula (IX):

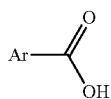
(IX)

where Ar is defined as in formula (I)
with N-hydroxy-4-hydroxymethylbenzamidine, optionally in the presence of one or more of activating and/or coupling agent, such as N,N-Dicyclohexylcarbodiimide (DCC) and N-hydroxybenzotriazole monohydrate (HOBt), so as to form a compound of formula (VI) where R2 is H, and optionally followed when a compound (VI) where R2 is alkyl is desired by (b) oxidizing the compound of formula (VI) (wherein R2 is H) followed by its reaction with alkyl magnesium halide.

The process of the invention may also include the additional step of isolating the obtained compounds.

The compounds of formula (IX), (VII), (VIII), (V) and N-hydroxy-4-hydroxymethylbenzamidine are commercially available or may be synthesized by applying or adapting known procedures.

The compounds of formula (VI):

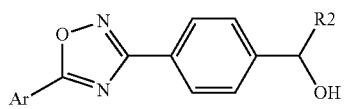
(VI)

wherein Ar and R2 are defined as in formula (II), where R2 is selected from H, alkyl and Ar represents a group of formula:

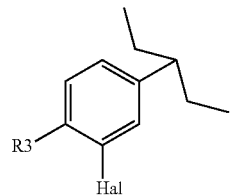
(X)

wherein Hal represents a Cl atom and R3 is selected from halogen, aryl, cycloalkyl, alkyl are novel and are another object of the present invention.

In particular, in formula (X) R3 is selected from cycloalkyl such as cyclohexyl or cyclopentyl; alkyl such as iso-butyl; or aryl such as phenyl.

The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two and such methods are within the level of a skilled person.

The present invention also relates to the isomers of the compounds of formula (I).

The isomers can be prepared by separation of the corresponding racemic compounds by methods well known in the art.

The present invention also includes esters of compound of formula (I). These may be prepared by methods well known to a person of skill in the art. For example, the esters may be prepared by the reaction of an acid with alcohol of the desired ester. For example, the compounds of formula (I) with a —COOH group may be reacted with methanol to form methyl ester of compound of formula (I). Similarly, ethyl, propyl, isobutyl and other esters can be prepared The compounds of the present invention may be useful for the treatment and/or prevention of conditions associated with S1P1/EDG1 receptor or where decrease in lymphocytes circulating in blood is desired, which include immune mediated diseases and conditions or inflammatory diseases and conditions.

The compounds of the present invention are suitable as immunosuppressive/immunodepressive agents. These compounds are suitable for the treatment and/or prevention of transplant rejection, tissue graft rejection, immune disorders auto-immune diseases, autoimmune uveitis, ischemia, inflammatory and chronic inflammatory conditions that include rheumatoid arthritis, asthma, pollinosis, psoriasis, Alzheimer's disease, myocarditis, atopic dermatitis, lymphocytic leukemias, lymphomas, sepsis, multiple sclerosis, lupus erythematosus, inflammatory bowel diseases, diabetes mellitus, glomerulonephritis, atherosclerosis, multiorgan failure, pneumonia, ischemia reperfusion injury, chronic obstructive pulmonary disease, infection associated with inflammation, viral inflammation, hepatitis, chronic bronchitis, granulomatous disease, as well as disorders related to impaired vascular integrity, cancer, or other disorders. The compounds of the present invention are generally selective EDG1 receptor agonists with very low affinity for EDG3 receptor. The selective agonism of EDG1 over EDG3 is desirable in view of the bradycardia caused by the nonselective agonism at EDG3 receptor. Also the compounds of the invention have low affinity for hERG channel due to which they exhibit a better side effect profile.

The compounds of the present invention may be used in combination with other immunomodulators or immunosuppressants including adrenocortical steroids, cyclosporine, azathioprine, methotrexate, calcineurin inhibitors, IL-2 receptor blocking antibodies, T-cell depleting antibodies, anti-TNF, mycophenolate, mTOR inhibitors. Said combinations are another object of the present invention.

A typical dose range for use according to the invention may be from 1 µg/kg to 0.1 g/kg of body weight per day; a preferred dose range may be from 3 µg/kg to 1 mg/kg of body weight per day. The most potent compounds could even be administered only two to three times per week at typical dosages of 10 to 100 µg/kg. Daily dose for adult humans includes 0.1 to 10 mg which can be optimized.

The dosage of drug to be administered depends on such variables as the type and extent of progression of the disease or disorder, the overall health status of the particular patient, the relative biological efficacy of the compound selected, and formulation of the compound, excipients, and its route of administration.

The compounds of present invention may be formulated into a pharmaceutically acceptable preparation, on admixing with a carrier, excipient or a diluent, in particular for oral or parenteral use. Certain preferred compounds display good oral bioavailability and are thus well suited for preparing formulations for oral use. Such preparations may be in the form of tablets, capsules or parenterals. A solid carrier can include one or more substances which may also act as flavoring agents, lubricants, solubilizers, suspending agents, fillers, glidants, compression aids, binders or tablet-disintegrating agents; it can also be an encapsulating material. Liquid carriers can include water, an organic solvent, a mixture of both or pharmaceutically acceptable oils and fats. The compositions may conveniently be administered in unit dosage form and may be prepared by any of the methods well known in the pharmaceutical art, for example, as described in Remington: The Science and Practice of Pharmacy, 20th ed.; Gennaro, A. R., Ed.; Lippincott Williams & Wilkins: Philadelphia, Pa., 2000. Pharmaceutically compatible binding agents and/or adjuvant materials can be included as part of the composition.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

According to a particular aspect, the compound of the invention may be administered by the cutaneous, ocular or inhalation route as disclosed above. These formulations are particularly advantageous as they ensure a local treatment, without associated lymphopenia which may occur with systemic administration routes.

Other features of the invention will become apparent in the course of the following description of exemplary embodiments that are given for illustration of the invention and not intended to be limiting thereof.

The above mentioned features of the invention are given for illustration of the invention and not intended to be limiting thereof.

PREPARATION OF INTERMEDIATES

I) Preparation of 3-chloro-4-cyclohexylbenzoic acid

Step (a)

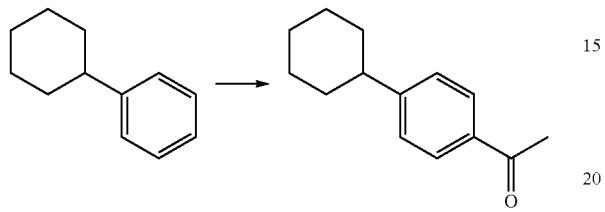

Anhydrous aluminium chloride (1.65 g, 0.012 mol) is added to a solution of cyclohexyl benzene (1 g, 0.006 mol) and acetyl chloride (0.7 mL, 0.009 mol) in dichloroethane (10 mL) at −5° C. to 0° C. temperature. The reaction mixture is stirred at this temperature for 30 minutes and then treated with 2N hydrochloric acid (7 mL). It is extracted with dichloromethane (2×20 mL) and the combined extract is dried over sodium sulfate. After removing the solvent under reduced pressure the residue is purified by column chromatography (silica gel, 230-400 mesh, ethyl acetate:n-hexane 7:93) to get 1-(4-cyclohexylphenyl)ethanone.

Step (b)

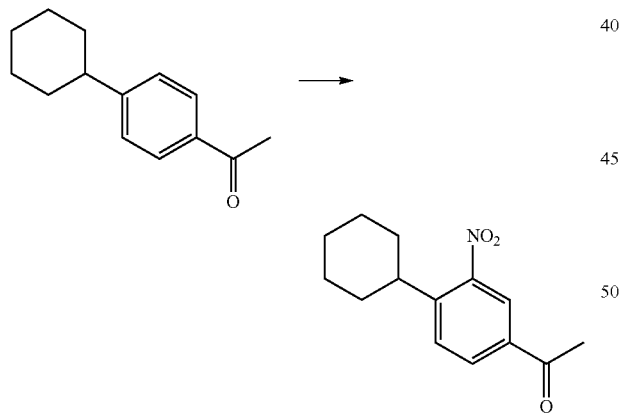

A mixture of concentrated sulfuric acid & nitric acid (68-72%) (1.7:6, 15 mL) is added drop wise to a cold solution of 1-(4-cyclohexylphenyl)ethanone (6 g, 0.03 mol) in concentrated sulfuric acid (15 mL) at 0-5° C. Reaction mixture is allowed to stir at this temperature for 30 minutes & is then poured into crushed ice. It is then extracted with ethyl acetate (3×40 mL). Combined organic layer is dried over sodium sulfate and concentrated under reduced pressure. The residue is purified by column chromatography (silica gel, 230-400 mesh, ethyl acetate:n-hexane 1:9) to yield 1-(4-cyclohexyl-3-nitrophenyl)ethanone.

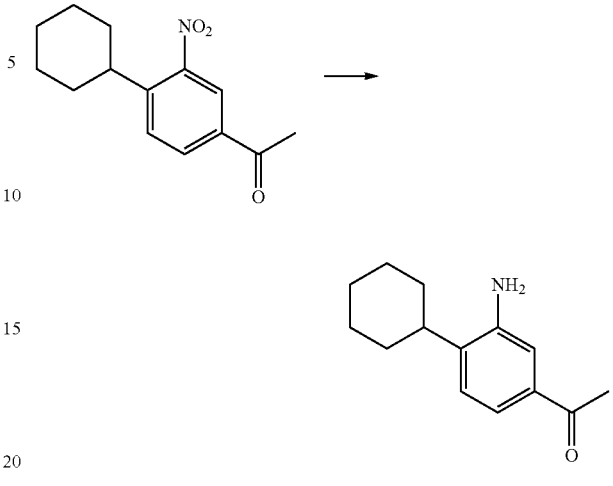

Step (c)

Stannous chloride dihydrate (15.8 g, 0.07 mol) is added to a solution of 1-(4-cyclohexyl-3-nitrophenyl)ethanone (5.8 g, 0.0235 mol) in concentrated hydrochloric acid (35 mL) at 0-5° C. The reaction mixture is slowly brought to 60-65° C. and is stirred at this temperature for 15 minutes. After cooling to room temperature the reaction mixture is extracted with ethyl acetate (3×100 mL). The pH is adjusted to 8.0-9.0 using solid sodium bicarbonate. After washing with water (1×15 mL) the organic layer is dried over sodium sulfate and concentrated under reduced pressure to yield the crude, which is purified by column chromatography (230-400 mesh; ethyl acetate:n-hexane, 3:7) to give 1-(3-amino-4-cyclohexylphenyl)ethanone.

Step (d)

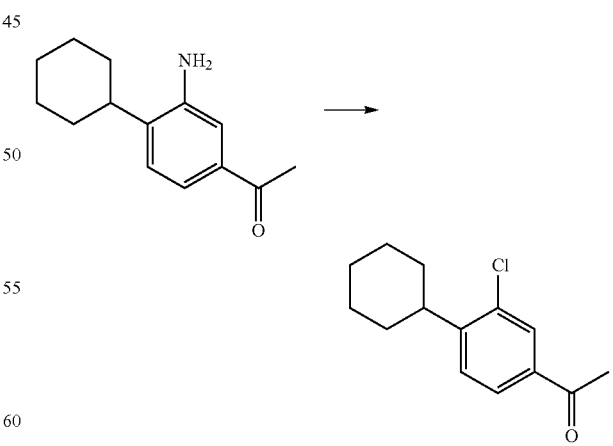

Solution of sodium nitrite (1.2 g, 0.017 mol) in demineralized water (7 mL) is added to a solution of 1-(3-amino-4-cyclohexylphenyl)ethanone (3.4 g, 0.016 mol) in concentrated hydrochloric acid (34 mL) at 0-5° C. & is allowed to stir for 15 minutes at this temperature. It is then poured into a slurry of cuprous chloride (3.1 g, 0.03 mol) in demineralized water (10 mL) at 60-65° C. & stirred for 30 minutes. The reaction mixture is extracted in ethyl acetate (2×30 mL). Combined organic layer is dried over sodium sulfate and concentrated to get the crude, which is purified using column chromatography (230-400 mesh; toluene:n-hexane, 3:2) to yield 1-(3-chloro-4-cyclohexyl-phenyl)ethanone.

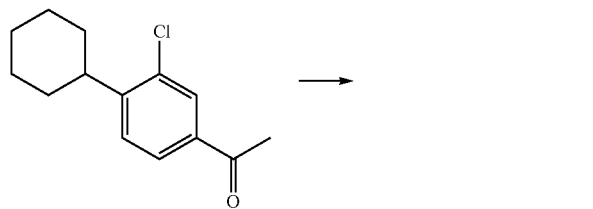

Step (e)

An aqueous alkaline solution of potassium permanganate (2.94 g, 0.0186 mol; in 22 mL 12% aqueous sodium hydroxide) is added to solution of 1-(3-chloro-4-cyclohexylphenyl) ethanone (2.2 g, 0.0093 mol) in dioxane (11 mL). The reaction mixture is stirred at 80° C. temperature for 2 hrs. It is then filtered and the filtrate is washed with diethyl ether (2×10 mL). The pH of the aqueous layer is adjusted to 1-2 by using 6N hydrochloric acid. It is extracted in ethyl acetate (3×15 mL). Combined organic layer is dried over sodium sulfate and concentrated to get the crude, which is purified using column chromatography (230-400 mesh; ethyl acetate:n-hexane, 1:3) to yield 3-chloro-4-cyclohexyl benzoic acid.

II) Preparation of 3-chloro-4-cyclopentylbenzoic acid

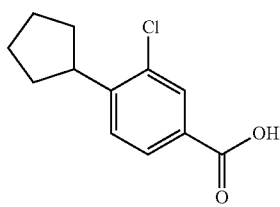 [SMILES: O=C(O)c1ccc(C2CCCC2)c(Cl)c1]

This compound is prepared in the same way as mentioned for 3-chloro-4-cyclohexyl benzoic acid (I).

III) Preparation of 3-chloro-4-isobutylbenzoic acid

Step (a)

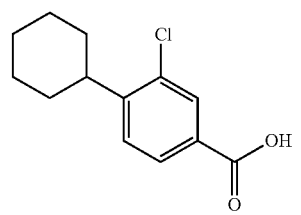

4-Isobutyl benzaldehyde (7 g, 0.0431 mol) is added drop wise to a mixture of concentrated sulfuric acid & nitric acid (68-72%) (9:1, 60 mL) at 0-5° C. Reaction mixture is allowed to stir at this temperature for 2 hrs, then poured into crushed ice. It is then extracted with ethyl acetate (3×40 mL). Combined organic layer is dried over sodium sulfate and concentrated under reduced pressure. The residue is purified by column chromatography (silica gel, 230-400 mesh, ethyl acetate:n-hexane 1:19) to yield 4-isobutyl-3-nitrobenzaldehyde.

Step (b)

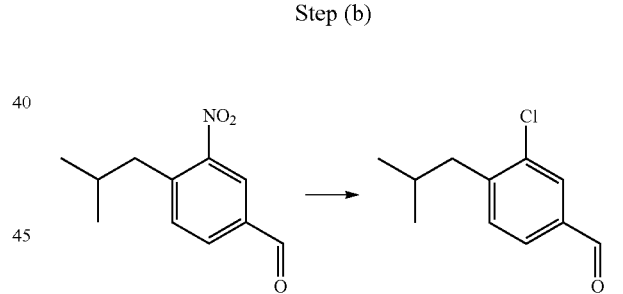

4-Isobutyl-3-nitrobenzaldehyde (3.3 g, 0.0159 mol) is added to a solution of stannous chloride (8.37 g, 0.0441 mol) in concentrated hydrochloric acid (23 mL) at 0-5° C. The reaction mixture is slowly brought to 60-65° C. and is stirred at this temperature for 30 minutes. The reaction mixture is again cooled to 0-5° C. During cooling formation of solid is observed which is broken before proceeding further. Solution of sodium nitrite (1.36 g, 0.0188 mol) in demineralized water (3 mL) is added to the above reaction mixture at 0-5° C., allowed to stir for 10 minutes at this temperature. It is then poured into a slurry of cuprous chloride (3.6 g, 0.0346 mol) in demineralized water (5 mL) at 60-65° C. & stirred for 20 minutes. The reaction mixture is extracted in ethyl acetate (2×30 mL). Combined organic layer is dried over sodium sulfate and concentrated to get the crude, which is purified using column chromatography (230-400 mesh; toluene:n-hexane, 3:7) to yield 3-chloro-4-isobutylbenzaldehyde.

Step (c)

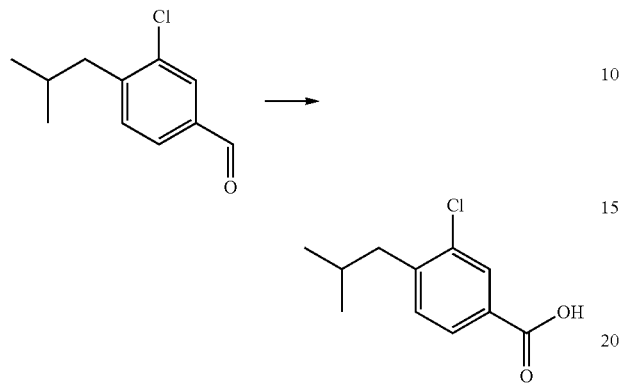

A mixture of sodium chlorite (80% assay, 1.06 g, 0.0094 mol) and sodium dihydrogenphosphate dihydrate (3.33 g, 0.0213 mol) in demineralized water (10 mL) is added in two equal lots (one hr interval) to a solution of 3-chloro-4-isobutylbenzaldehyde (0.7 g, 0.0036 mol) in tert-butanol (10 mL) at room temperature. After completion of addition, stirring at room temperature is continued for 4 hrs. It is then extracted in ethyl acetate (2×30 mL). Combined organic layer is dried over sodium sulfate and concentrated under reduced pressure to give 3-chloro-4-isobutylbenzoic acid.

IV) Preparation of 2-chlorobiphenyl-4-carboxylic acid

Step (a)

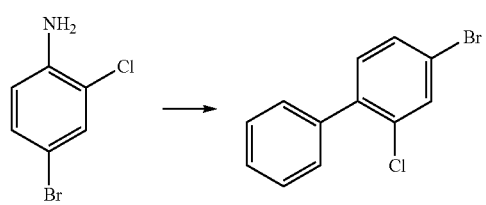 [SMILES: Nc1ccc(Br)cc1Cl ; Clc1cc(Br)ccc1-c1ccccc1]

Isobutyl nitrite (121 g, 1.17 mol) and cupric chloride (21.2 g, 0.16 mol) are added to a solution of 4-bromo-2-chloroaniline (200 g, 0.97 mol) in benzene (500 mL) at 60-65° C. temperature. The reaction mixture is refluxed for 2 hrs. The reaction mixture is cooled to 50-55° C. temperature and to it a solution of aqueous sulfuric acid (92 mL conc. Sulfuric acid in 453 mL demineralized water). After refluxing for 1 hr the reaction mixture is cooled to room temperature and organic layer is separated. It is treated with an aqueous solution of urea (41 g in 127 mL water) and refluxed for 1 hr. Organic layer is separated, washed with demineralized water (2×200 mL) and dried over sodium sulfate. After removing the solvent under reduced pressure the residue is fractionally distilled to get 4-bromo-2-chlorobiphenyl.

Step (b)

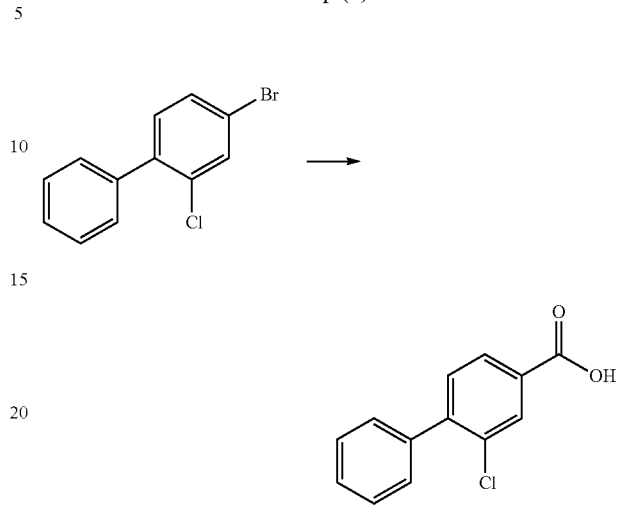

Few crystals of iodine are added to tetrahydrofuran (200 mL) containing magnesium turnings (2.8 g, 0.117 mol). The mixture is heated at 60-70° C. A solution of 4-bromo-2-chlorobiphenyl (26 g, 0.097 mol) in tetrahydrofuran (50 mL) is added dropwise to the reaction mixture and refluxed for 1 hr. Reaction mixture is brought to room temperature and then cooled to −20° C. Carbon dioxide gas is passed through the reaction mixture for 45 minutes. The reaction mixture is treated with 3N HCl (125 mL) and extracted with ethyl acetate (2×200 mL). Combined organic layer is dried over sodium sulphate. Removal of solvent under reduced pressure gives a solid which is washed with diethyl ether (2×100 mL) and then dried to furnish 2-chlorobiphenyl-4-carboxylic acid.

V) Preparation of 4-methylpiperidine-4-carboxylic acid ethyl ester

Step (a)

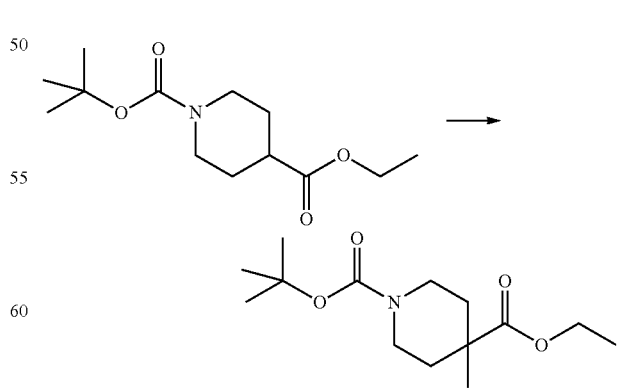

n-Butyllithium (15% solution in n-hexane; 82 mL, 0.19 mol) is added to a stirred solution of diisopropyl amine (28.75 mL, 0.20 mol) in tetrahydrofuran (400 mL) at −70° C. under an atmosphere of nitrogen and stirred for 30 minutes. A solution of piperidine-1,4-dicarboxylic acid-1-tert-butyl ester 4-ethyl ester (30 g, 0.12 mol) in tetrahydrofuran (80 mL) is introduced at −70° C. Hexamethyl phosphoramide (45 mL) is added and reaction mixture is allowed to stir till the temperature reaches at −45° C. Reaction mixture again cooled to −70° C., methyl iodide (39.3 mL, 0.60 mol) is added and stirred for 1 hour. Saturated aqueous solution of ammonium chloride (100 mL) is added slowly into the reaction mixture at 0° C. and stirred for 10 minutes. It is extracted with ethyl acetate (3×200 mL). Combined organic layer is washed with brine solution (1×100 mL) and dried over sodium sulfate. Removal of solvent under reduced pressure gives a viscous liquid which is purified by column chromatography (silica gel 230-400, n-hexane:ethyl acetate, 9:1) to furnish 4-methyl piperidine-1,4-dicarboxylic acid-1-tert-butylester-4-ethyl ester.

Step (b)

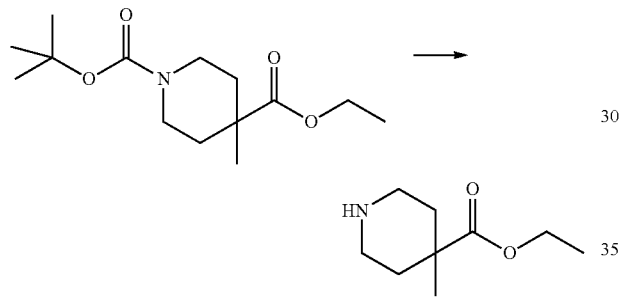

A solution of hydrochloric acid (12N, 12.5 mL) in dioxane (25 mL) is added to 4-methyl piperidine-1,4-dicarboxylic acid-1-tert-butyl ester-4-ethyl ester (7.5 g, 0.028 mol) and stirred at room temperature for 1 hr. The reaction mixture is concentrated under reduced pressure and the residue is treated with aqueous solution of sodium bicarbonate to adjust the pH to 8-9. It is again concentrated under reduced pressure and the residue is treated with dichloromethane. After drying over sodium sulfate solvent is removed to get the crude residue which is purified by column chromatography (silica gel 230-400 mesh, methanol:dichloromethane:ammonium hydroxide 14:85:1) to get 4-methylpiperidine-4-carboxylic acid ethyl ester.

Following compounds, VI to XIV (except IX), can be prepared by following a process similar to compound V.

VI) 4-Ethylpiperidine-4-carboxylic acid ethyl ester

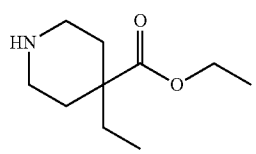

VII) 4-(2-Methoxyethoxymethyl)piperidine-4-carboxylic acid ethyl ester

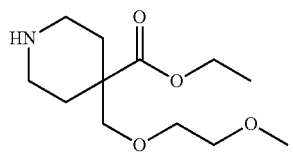 [SMILES: CCOC(=O)C1(COCCOC)CCNCC1]

VIII) 4-Methoxymethylpiperidine-4-carboxylic acid ethyl ester

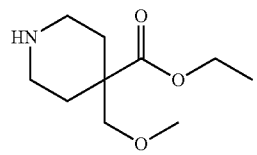

IX) 4-Phenyl-piperidine-4-carboxylic acid ethyl ester

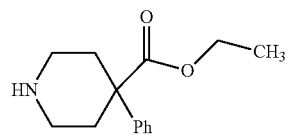

This material is commercially available.

X) 4-Benzyl-piperidine-4-carboxylic acid ethyl ester

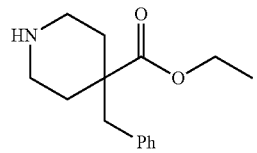

XI) 4-(4-Fluoro-benzyl)-piperidine-4-carboxylic acid ethyl ester

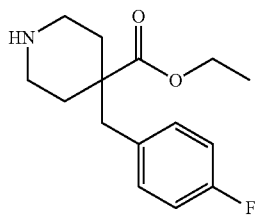 [SMILES: CCOC(=O)C1(Cc2ccc(F)cc2)CCNCC1]

XII) 4-(2-Fluoro-benzyl)-piperidine-4-carboxylic acid ethyl ester

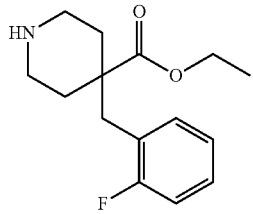 [SMILES: CCOC(=O)C1(Cc2ccccc2F)CCNCC1]

XIII) 4-(4-Methoxy-benzyl)-piperidine-4-carboxylic acid ethyl ester

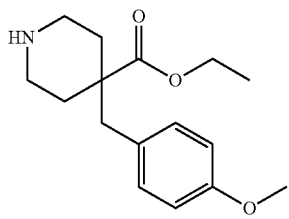 [SMILES: CCOC(=O)C1(Cc2ccc(OC)cc2)CCNCC1]

XIV) 4-(2-Methoxy-benzyl)-piperidine-4-carboxylic acid ethyl ester

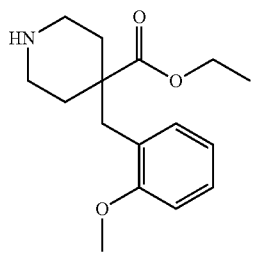 [SMILES: CCOC(=O)C1(Cc2ccccc2OC)CCNCC1]

XV) Preparation of 4-allylpiperidine-4-carboxylic acid ethyl ester

Step (a)

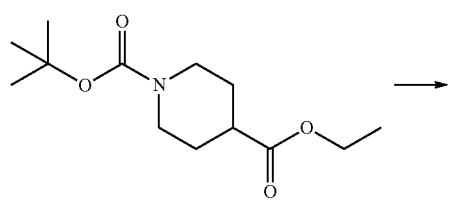

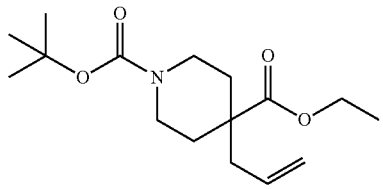

n-Butyllithium (15% solution in n-hexane; 24.5 mL, 0.057 mol) is added to a stirred solution of diisopropyl amine (8.38 mL, 0.059 mol) in tetrahydrofuran (140 mL) at −70° C. under an atmosphere of nitrogen and stirred for 30 minutes. A solution of piperidine-1,4-dicarboxylic acid-1-tert-butyl ester-4-ethyl ester (8.0 g, 0.0311 mol) in tetrahydrofuran (20 mL) is introduced at −70° C. Hexamethyl phosphoramide (15 mL) is added and reaction mixture is allowed to stir till the temperature reaches at −45° C. Reaction mixture again cooled to −70° C., allyl bromide (13.5 mL, 0.155 mol) is added and stirred for 1 hour. Saturated aqueous solution of ammonium chloride (100 mL) is added slowly into the reaction mixture at −30° C. and stirred for 10 minutes. It is extracted with ethyl acetate (3×60 mL). Combined organic layer is washed with brine solution (1×30 mL) and dried over sodium sulfate. Removal of solvent under reduced pressure gives a viscous liquid which is purified by column chromatography (silica gel 230-400, n-hexane:ethyl acetate, 9:1) to furnish 4-allyl piperidine-1,4-dicarboxylic acid-1-tert-butylester-4-ethyl ester.

Step (b)

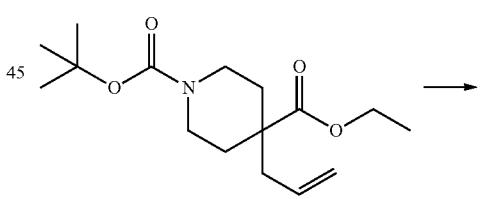

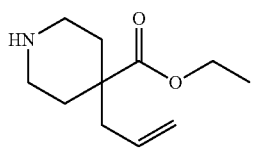

A solution of hydrochloric acid (12N, 4 mL) in dioxane (6 mL) is added to 4-allyl piperidine-1,4-dicarboxylic acid-1-tert-butyl ester-4-ethyl ester (2 g, 0.006 mol) and stirred at room temperature for 30 minutes. The reaction mixture is concentrated under reduced pressure and the residue is treated with aqueous solution of sodium bicarbonate to adjust the pH to 8-9. It is again concentrated under reduced pressure and the residue is treated with dichloromethane. After drying over sodium sulfate solvent is removed to get 4-allylpiperidine-4-carboxylic acid ethyl ester.

XVI) Preparation of 4-propylpiperidine-4-carboxylic acid ethyl ester

Step (a)

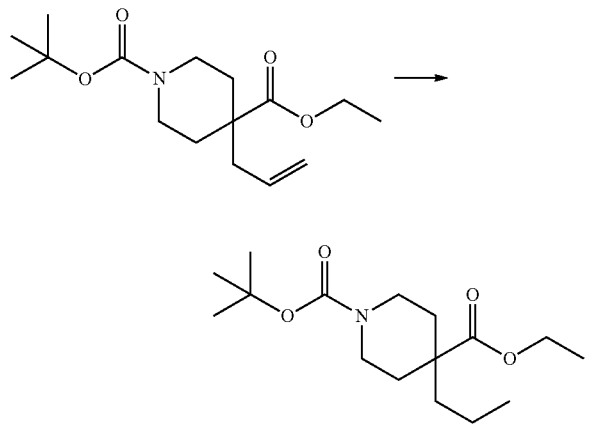

5% Pd/C (0.6 g, 50% wet) is added to a stirred solution of 4-allylpiperidine-1,4-dicarboxylicacid-1-tert-butylester-4-ethyl ester (2.1 g, 0.007 mol) in ethanol (20 mL). Hydrogen gas is bubbled through the reaction mixture at room temperature for 20 minutes. Reaction mixture is filtered through celite bed and washed with methanol (3×5 mL). Combined filtrate is concentrated under reduced pressure to give 4-propylpiperidine-1,4-dicarboxylic acid-1-tert-butyl ester-4-ethyl ester.

Step (b)

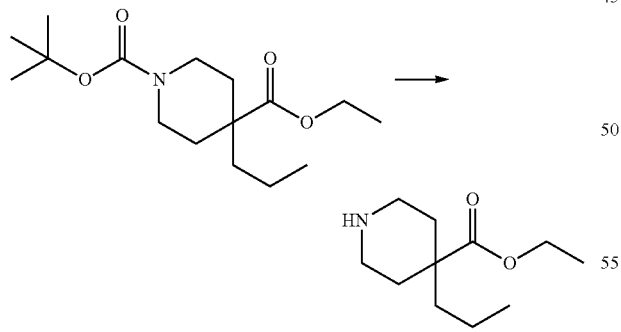

A solution of hydrochloric acid (12N, 4.2 mL) in dioxane (6.8 mL) is added to 4-propylpiperidine-1,4-dicarboxylic acid-1-tert-butyl ester-4-ethyl ester (2.2 g, 0.0073 mol) and stirred at room temperature for 30 minutes. The reaction mixture is concentrated under reduced pressure and the residue is treated with aqueous solution of sodium bicarbonate to adjust the pH to 8-9. It is again concentrated under reduced pressure and the residue is treated with dichloromethane. After drying over sodium sulfate solvent is removed to get 4-propylpiperidine-4-carboxylic acid ethyl ester.

XVII) Preparation of 4-benzyloxymethyl-piperidine-4-carboxylic acid ethyl ester Step (a)

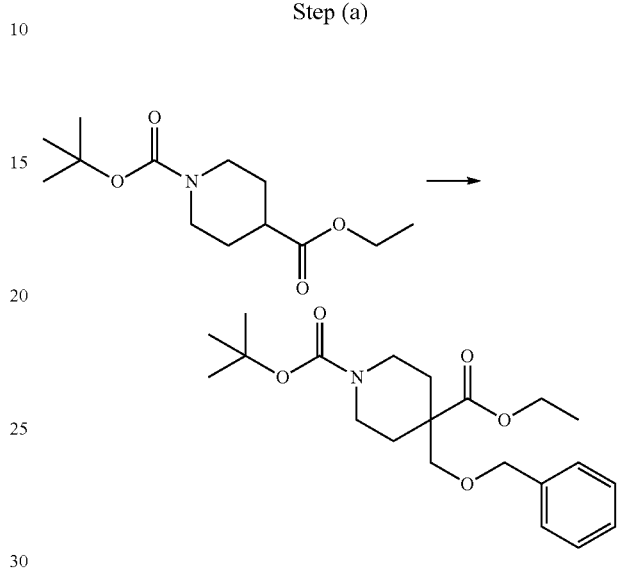

n-Butyllithium (15% solution in n-hexane; 9.5 mL, 0.022 mol) is added to a stirred solution of diisopropyl amine (3.1 mL, 0.022 mol) in tetrahydrofuran (15 mL) at −70° C. under an atmosphere of nitrogen and stirred for 30 minutes. A solution of piperidine-1,4-dicarboxylic acid-1-tert butyl ester-4-ethyl ester (3 g, 0.012 mol) in tetrahydrofuran (10 mL) is introduced at −70° C. Hexamethyl phosphoramide (4.8 mL) is added and reaction mixture is allowed to stir till the temperature reaches at −45° C. Reaction mixture again cooled to −70° C., benzyl chloromethyl ether (5 mL, 0.035 mol) is added and stirred for 1 hour. Saturated aqueous solution of ammonium chloride (30 mL) is added slowly into the reaction mixture at −30° C. and stirred for 10 minutes. It is extracted with ethyl acetate (2×20 mL). Combined organic layer is dried over sodium sulfate. Removal of solvent under reduced pressure gives a viscous liquid which is purified by column chromatography (silica gel 230-400, toluene:ethyl acetate, 23:2 to furnish 4-benzyloxymethylpiperidine-1,4-dicarboxylic acid-1-tert butyl ester-4-ethyl ester.

Step (b)

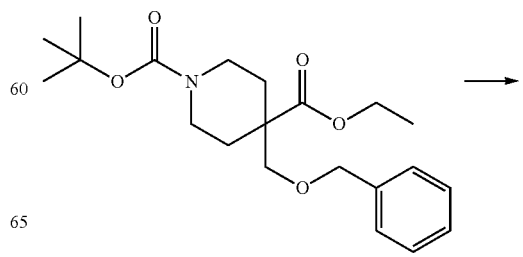

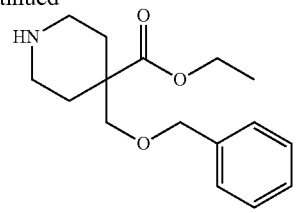

A solution of hydrochloric acid (12N, 1.5 mL) in dioxane (7.5 mL) is added to 4-benzyloxymethylpiperidine-1,4-dicarboxylic acid-1-tert butyl ester-4-ethyl ester (1.9 g, 0.005 mol) and stirred at room temperature for 30 minutes. The reaction mixture is concentrated under reduced pressure and the residue is treated with aqueous solution of sodium bicarbonate to adjust the pH to 8-9. It is again concentrated under reduced pressure and the residue is treated with dichloromethane. After drying over sodium sulfate solvent is removed to get 4-benzyloxymethylpiperidine-4-carboxylic acid ethyl ester.

XVIII) Preparation of 4-hydroxymethylpiperidine-4-carboxylic acid ethyl ester

Step (a)

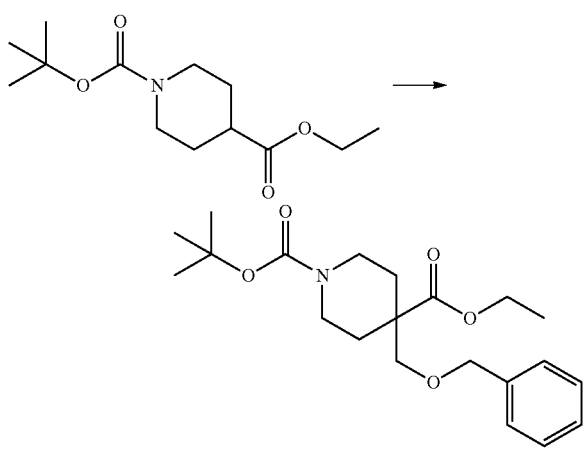

n-Butyllithium (15% solution in n-hexane; 9.5 mL, 0.022 mol) is added to a stirred solution of diisopropyl amine (3.1 mL, 0.022 mol) in tetrahydrofuran (15 mL) at −70° C. under an atmosphere of nitrogen and stirred for 30 minutes. A solution of piperidine-1,4-dicarboxylic acid-1-tert-butyl ester-4-ethyl ester (3 g, 0.012 mol) in tetrahydrofuran (10 mL) is introduced at −70° C. Hexamethyl phosphoramide (4.8 mL) is added and reaction mixture is allowed to stir till the temperature reaches at −45° C. Reaction mixture again cooled to −70° C., benzyl chloromethyl ether (5 mL, 0.035 mol) is added and stirred for 1 hour. Saturated aqueous solution of ammonium chloride (30 mL) is added slowly into the reaction mixture at −30° C. and stirred for 10 minutes. It is extracted with ethyl acetate (2×20 mL). Combined organic layer is dried over sodium sulfate. Removal of solvent under reduced pressure gives a viscous liquid which is purified by column chromatography (silica gel 230-400, toluene:ethyl acetate, 23:2 to furnish 4-benzyloxymethylpiperidine-1,4-dicarboxylic acid-1-tert-butyl ester-4-ethyl ester.

Step (b)

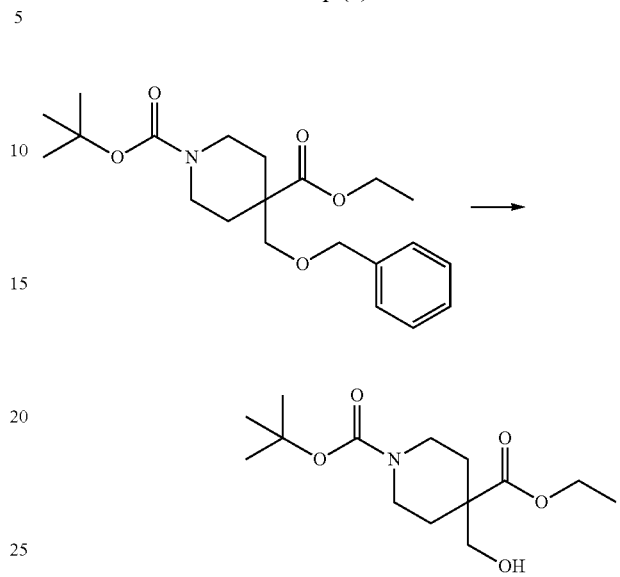

5% Pd/C (1.85 g, 50% wet) is added to a solution of 4-benzyloxymethylpiperidine-1,4-dicarboxylic acid-1-tert-butyl ester-4-ethyl ester (1.85 g, 0.0049 mol) in ethanol (20 mL). The reaction mixture is stirred under the positive pressure of hydrogen gas for 16 hrs at room temperature. The reaction mixture is filtered through celite bed and washed with a solution methanol and dichloromethane (1:5, 100 mL). Combine filtrate is concentrated under reduced pressure to give 4-hydroxymethylpiperidine-1,4-dicarboxylic acid 1-tert-butyl ester-4-ethyl ester.

Step (c)

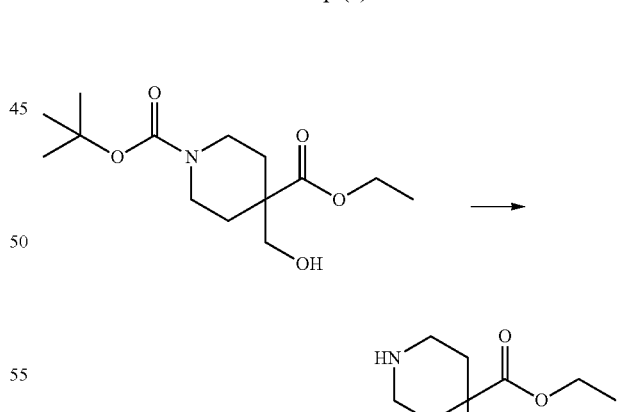

A solution of hydrochloric acid (12N, 2.5 mL) in dioxane (4.5 mL) is added to 4-hydroxymethylpiperidine-1,4-dicarboxylic acid-1-tert-butyl ester-4-ethyl ester (1.35 g, 0.0047 mol) and stirred at room temperature for 30 minutes. The reaction mixture is concentrated under reduced pressure and the residue is treated with aqueous solution of sodium bicarbonate to adjust the pH to 8-9. It is again concentrated under reduced pressure and the residue is treated with dichloromethane. After drying over sodium sulfate solvent is removed to get 4-hydroxymethylpiperidine-4-carboxylic acid ethyl ester.

Following intermediates XIX to XXIX can be prepared following the same procedure as that of intermediate V XIX) 4-(4-Methoxy-butyl)-piperidine-4-carboxylic acid ethyl ester

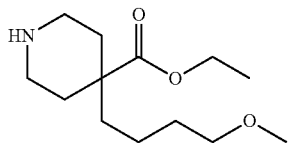 [SMILES: CCOC(=O)C1(CCCCOC)CCNCC1]

XX) 4-(2-Phenoxy-ethyl)-piperidine-4-carboxylic acid ethyl ester

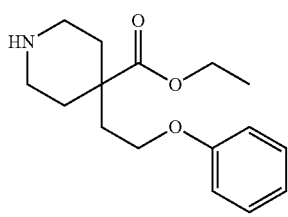 [SMILES: CCOC(=O)C1(CCOc2ccccc2)CCNCC1]

XXI) 4-(2,6-Difluoro-benzyl)-piperidine-4-carboxylic acid ethyl ester

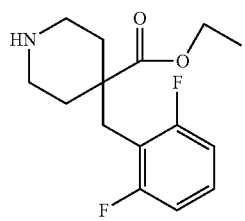 [SMILES: CCOC(=O)C1(Cc2c(F)cccc2F)CCNCC1]

XXII) 4-Pyridin-2-ylmethyl-piperidine-4-carboxylic acid ethyl ester

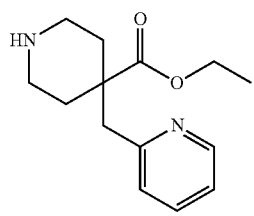 [SMILES: CCOC(=O)C1(Cc2ccccn2)CCNCC1]

XXIII) 4-[2-(2-Methoxy-phenoxy)-ethyl]-piperidine-4-carboxylic acid ethyl ester

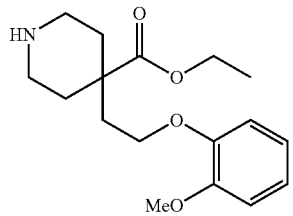 [SMILES: CCOC(=O)C1(CCOc2ccccc2OC)CCNCC1]

XXIV) 4-(4-Methyl-benzyl)-piperidine-4-carboxylic acid ethyl ester

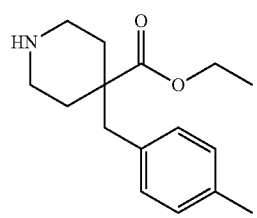 [SMILES: CCOC(=O)C1(Cc2ccc(C)cc2)CCNCC1]

XXV) 4-Pyridin-3-ylmethyl-piperidine-4-carboxylic acid ethyl ester

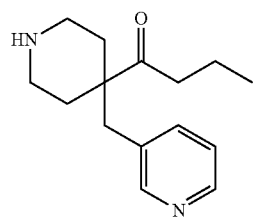 [SMILES: CCCC(=O)C1(Cc2cccnc2)CCNCC1]

XXVI) 4-Pyridin-4-ylmethyl-piperidine-4-carboxylic acid ethyl ester

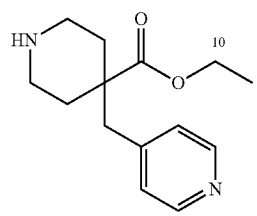 [SMILES: CCOC(=O)C1(Cc2ccncc2)CCNCC1]

XXVII) 4-Isopropoxymethyl-piperidine-4-carboxylic acid ethyl ester

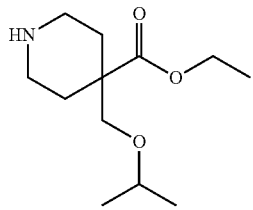 [SMILES: CCOC(=O)C1(COC(C)C)CCNCC1]

XXVIII) 4-Cyclopentyloxymethyl-piperidine-4-carboxylic acid ethyl ester

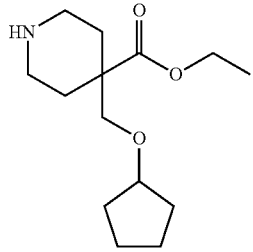 [SMILES: CCOC(=O)C1(COC2CCCC2)CCNCC1]

XXIX) 4-(2-Morpholin-4-yl-ethyl)-piperidine-4-carboxylic acid ethyl ester

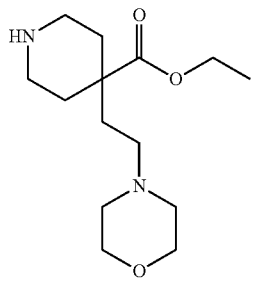 [SMILES: CCOC(=O)C1(CCN2CCOCC2)CCNCC1]

XXX) 4-Isobutylpiperidine-4-carboxylic acid

Step (a)

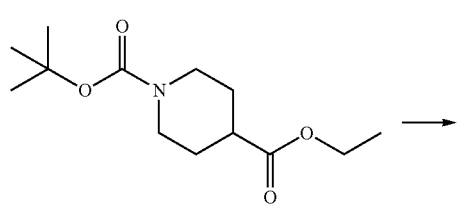

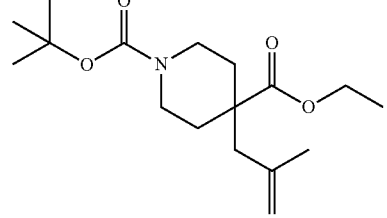

This compound is prepared by following a process same as that of 4-methylpiperidine-1,4-dicarboxylic acid-1-tert-butyl ester-4-ethyl ester [step (a) of intermediate V]

Step (b)

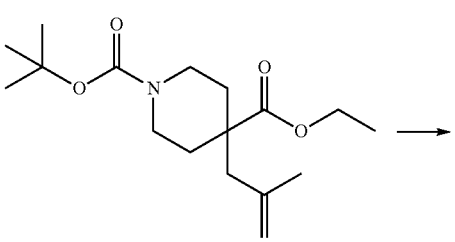

5% Pd/C (0.3 g, 50% wet) is added to a solution of 4-(2-methylallyl)piperidine-1,4-dicarboxylic acid-1-tert-butyl ester-4-ethyl ester (1.0 g, 0.0032 mol) in ethanol (10 mL). The reaction mixture is stirred under the positive pressure of hydrogen gas for 1 hr at room temperature. The reaction mixture is filtered through celite bed and washed with ethanol (15 mL). Combine filtrate is concentrated under reduced pressure to get 4-isobutylpiperidine-1,4-dicarboxylic acid-1-tert-butyl ester-4-ethyl ester.

Step (c)

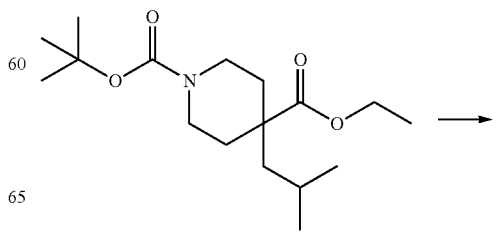

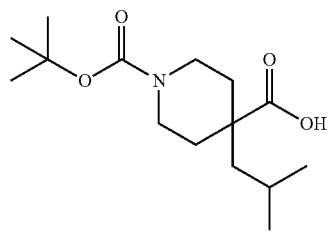

A solution of potassium hydroxide (85% assay, 2.69 g, 0.041 mol) and sodium hydroxide (1.94 g, 0.048 mol) in demineralized water (8 mL) is added to a solution of 4-isobutylpiperidine-1,4-dicarboxylic acid-1-tertbutyl ester-4-ethyl ester (0.95 g, 0.003 mol) in ethanol (15 mL). The reaction mixture is refluxed for 48 hrs. It is cooled to room temperature, concentrated under reduced pressure, and then treated with demineralized water (10 mL). The pH is adjusted to ~3-4 using 2N HCl (10 mL) and the aqueous layer is extracted with ethyl acetate (2×15 mL). The combined extract is dried over sodium sulfate. Removal of solvent gives a crude residue which is purified by column chromatography (230-400 mesh, ethyl acetate:n-hexane 1:3) to furnish 4-isobutylpiperidine-1,4-dicarboxylic acid monotertbutyl ester.

Step (d)

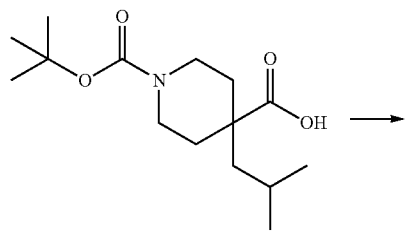

A solution of hydrochloric acid (12N, 1.2 mL) in 1,4-dioxane (2.4 mL) is added to 4-isobutylpiperidine-1,4-dicarboxylic acid monotertbutyl ester (0.7 g, 0.0025 mol) and stirred at room temperature for 1 hr. The reaction mixture is concentrated under reduced pressure and the residue is treated with saturated solution of sodium bicarbonate (0.5 mL) to adjust the pH to ~7. It is again concentrate under reduced pressure to get crude 4-isobutylpiperidine-4-carboxylic acid.

XXXI)
4-Cyclopropylmethyl-piperidine-4-carboxylic acid

Step (a)

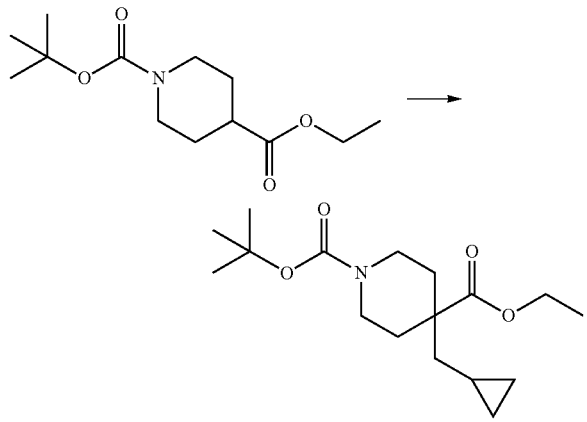

This compound is prepared following the same procedure as that of 4-methylpiperidine-1,4-dicarboxylic acid-1-tert-butyl ester-4-ethyl ester [step (a) of intermediate V].

Step (b)

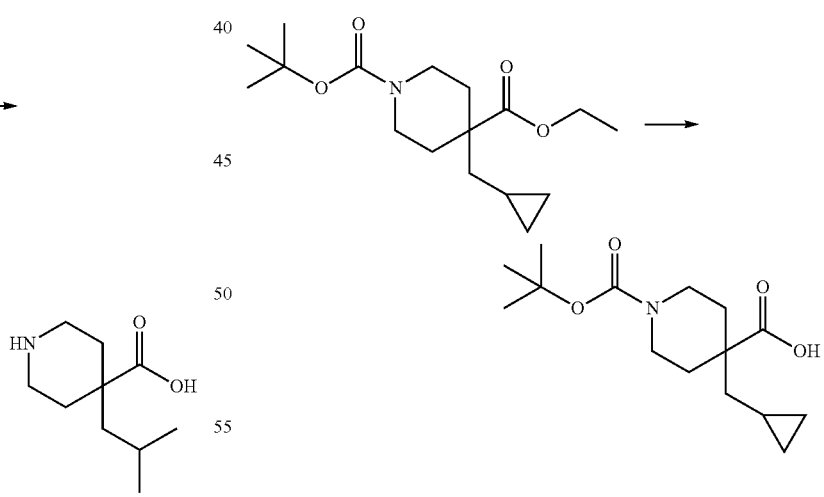

Potassium hydroxide powder (85% assay, 2.16 gm, 0.0327 mol) and 18-crown-6 ether (350 mg) are added to a solution of 4-cyclopropylmethylpiperidine-1,4-dicarboxylic acid-1-tert-butyl ester-4-ethyl ester (1.2 gm, 0.0039 mol) in dry toluene (15 mL). The reaction mixture is refluxed for 30 minutes. It is then treated with demineralized water (15 mL) at room temperature and pH is adjusted to ~3-4 using 2N HCl (20 mL). The aqueous layer is extracted with ethyl acetate (2×15 mL) and the combined extract is dried over sodium sulfate.

Removal of solvent gives 4-cyclopropylmethylpiperidine-1,4-dicarboxylic acid monotertbutyl ester.

Step (c)

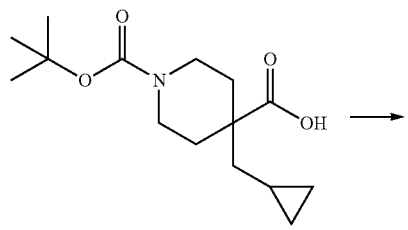

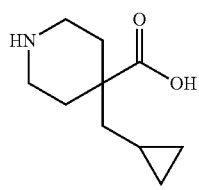

This intermediate is prepared following the same procedure as that of 4-isobutylpiperidine-4-carboxylic acid [step (d) of intermediate XXX].

XXXII) 4-Isopropyl-piperidine-4-carboxylic acid

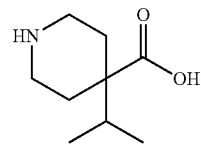

This intermediate is prepared following the same procedure as that of 4-cyclopropylmethyl-piperidine-4-carboxylic acid (XXXI).

XXXIII) 4-Thiophen-2-ylmethylpiperidine-4-carboxylic acid ethyl ester

Step (a)

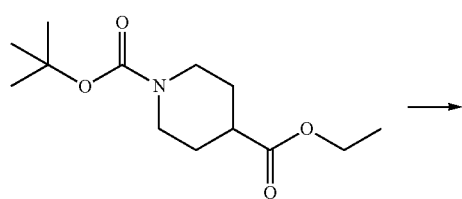

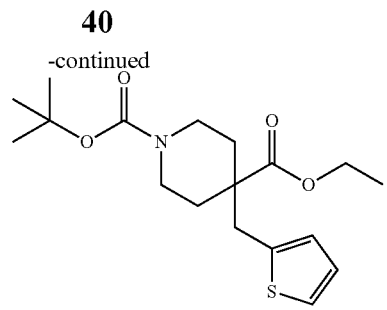

Methanesulphonyl chloride (6.2 mL, 0.0797 mol) is added dropwise to a solution of thiophene-2-methanol (7.0 g, 0.0613 mol) and triethyl amine (12.8 mL, 0.0920 mol) in dichloromethane (70 mL) at 0-5° C. The reaction mixture is allowed to stir at room temperature for 30 min. Demineralized water (25 mL) is added to the reaction mixture and the organic layer is separated. The aqueous layer is extracted with dichloromethane (1×25 mL). Combined organic layer is dried over anhydrous sodium sulfate. Removal of solvent under reduced pressure gives methanesulfonic acid thiophen-2-yl-methyl ester.

n-Butyllithium (15% solution in n-hexane; 10 mL, 0.023 mol) is added to a stirred solution of diisopropyl amine (3.5 mL, 0.025 mol) in tetrahydrofuran (25 mL) at −70° C. under an atmosphere of nitrogen and stirred for 30 minutes. A solution of piperdine-1,4-dicarboxylic acid-1-tert-butyl ester-4-ethyl ester (3 gm, 0.012 mol) in tetrahydrofuran (10 mL) is introduced at −70° C. Hexamethyl phospharamide (4.8 mL) is added and reaction mixture is allowed to stir till the temperature reaches at −45° C. Reaction mixture is again cooled to −70° C., methanesulfonic acid thiophen-2-ylmethyl ester (5.8 gm, 0.030 mol) in tetrahydrofuran (10 mL) is added and stirred for 45 minutes. Demineralized water (15 mL) is added slowly into the reaction mixture at 0° C. and stirred for 10 minutes. It is extracted with ethyl acetate (2×15 mL). Combined organic layer is dried over sodium sulfate. Removal of solvent under reduced pressure gives a crude residue which is purified by column chromatography (230-400 mesh, ethyl acetate:n-hexane 15:85) to furnish 4-thiophen-2-ylmethylpiperidine-1,4-dicarboxylic acid-1-tert-butyl ester-4-ethyl ester.

Step (b)

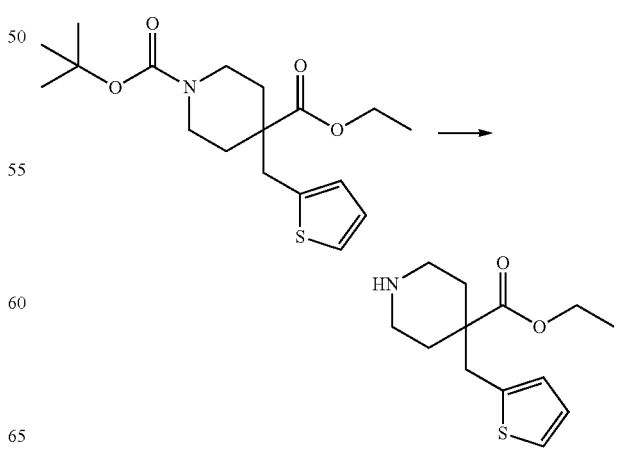

This intermediate is prepared by following the same procedure as that of 4-methylpiperidine-4-carboxylic acid ethyl ester [step (b) of intermediate V].

XXXIV) 4-Furan-2-ylmethyl-piperidine-4-carboxylic acid ethyl ester

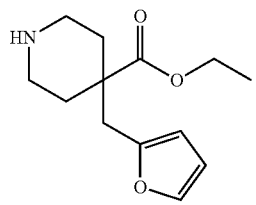 [SMILES: CCOC(=O)C1(Cc2ccco2)CCNCC1]

This intermediate is prepared following the same procedure as that of 4-thiophen-2-ylmethylpiperidine-4-carboxylic acid ethyl ester (XXXIII).

XXXV) 4-(3-Piperidin-1-yl-propyl)-piperidine-4-carboxylic acid ethyl ester

Step (a)

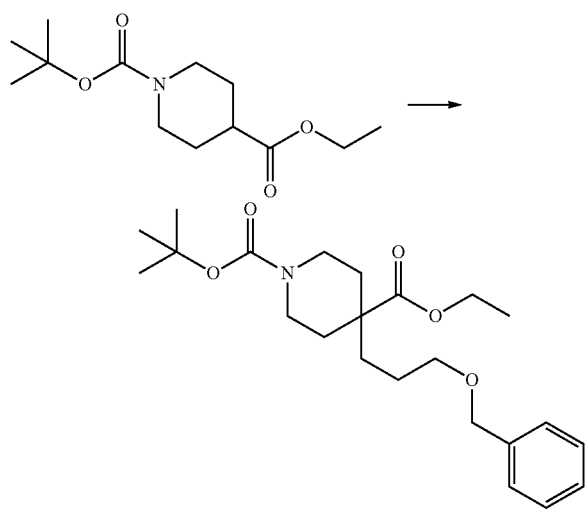

This compound is prepared following the same procedure as that of 4-benzyloxymethylpiperidine-1,4-dicarboxylic acid-1-tert-butyl ester-4-ethyl ester [step (a) of intermediate (XVIII)].

Step (b)

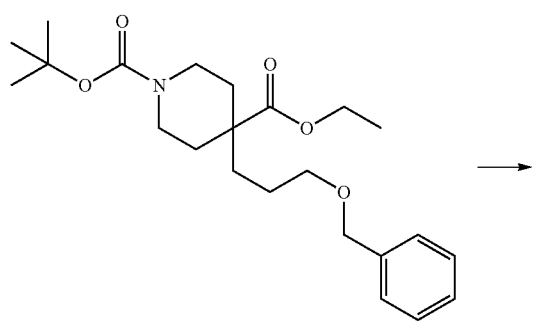

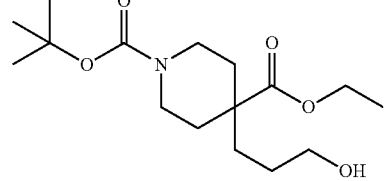

This compound is prepared following the same procedure as that of 4-hydroxymethylpiperidine-1,4-dicarboxylic acid 1-tert-butyl ester-4-ethyl ester [step (b) of intermediate (XVIII)].

Step (c)

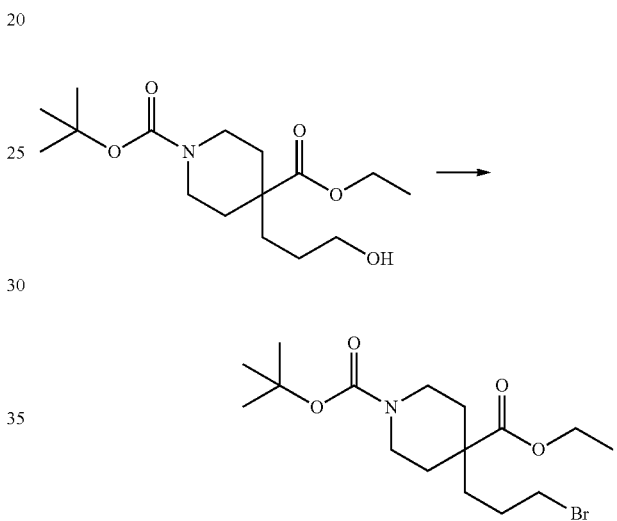

Carbon tetrabromide (1.6 gm, 0.0048 mol) is added to a stirred solution of 4-(3-hydroxypropyl) piperidine-1,4-dicarboxylic acid-1-tert-butyl ester-4-ethyl ester (1.27 gm, 0.0040 mol) and triphenyl phosphine (1.6 gm, 0.0060 mol) in dichloromethane (15 mL) at 0-5° C. temperature. Reaction mixture is allowed to stir at room temperature for 30 minutes. Removal of solvent gives a crude residue which is purified by column chromatography (silica gel 230-400 mesh, ethyl acetate:n-hexane 3:7) to get 4-(3-bromopropyl)piperidine-1,4-dicarboxylic acid-1-tert-butyl ester-4-ethyl ester.

Step (d)

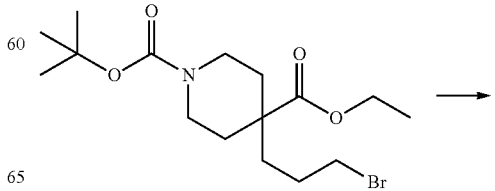

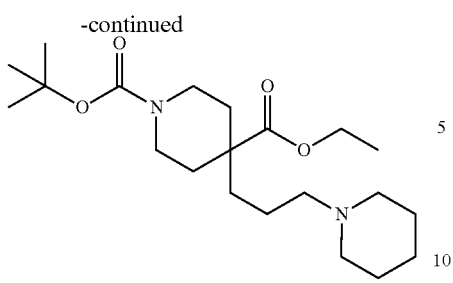

Piperidine (0.13 mL, 0.00132 mol) is added to a solution of 4-(3-bromopropyl)piperidine-1,4-dicarboxylic acid-1-tert-butyl ester-4-ethyl ester (0.1 gm, 0.00026 mol) in tetrahydrofuran (5 mL). The reaction mixture is heated at 60-65° C. for 3 hours. It is then cooled to room temperature, treated with demineralized water (12 mL) and extracted with ethyl acetate (2×20 mL). Combined extract is dried over sodium sulphate and concentrated under reduced pressure to get a crude residue which is purified by column chromatography (silica gel 230-400 mesh, methanol:dichloromethane, 1:9) to yield 4-(3-piperidin-1-yl propyl)piperidine-1,4-dicarboxylic acid-1-tert-butyl ester-4-ethyl ester.

Step (e)

This intermediate is prepared following the same procedure as that of 4-hydroxymethylpiperidine-4-carboxylic acid ethyl ester [step (c) of intermediate (XVIII)].

XXXVI) 4-(3-Pyrrolidin-1-yl-propyl)-piperidine-4-carboxylic acid ethyl ester

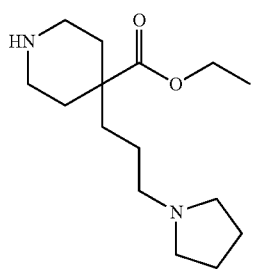 [SMILES: CCOC(=O)C1(CCCN2CCCC2)CCNCC1]

This intermediate is prepared following the same procedure as that of 4-(3-piperidin-1-yl-propyl)-piperidine-4-carboxylic acid ethyl ester (XXXV).

PREPARATION OF COMPOUNDS OF INVENTION

The process for preparation of some of the representative compounds of the present invention are mentioned herein below. Such disclosures are simply for illustrative purposes and should not be considered as limiting the invention.

Example 1

1-{4-[5-(3-chloro-4-cyclohexylphenyl)-[1,2,4]-oxadiazol-3-yl]benzyl}-4-methylpiperidine-4-carboxylic acid Step (a)

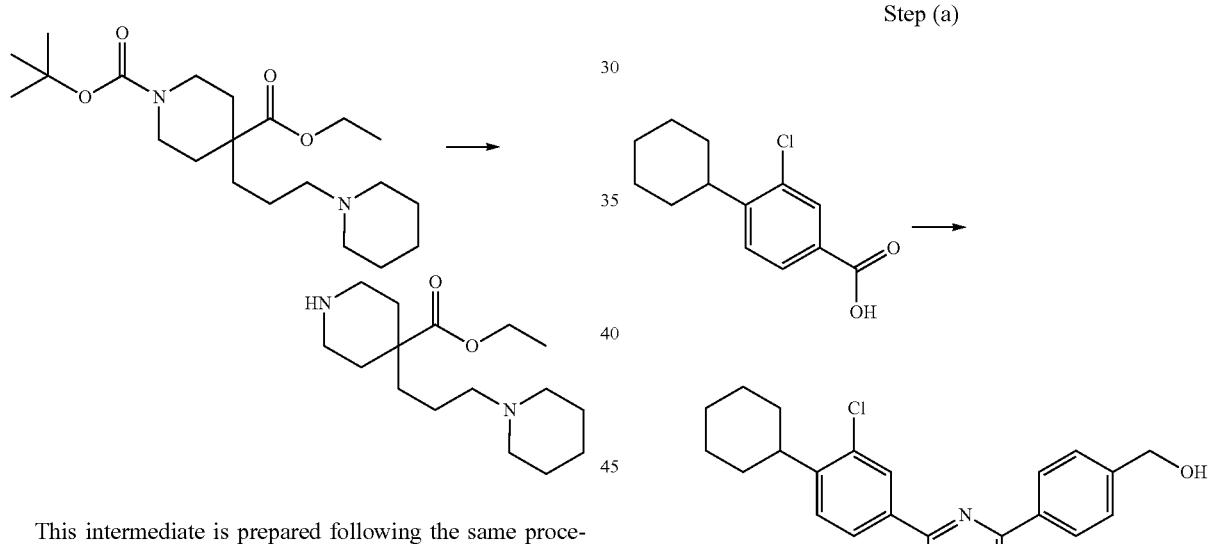

N,N-Dicyclohexylcarbodiimide (0.615 g, 0.003 mol) is added to a solution of 3-chloro-4-cyclohexyl benzoic acid (0.475 g, 0.002 mol), N-hydroxy-4-hydroxymethylbenzamidine (0.45 g, 0.003 mol) and N-hydroxybenzotriazole monohydrate (0.457 g, 0.003 mol) in N,N-dimethylformamide (10 mL). The reaction mixture is stirred at 130-135° C. for 2 hrs. It is then cooled to 0-5° C., filtered and washed with dichloromethane (2×20 mL). The filtrate is evaporated under reduced pressure and the residue is treated with demineralized water (20 mL). It is extracted with ethyl acetate (3×15 mL) and the combined extract is dried over sodium sulfate. Removal of solvent under reduced pressure gives a crude residue which is purified by column chromatography (silica gel 230-400, ethyl acetate:toluene, 15:85) to give {4-[5-(3-chloro-4-cyclohexylphenyl)-[1,2,4]-oxadiazol-3-yl]phenyl}methanol.

Step (b)

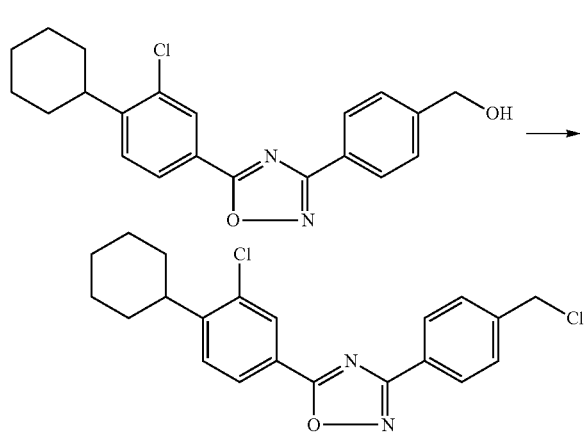

Thionyl chloride (0.27 mL, 0.0037 mol) and N,N-dimethylformamide (0.1 mL) are added to a stirred solution of {4-[5-(3-chloro-4-cyclohexylphenyl)-[1,2,4]-oxadiazol-3-yl]phenyl}methanol (0.45 g, 0.0012 mol) in dichloromethane (10 mL) at 0° C. The reaction mixture is heated at 40-45° C. and is stirred at this temperature for 1 hr. It is then cooled to 0-5° C. temperature, treated with demineralized water (3 mL) and is neutralized with 4N sodium hydroxide solution at 0-5° C. to adjust the pH 8-9. Finally it is extracted with dichloromethane (2×10 mL) and the combined extract is dried over sodium sulfate. Removal of solvent under reduced pressure gives 5-(3-chloro-4-cyclohexylphenyl)-3-(4-chloromethylphenyl)-[1,2,4]-oxadiazole.

Step (c)

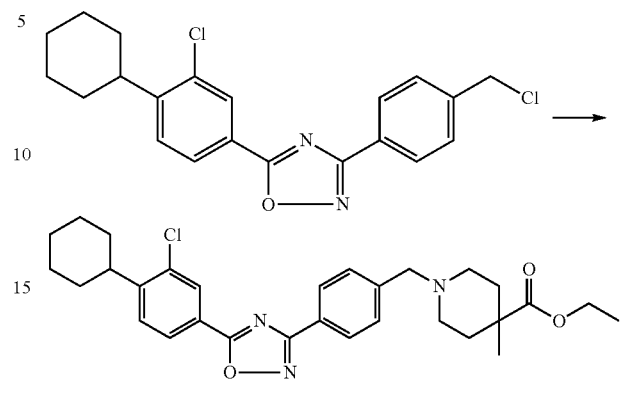

Potassium carbonate (0.16 g, 0.0012 mol) and 4-methylpiperidine-4-carboxylic acid ethyl ester (0.21 g, 0.0012 mol) are added to a solution of 5-(3-chloro-4-cyclohexylphenyl)-3-(4-chloromethylphenyl)-[1,2,4]-oxadiazole (0.3 g, 0.00077 mol) in N,N-dimethylformamide 15 mL). The reaction mixture is heated at 65-70° C. for 2 hrs. Removal of solvent gives a crude residue which is purified by column chromatography (silica gel 230-400 mesh, ethyl acetate:toluene, 1:4) to give 4-methyl-1-{4-[5-(3-chloro-4-cyclohexylphenyl)-[1,2,4]-oxadiazol-3-yl]benzyl}piperidine-4-carboxylic acid ethyl ester.

Step (d)

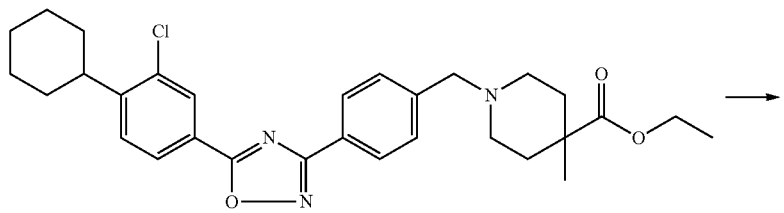

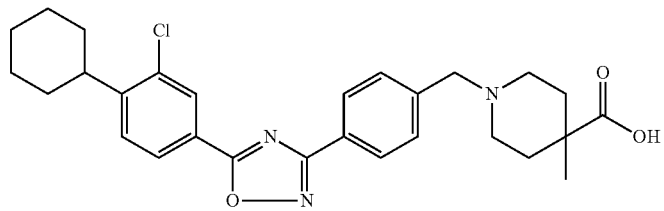

A solution of sodium hydroxide (0.1 g, 0.0023 mol) and potassium hydroxide (85% assay, 0.13 g, 0.0020 mol) in demineralized water (2 mL) is added to a solution of 4-methyl-1-{4-[5-(3-chloro-4-cyclohexylphenyl)-[1,2,4]-oxadiazol-3-yl]benzyl}piperidine-4-carboxylic acid ethyl ester (0.3 g, 0.00057 mol) in tetrahydrofuran and ethanol (14 mL, 1:1). The reaction mixture is heated under reflux (80° C.) for 2 hrs. It is then concentrated under reduced pressure to give a crude residue which is dissolved in demineralized water (10 mL) and acidified to pH~4-5 with 20% aqueous acetic acid solution. The resultant solid is filtered, dried and washed with acetone (2×10 mL). Solid is dried under vacuum to get 1-{4-[5-(3-chloro-4-cyclohexylphenyl)-[1,2,4]-oxadiazol-3-yl]benzyl}4-methyl piperidine-4-carboxylic acid.

Example 2

1-{4-[5-(3-chloro-4-isobutylphenyl)-[1,2,4]-oxadiazol-3-yl]benzyl}-4-methylpiperidine-4-carboxylic acid, tert-butylamine salt

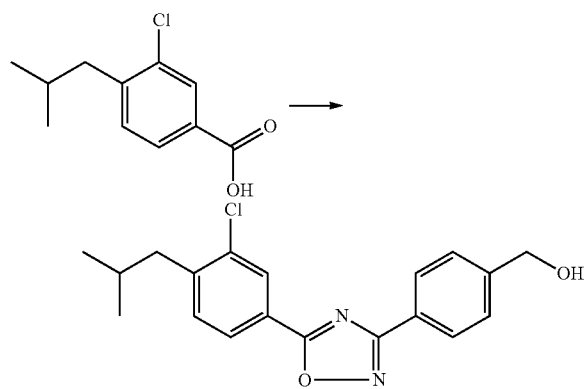

Step (a)

N,N-Dicyclohexylcarbodiimide (1.07 g, 0.0052 mol) is added to a solution of 3-chloro-4-isobutylbenzoic acid (0.74 g, 0.0035 mol), N-hydroxy-4-hydroxymethylbenzamidine (0.867 g, 0.0052 mol) and N-hydroxybenzotriazole monohydrate (0.798 g, 0.0052 mol) in N,N-dimethylformamide (15 mL). The reaction mixture is heated at 120-125° C. for 2 hrs. It is then cooled to 0-5° C., filtered and washed with dichloromethane (2×20 mL). The filtrate is evaporated under reduced pressure and the residue is treated with demineralized water (20 mL). It is extracted with ethyl acetate (2×30 mL) and the combined extract is dried over sodium sulfate. Removal of solvent under reduced pressure gives a crude residue which is purified by column chromatography (silica gel 230-400, ethyl acetate:toluene, 15:85) to give {4-[5-(3-chloro-4-isobutylphenyl)-[1,2,4]-oxadiazol-3-yl]-phenyl}methanol.

Step (b)

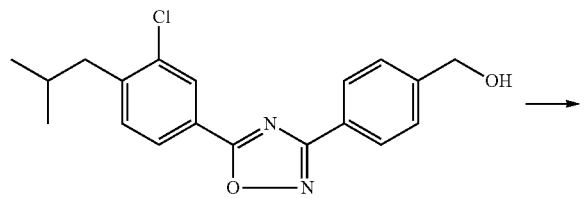

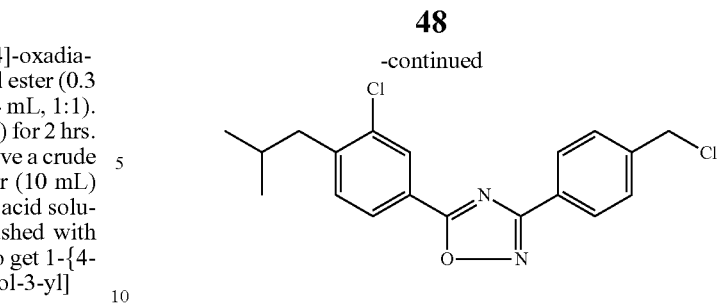

Thionyl chloride (3.1 mL, 0.043 mol) and N,N-dimethylformamide (0.2 mL) are added to a stirred solution of {4-[5-(3-chloro-4-isobutylphenyl)-[1,2,4]-oxadiazol-3-yl]-phenyl}methanol (4.9 g, 0.0143 mol) in dichloromethane (30 mL) at 0° C. The reaction mixture is heated at 40-45° C. and is stirred at this temperature for 30 minutes. It is then cooled to 0-5° C. temperature, treated with demineralized water (3 mL) and neutralized with caustic lye to adjust the pH to 8-9. Finally it is extracted with dichloromethane (2×20 mL) and the combined extract is dried over sodium sulfate. Removal of solvent under reduced pressure gives 5-(3-chloro-4-isobutylphenyl)-3-(4-chloromethylphenyl)-[1,2,4]-oxadiazole.

Step (c)

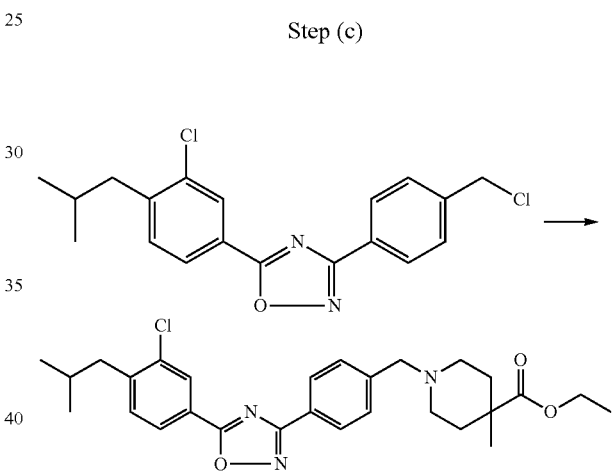

Potassium carbonate (0.29 g, 0.0021 mol) and 4-methylpiperidine-4-carboxylic acid ethyl ester (0.36 g, 0.0021 mol) are added to a solution of 5-(3-chloro-4-isobutylphenyl)-3-(4-chloromethylphenyl)-[1,2,4]-oxadiazole (0.5 g, 0.0014 mol) in N,N-dimethylformamide (10 mL). The reaction mixture is heated at 65-70° C. for 2 hours. Removal of solvent gives a crude residue which is purified by column chromatography (silica gel 230-400 mesh, toluene:ethyl acetate 4:1) to give 1-{4-[5-(3-chloro-4-isobutylphenyl)-[1,2,4]-oxadiazol-3-yl]-benzyl}-4-methylpiperidine-4-carboxylic acid ethyl ester.

Step (d)

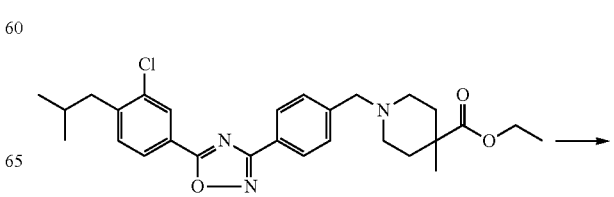

-continued

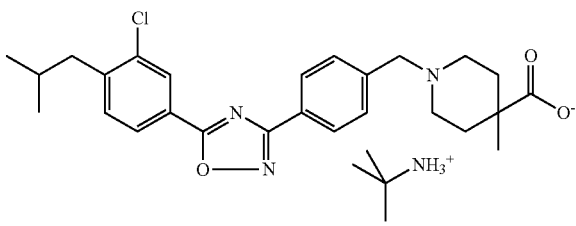

A solution of sodium hydroxide (0.22 g, 0.0055 mol) and potassium hydroxide (85% assay, 0.3 g, 0.0046 mol) in demineralized water (1 mL) is added to a solution of 1-{4-[5-(3-chloro-4-isobutylphenyl)-[1,2,4]-oxadiazol-3-yl]-benzyl}-4-methylpiperidine-4-carboxylic acid ethyl ester (0.67 g, 0.0014 mol) in (14 mL) of tetrahydrofuran and ethanol mixture (1:1). The reaction mixture is heated at 80° C. temperature for 4 hrs. It is then concentrated under reduced pressure to give a crude residue which is treated with demineralized water (20 mL) and acidified to pH~4-5 with 20% aqueous acetic acid solution (10 mL). The resultant solid is filtered, dried and washed with demineralized water (1×20 mL) and acetone (2×5 mL) respectively. The resultant solid is treated with a solution of methanol, dichloromethane and t-butylamine (2:7.5:0.5, 20 mL) and concentrated under reduced pressure. The solid mass is purified by column chromatography (silica gel 230-400 mesh, methanol:dichloromethane:t-butylamine, 1:8.9:0.1) to get 1-{4-[5-(3-chloro-4-isobutylphenyl)-[1,2,4]-oxadiazol-3-yl]-benzyl}-4-methylpiperidine-4-carboxylic acid t-butyl amine salt.

Example 3

1-{4-[5-(3-chloro-4-isobutylphenyl)-[1,2,4]-oxadiazol-3-yl]benzyl}-4-methylpiperidine-4-carboxylic acid

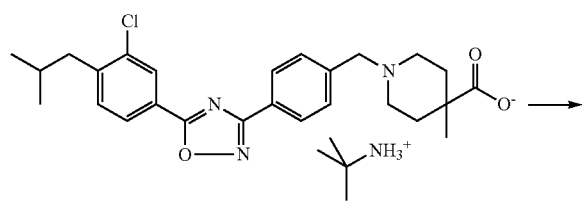

An aqueous solution of 20% acetic acid (1 mL) is added to a slurry of 1-{4-[5-(3-chloro-4-isobutylphenyl)-[1,2,4]-oxadiazol-3-yl]-benzyl}-4-methylpiperidine-4-carboxylic acid t-butyl amine salt (0.2 g, 0.00035 mol) in demineralized water (10 mL) to adjust the pH of the solution to 4-5. The solution is stirred at room temperature for 30 minutes, filtered and washed with demineralized water (2×5 mL) & acetone (1×5 mL). Finally it is dried to get 1-{4-[5-(3-chloro-4-isobutylphenyl)-[1,2,4]-oxadiazol-3-yl]-benzyl}-4-methylpiperidine-4-carboxylic acid as free acid.

Example 4

1-{4-[5-(3-chloro-4-isobutylphenyl)-[1,2,4]-oxadiazol-3-yl]benzyl}-4-methylpiperidine-4-carboxylic acid, sodium salt

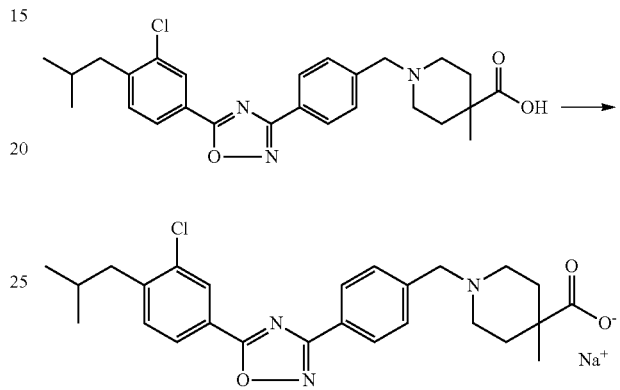

An aqueous solution of sodium hydroxide (0.006 g, 0.00015 mol) is added to a slurry of 1-{4-[5-(3-chloro-4-isobutylphenyl)-[1,2,4]-oxadiazol-3-yl]-benzyl}-4-methylpiperidine-4-carboxylic acid (0.065 g, 0.00014 mol) in tetrahydrofuran (5 mL). The solution is stirred at room temperature for 30 minutes and concentrated under reduced pressure to get sodium salt of 1-{4-[5-(3-chloro-4-isobutylphenyl)-[1,2,4]-oxadiazol-3-yl]-benzyl}-4-methylpiperidine-4-carboxylic acid.

Examples 5 & 6 may be prepared in the manner as mentioned for sodium salt (Example 4).

Example 5

1-{4-[5-(3-chloro-4-isobutylphenyl)-[1,2,4]-oxadiazol-3-yl]benzyl}-4-methylpiperidine-4-carboxylic acid, arginine salt

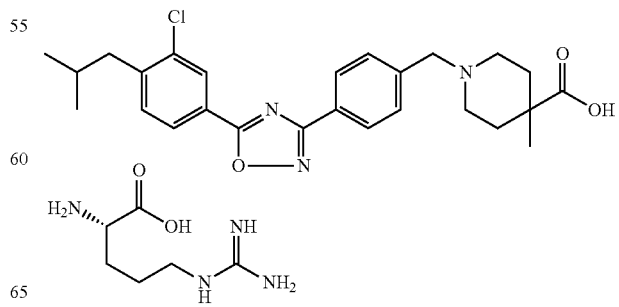

Example 6

1-{4-[5-(3-chloro-4-isobutylphenyl)-[1,2,4]-oxadiazol-3-yl]benzyl}-4-methylpiperidine-4-carboxylic acid, potassium salt

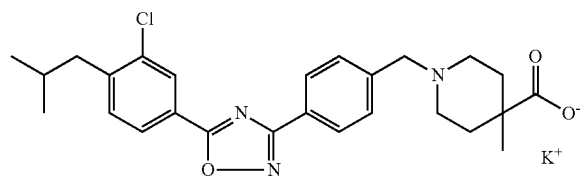 [SMILES: CC(C)Cc1ccc(-c2nc(-c3ccc(CN4CCC(C)(C(=O)[O-])CC4)cc3)no2)cc1Cl ; [K+]]

Example 7

1-{4-[5-(3-chloro-4-cyclopentylphenyl)-[1,2,4]-oxadiazol-3-yl]benzyl}-4-methylpiperidine-4-carboxylic acid

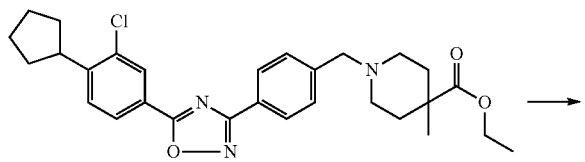

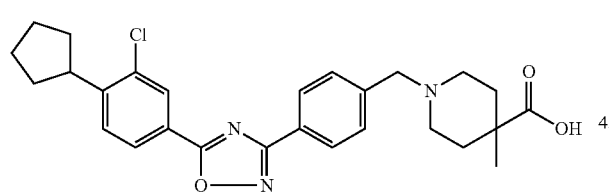

A solution of sodium hydroxide (0.13 g, 0.0033 mol) and potassium hydroxide (85% assay, 0.22 g, 0.0033 mol) in demineralized water (5 mL) is added to a solution of 1-{4-[5-(3-chloro-4-cyclopentylphenyl)-[1,2,4]-oxadiazol-3-yl]-benzyl}-4-methylpiperidine-4-carboxylic acid ethyl ester (0.43 g, 0.0008 mol) in a mixture of tetrahydrofuran and ethanol (1:1), 10 ML. The reaction mixture is heated at 80° C. temperature for 3 hrs. It is then concentrated under reduced pressure to give a crude residue which is treated with demineralized water (20 mL) and acidified to pH~4-5 with 20% aqueous acetic acid solution (10 mL). The resultant solid is filtered, dried and washed with demineralized water (1×20 mL) and acetone (2×5 mL) respectively. Finally it is dried under reduced pressure to get 1-{4-[5-(3-chloro-4-cyclopentylphenyl)-[1,2,4]-oxadiazol-3-yl]-benzyl}-4-methylpiperidine-4-carboxylic acid.

Example 8

1-{4-[5-(2-Chlorobiphenyl-4-yl)-[1,2,4]-oxadiazol-3-yl]benzyl}-4-methylpiperidine-4-carboxylic acid

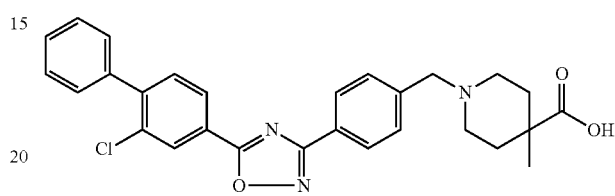

Example 8 may be prepared in a manner as mentioned above for Example 7.

Example 9

1-{4-[5-(3-chloro-4-cyclopentylphenyl)-[1,2,4]-oxadiazol-3-yl]benzyl}-4-methoxymethylpiperidine-4-carboxylic acid tert-butyl amine salt Step (a)

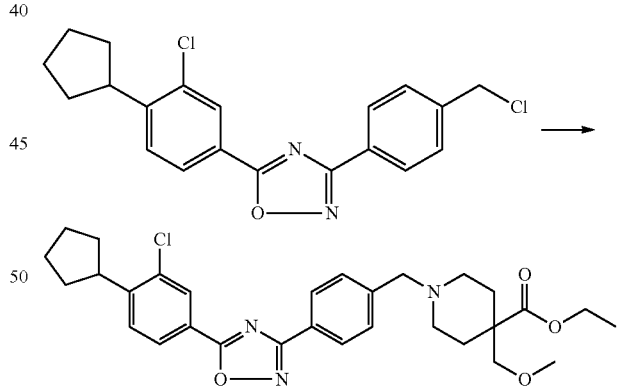

Potassium carbonate (0.28 g, 0.002 mol) and 4-methoxymethylpiperidine-4-carboxylic acid ethyl ester (0.4 g, 0.002 mol) are added to a solution of 5-(3-Chloro-4-cyclopentylphenyl)-3-(4-chloromethyl-phenyl)-[1,2,4]oxadiazole (0.5 g, 0.0013 mol) in N,N-dimethylformamide (15 mL). The reaction mixture is heated at 65-70° C. for 2 hours. Removal of solvent gives a crude residue which is purified by column chromatography (silica gel 230-400 mesh, toluene:ethyl acetate 4:1) to give 1-{4-[5-(3-chloro-4-cyclopentylphenyl)-

[1,2,4]-oxadiazol-3-yl]benzyl}-4-methoxy methyl piperidine-4-carboxylic acid ethyl ester.

Step (b)

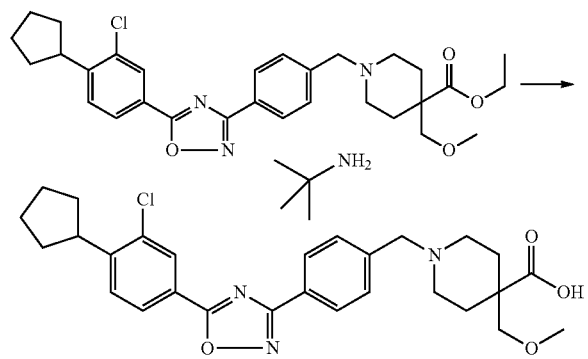

Potassium hydroxide powder (85% assay, 0.32 g, 0.0049 mol) and 18-crown-6-ether (0.01 g) are added to a solution of 1-{4-[5-(3-chloro-4-cyclopentylphenyl)-[1,2,4]-oxadiazol-3-yl]benzyl}-4-methoxymethylpiperidine-4-carboxylic acid ethyl ester (0.3 g, 0.00056 mol) in dry toluene (15 mL). The reaction mixture is refluxed for 3 hrs. It is then concentrated under reduced pressure and the residue is acidified to pH~4-5 with 20% aqueous solution of acetic acid (10 mL). The precipitated solid is filtered, dried and washed with demineralised water (2×10 mL) and acetone (2×5 mL). Solid mass is dissolved in a solution of methanol:dichlromethane:t-butylamine (1:8.9:0.1; 5 mL) and concentrated under reduced pressure to get crude residue which is purified by column chromatography (silica gel 230-400 mesh, methanol:dichloromethane:t-butylamine, 1:8.9:0.1) to give 1-{4-[5-(3-chloro-4-cyclopentylphenyl)-[1,2,4]-oxadiazol-3-yl]benzyl}-4-methoxymethylpiperidine-4-carboxylic acid.

Examples 10 to 28 may be prepared in similar manner as that mentioned for Example 9.

Example 10

1-{4-[5-(3-chloro-4-cyclohexylphenyl)-[1,2,4]-oxadiazol-3-yl]benzyl}-4-methoxymethylpiperidine-4-carboxylic acid tert-butyl amine salt

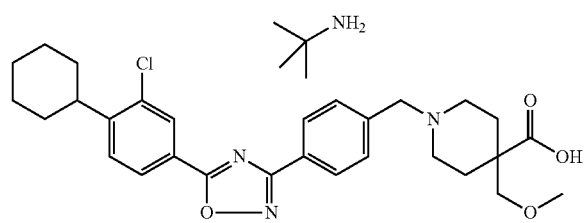

Example 11

1-{4-[5-(3-chloro-4-isobutylphenyl)-[1,2,4]-oxadiazol-3-yl]benzyl}-4-ethylpiperidine-4-carboxylic acid tert-butyl amine salt

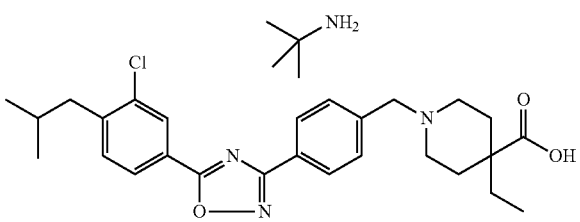

Example 12

4-allyl-1-{4-[5-(3-chloro-4-isobutylphenyl)-[1,2,4]-oxadiazol-3-yl]benzyl}piperidine-4-carboxylic acid tert-butyl amine salt

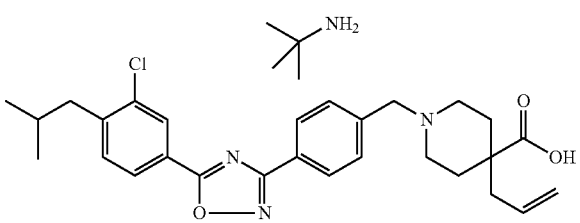

Example 13

1-{4-[5-(3-chloro-4-isobutylphenyl)-[1,2,4]-oxadiazol-3-yl]benzyl}-4-propylpiperidine-4-carboxylic acid tert-butyl amine salt

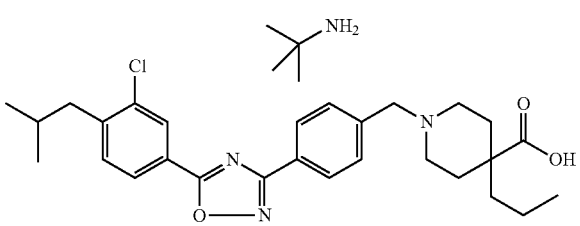

Example 14

1-{4-[5-(3-chloro-4-isobutylphenyl)-[1,2,4]-oxadiazol-3-yl]benzyl}-4-(2-methoxyethoxymethyl)piperidine-4-carboxylic acid tert-butyl amine salt

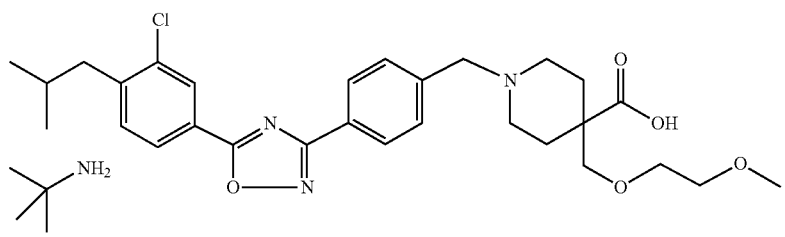

Example 15

1-{4-[5-(3-chloro-4-isobutylphenyl)-[1,2,4]-oxadiazol-3-yl]benzyl}-4-hydroxymethylpiperidine-4-carboxylic acid tert-butyl amine salt

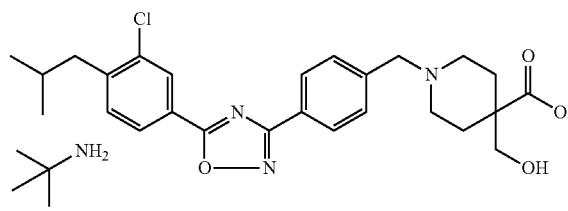

Example 16

1-{4-[5-(3-Chloro-4-isobutylphenyl)-[1,2,4]-oxadiazol-3-yl]-benzyl}-4-methoxymethylpiperidine-4-carboxylic acid tert-butyl amine salt

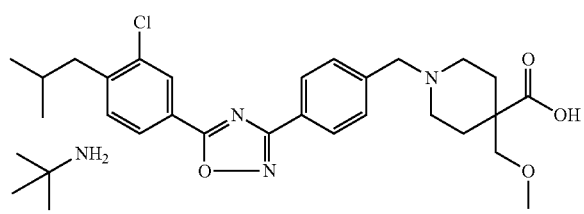

Example 17

4-Allyl-1-{4-[5-(2-chlorobiphenyl-4-yl)-[1,2,4]-oxadiazol-3-yl]-benzyl}piperidine-4-carboxylic acid tert-butyl amine salt

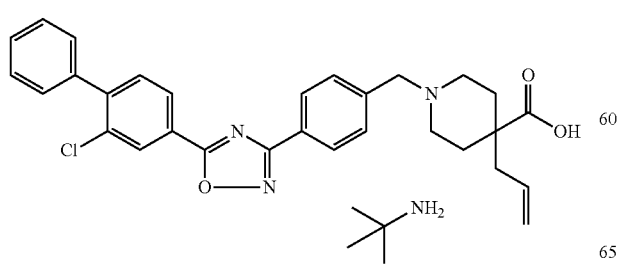

Example 18

1-{4-[5-(2-Chlorobiphenyl-4-yl)-[1,2,4]-oxadiazol-3-yl]-benzyl}-4-propylpiperidine-4-carboxylic acid tert-butyl amine salt

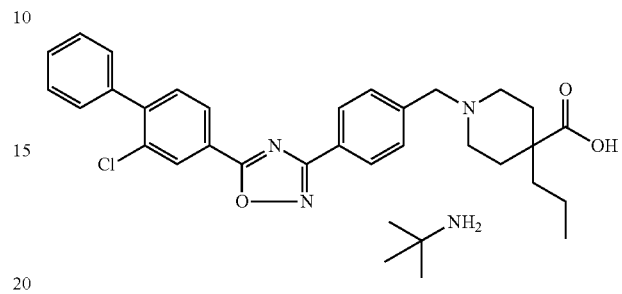

Example 19

1-{4-[5-(2-Chlorobiphenyl-4-yl)-[1,2,4]-oxadiazol-3-yl]-benzyl}-4-(2-methoxyethoxymethyl)piperidine-4-carboxylic acid tert-butyl amine salt

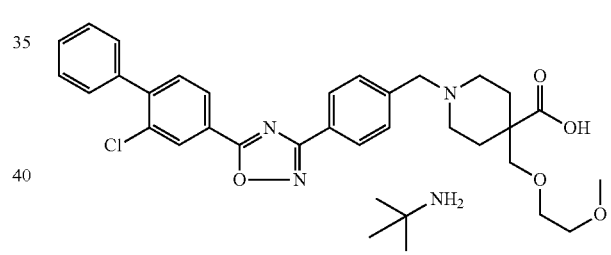

Example 20

4-Benzyloxymethyl-1-{4-[5-(2-chlorobiphenyl-4-yl)-[1,2,4]-oxadiazol-3-yl]-benzyl}piperidine-4-carboxylic acid tert-butyl amine salt

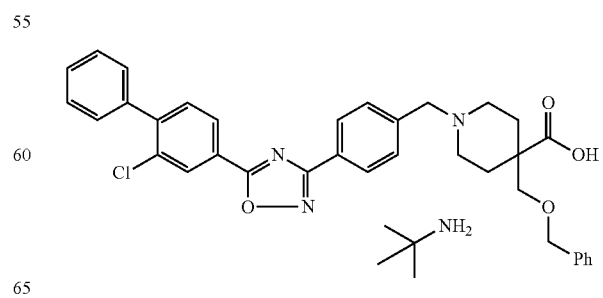

Example 21

4-Benzyloxymethyl-1-[4-{5-(3-chloro-4-isobutylphenyl)-[1,2,4]-oxadiazol-3-yl]-benzyl}piperidine-4-carboxylic acid tert-butyl amine salt

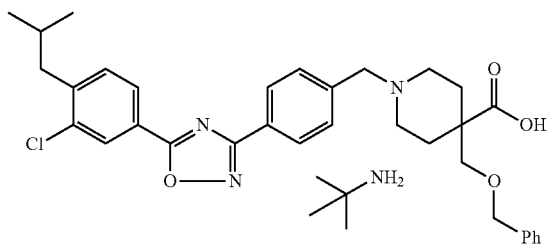

Example 22

1-{4-[5-(2-Chlorobiphenyl-4-yl)-[1,2,4]-oxadiazol-3-yl]-benzyl}-4-hydroxymethylpiperidine-4-carboxylic acid tert-butyl amine salt

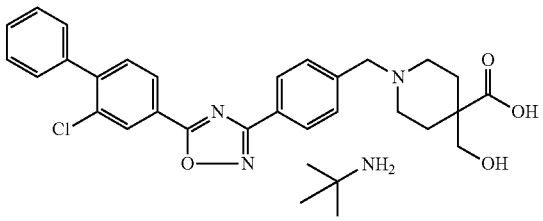

Example 23

1-{4-[5-(3-Chloro-4-isobutylphenyl)-[1,2,4]-oxadiazol-3-yl]-benzyl}-4-phenylpiperidine-4-carboxylic acid tert-butyl amine salt

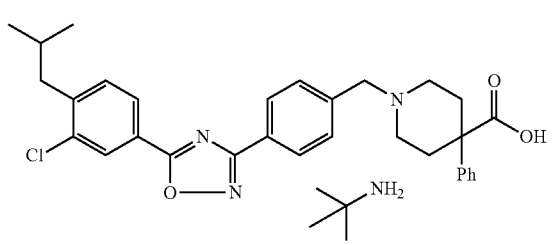

Example 24

4-Benzyl-1-[4-{5-(3-chloro-4-isobutylphenyl)-[1,2,4]-oxadiazol-3-yl]benzyl}-piperidine-4-carboxylic acid tert-butyl amine salt

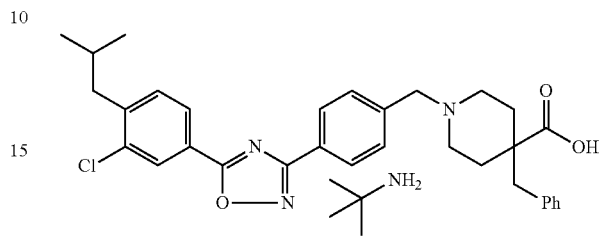

Example 25

1-{4-[5-(3-Chloro-4-isobutyl-phenyl)-[1,2,4]-oxadiazol-3-yl]-benzyl}-4-(4-fluoro-benzyl)-piperidine-4-carboxylic acid tert-butyl amine salt

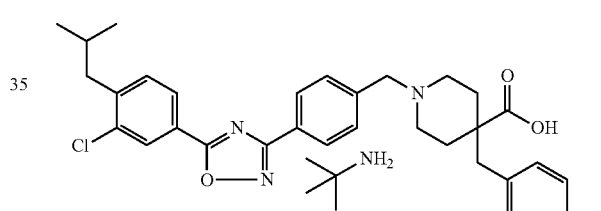

Example 26

1-{4-[5-(3-Chloro-4-isobutyl-phenyl)-[1,2,4]-oxadiazol-3-yl]-benzyl}-4-(2-fluoro-benzyl)-piperidine-4-carboxylic acid tert-butyl amine salt

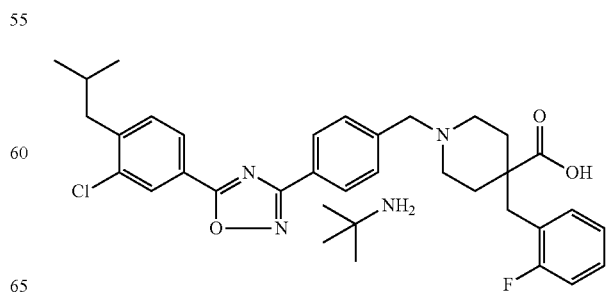

Example 27

1-{4-[5-(3-Chloro-4-isobutyl-phenyl)-[1,2,4]-oxadiazol-3-yl]-benzyl}-4-(4-methoxy-benzyl)-piperidine-4-carboxylic acid tert-butyl amine salt

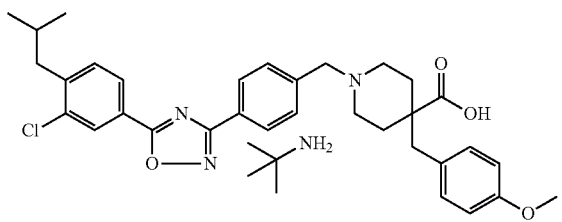

Example 28

1-{4-[5-(3-Chloro-4-isobutyl-phenyl)-[1,2,4]-oxadiazol-3-yl]-benzyl}-4-(2-methoxy-benzyl)-piperidine-4-carboxylic acid tert-butyl amine salt

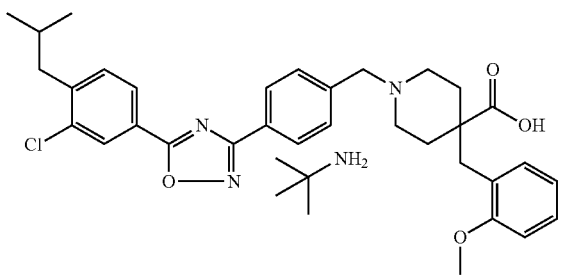

Example 29

1-{4-[5-(2-chlorobiphenyl-4-yl)-[1,2,4]-oxadiazol-3-yl]benzyl}-4-methoxymethylpiperidine-4-carboxylic acid tert-butyl amine salt

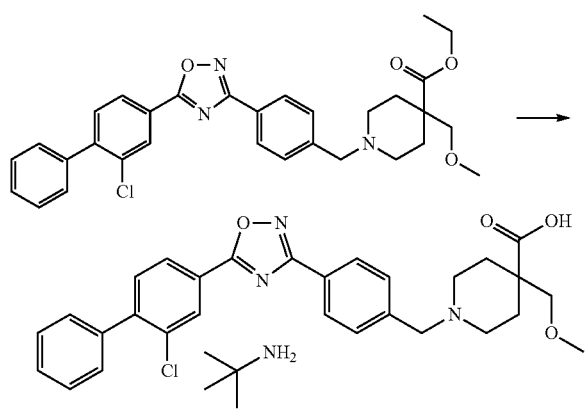

Potassium hydroxide powder (85% assay, 0.394 g, 0.0060 mol) and N-methyl-N,N-dioctyloctan-1-ammonium chloride (0.02 g) are added to a solution of 1-{4-[5-(2-chlorobiphenyl-4-yl)-[1,2,4]-oxadiazol-3-yl]benzyl}-4-methoxymethylpiperidine-4-carboxylic acid ethyl ester (0.38 g, 0.00069 mol) in N,N'-dimethyl formamide (5 mL). The reaction mixture is stirred at 80° C. temperature for 2 hrs. It is then cooled to room temperature and acidified with 20% aqueous acetic acid solution to pH~5-6. The precipitated solid is filtered, dried and washed with (2×5 mL) acetone. The solid mass is purified by column chromatography (silica gel 230-400 mesh, methanol:dichloromethane:t-butylamine, 1:8.9:0.1) to give 1-{4-[5-(2-chlorobiphenyl-4-yl)-[1,2,4]-oxadiazol-3-yl]benzyl}-4-methoxymethyl-piperidine-4-carboxylic acid.

Example 30

1-{4-[5-(2-Chlorobiphenyl-4-yl)-[1,2,4]-oxadiazol-3-yl]-benzyl}-4-ethylpiperidine-4-carboxylic acid tert-butyl amine salt Step (a)

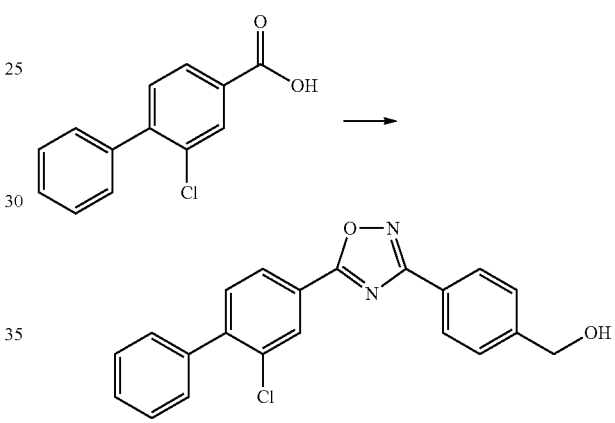

N,N-Dicyclohexylcarbodiimide (4 g, 0.019 mol) is added to a solution of 2-chlorobiphenyl-4-carboxylic acid (3 g, 0.013 mol), N-hydroxy-4-hydroxymethyl benzamidine (2.9 g, 0.017 mol) and N-hydroxybenzotriazole monohydrate (2.9 g, 0.019 mol) in N,N-dimethylformamide (40 mL). The reaction mixture is heated at 120-125° C. for 3 hrs. It is then cooled to 0-5° C., filtered and washed with dichloromethane (2×15 mL). The filtrate is evaporated under reduced pressure and the residue is treated with demineralized water (20 mL). It is extracted with ethyl acetate (2×20 mL) and the combined extract is dried over sodium sulfate. Removal of solvent under reduced pressure gives a crude residue which is purified by column chromatography (silica gel 230-400, ethyl acetate:toluene, 1:9) to give {4-[5-(2-chlorobiphenyl-4-yl)-[1,2,4]-oxadiazol-3-yl]-phenyl}-methanol.

Step (b)

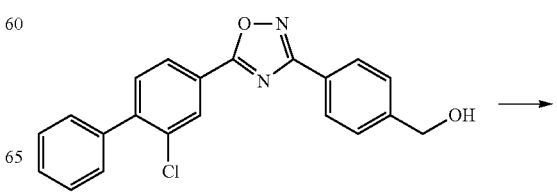

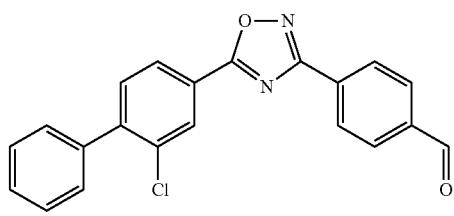

Pyridiniumchlorochromate (3.6 g, 0.017 mol) is added to a solution of {4-[5-(2-chlorobiphenyl-4-yl)-[1,2,4]-oxadiazol-3-yl]-phenyl}-methanol (4.0 g, 0.011 mol) in dichloromethane (40 mL). The reaction mixture is stirred at room temperature for 30 minutes, filtered and washed with dichloromethane (40 mL). Filtrate is concentrated under reduced pressure to give crude which is purified by column chromatography (230; 400 mesh: 9.5:0.5 toluene:ethyl acetate) to yield 4-[5-(2-chlorobiphenyl-4-yl)-[1,2,4]-oxadiazol-3-yl]-benzaldehyde.

Step (c)

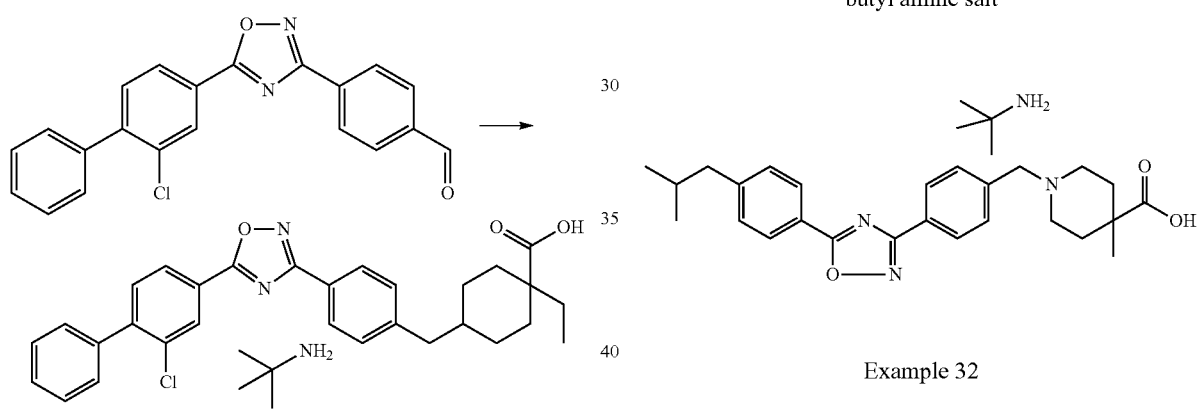

A solution of 4-ethylpiperidine-4-carboxylic acid (0.45 g, 0.00283 mol) in demineralized water (3 mL) is added to a solution of 4-[5-(2-chloro-4-isobutylphenyl)-[1,2,4]-oxadiazole-3-yl]benzaldehyde (0.685 gm, 0.0019 mol) in methanol and dichloromethane (1:3, 20 mL). Acetic acid (1.1 mL) is added to the reaction mixture. The reaction mixture is stirred at room temperature for 30 minutes. A solution of sodium cyanoborohydried (0.238 gm, 0.0038 mol) in methanol (2 mL) is added to the reaction mixture and stirred for 1.5 hrs at room temperature. Solvent is removed from the reaction mixture under reduced pressure to get a crude solid which is treated with demineralized water (10 mL) and filtered. Solid mass is dissolved in a solution of methanol:dichlromethane:t-butylamine (1:8.9:0.1; 15 mL) and concentrated under reduced pressure to get crude residue which is purified by column chromatography (silica gel 230-400 mesh, methanol:dichloromethane:t-butylamine, 1:8.9:0.1) to give 1-{4-[5-(2-chlorobiphenyl-4-yl)-[1,2,4]-oxadiazol-3-yl]-benzyl}-4-ethylpiperidine-4-carboxylic acid.

Example 31 may be prepared in a manner as mentioned above for Example 2.

Example 31

1-{4-[5-(4-Isobutyl-phenyl)-[1,2,4]-oxadiazol-3-yl]-benzyl}-4-methyl-piperidine-4-carboxylic acid tert-butyl amine salt Example 32

1-{4-[5-(3-Chloro-4-isobutylphenyl-[1,2,4]-oxadiazol-3-yl]benzyl}-4-(4-methoxybutyl)piperidine-4-carboxylic acid tert-butyl amine salt

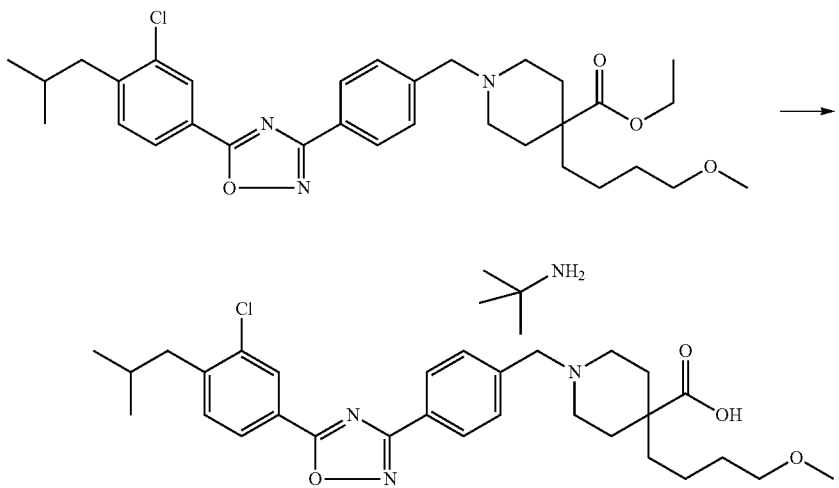

An aqueous solution (0.5 mL) of potassium hydroxide (0.39 g, 0.0059 mol, assay 85%) is added to a solution of 1-{4-[5-(3-chloro-4-isobutylphenyl)-[1,2,4]-oxadiazol-3-yl]benzyl}-4-(4-methoxybutyl)piperidine-4-carboxylic acid ethyl ester (0.48 g, 0.0008 mol) in a mixture of tetrahydrofuran (5 mL) and ethanol (5 mL). The reaction mixture is heated at 75-80° C. for 20 hrs, cooled to room temperature and then concentrated under reduced pressure. The residue is treated with demineralized water (10 mL) and acidified to pH~5-5.5 using 20% aqueous acetic acid (15 mL). The precipitated solid is filtered, washed with demineralized water (10 mL) and acetone (10 mL). The Solid mass is dissolved in a solution of methanol:dichlromethane:t-butylamine (1:8.9:0.1; 5 mL) and concentrated under reduced pressure to get crude residue which is purified by column chromatography (silica gel 230-400 mesh, methanol:dichloromethane:t-butylamine, 1:8.9:0.1) to give 1-{4-[5-(3-chloro-4-isobutylphenyl-[1,2,4]-oxadiazol-3-yl]benzyl}-4-(4-methoxybutyl)piperidine-4-carboxylic acid.

Example 33

1-{4-[5-(3-chloro-4-isobutylphenyl)-[1,2,4]-oxadiazol-3-yl]benzyl}-4-(2-methoxyethoxymethyl)piperidine-4-carboxylic acid potassium salt

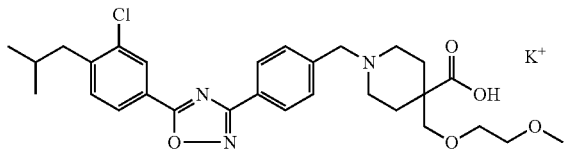 [SMILES: COCCOCC1(C(=O)O)CCN(Cc2ccc(-c3noc(-c4ccc(CC(C)C)c(Cl)c4)n3)cc2)CC1 ; [K+]]

1-{4-[5-(3-chloro-4-isobutyl-phenyl)-[1,2,4]oxadiazol-3-yl]-benzyl}-4-(2-methoxy-ethoxymethyl)-piperidine-4-carboxylic acid ethyl ester (6 g, 0.01052 mol) is added in to a solvent mixture containing THF (120 ml, 20 vol) and Rectified Spirit (120 ml, 20 vol). Stirred to get a clear solution at RT. Potassium Hydroxide (4.17 g, 0.06315 mol) is charged in to the above reaction flask at RT. The reaction mixture is heated at 70-80° C. temperature for 10-12 hrs. It is then concentrated under reduced pressure to give a crude residue which is codistilled with acetone (12 ml, 2 vol) and suspended in aq. Acetone[5% water, 90 ml, 15 vol]. Stirred the product slurry at 30-40° C. for 30 mins. Cooled to 0-5° C. and stirred for 1-2 hrs. The resultant solid is filtered, dried and washed with aq. Acetone[5% water, 48 ml, 8 vol]. Suck dried the product under nitrogen for 30-60 mins and further dried under vacuum at 450° C. to yield 7 g [M/C: 12%] of Potassium salt of 1-{4-[5-(3-chloro-4-isobutyl-phenyl)-[1,2,4]oxadiazol-3-yl]-benzyl}-4-(2-methoxy-ethoxymethyl)-piperidine-4-carboxylic acid.

The above product is leached with Ethyl acetate and dried under vacuum to yield 6.8 g of Potassium salt of 1-{4-[5-(3-chloro-4-isobutyl-phenyl)-[1,2,4]oxadiazol-3-yl]-benzyl}-4-(2-methoxyethoxymethyl)-piperidine-4-carboxylic acid.

The potassium salt [6.15 gm] is crystallized from Methanol to yield 4.5 g of pure Potassium salt of 1-{4-[5-(3-chloro-4-isobutyl-phenyl)-[1,2,4]oxadiazol-3-yl]-benzyl}-4-(2-methoxy-ethoxymethyl)-piperidine-4-carboxylic acid.

Examples 34-35 may be prepared in a similar manner as that mentioned for Example 9.

Example 34

1-{4-[5-(3-Chloro-4-isobutyl-phenyl)-[1,2,4]-oxadiazol-3-yl]-benzyl}-4-(2-phenoxy-ethyl)-piperidine-4-carboxylic acid tert-butyl amine salt

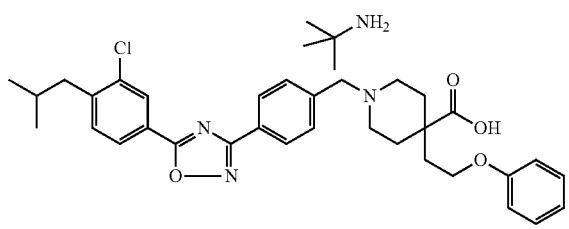

Example 35

1-{4-[5-(3-Chloro-4-isobutyl-phenyl)-[1,2,4]-oxadiazol-3-yl]-benzyl}-4-(2,6-difluoro-benzyl)-piperidine-4-carboxylic acid tert-butyl amine salt

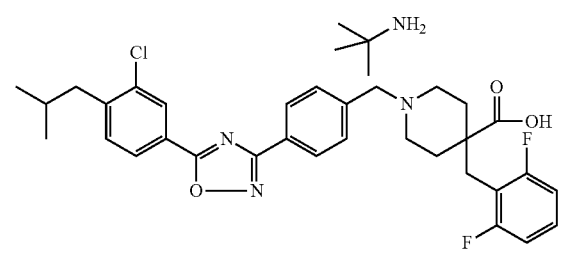

Examples 36-38 may be prepared in similar manner as that mentioned for Example 30.

Example 36

1-{4-[5-(3-Chloro-4-isobutyl-phenyl)-[1,2,4]-oxadiazol-3-yl]-benzyl}-4-isobutyl-piperidine-4-carboxylic acid tert-butyl amine salt

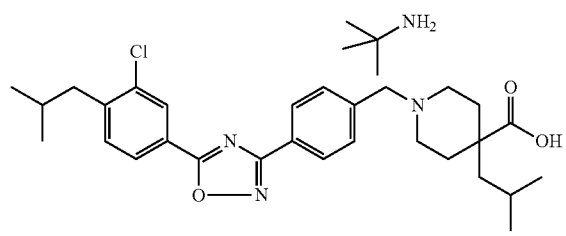

Example 37

1-{4-[5-(3-Chloro-4-isobutyl-phenyl)-[1,2,4]-oxadiazol-3-yl]-benzyl}-4-isopropyl-piperidine-4-carboxylic acid tert-butyl amine salt

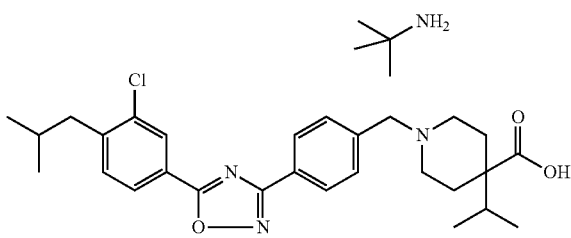

Example 38

1-{4-[5-(3-Chloro-4-isobutyl-phenyl)-[1,2,4]-oxadiazol-3-yl]-benzyl}-4-(3-trifluoro methyl-benzyl)-piperidine-4-carboxylic acid tert-butyl amine salt

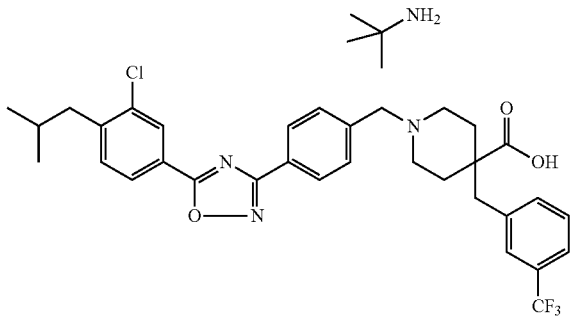

Examples 39-41 may be prepared in similar manner as that mentioned for Example 9.

Example 39

1-{4-[5-(3-Chloro-4-isobutyl-phenyl)-[1,2,4]-oxadiazol-3-yl]-benzyl}-4-furan-2-ylmethyl-piperidine-4-carboxylic acid tert-butyl amine salt

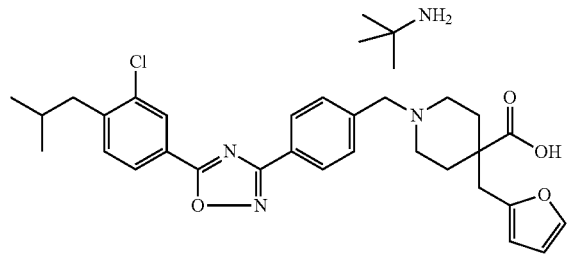

Example 40

1-{4-[5-(3-Chloro-4-isobutyl-phenyl)-[1,2,4]-oxadiazol-3-yl]-benzyl}-4-pyridin-2-ylmethyl-piperidine-4-carboxylic acid tert-butyl amine salt

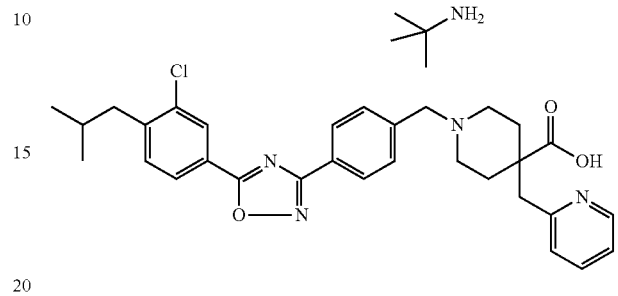

Example 41

1-{4-[5-(3-Chloro-4-isobutyl-phenyl)-[1,2,4]-oxadiazol-3-yl]-benzyl}-4-[2-(2-methoxy-phenoxy)-ethyl]-piperidine-4-carboxylic acid tert-butyl amine salt

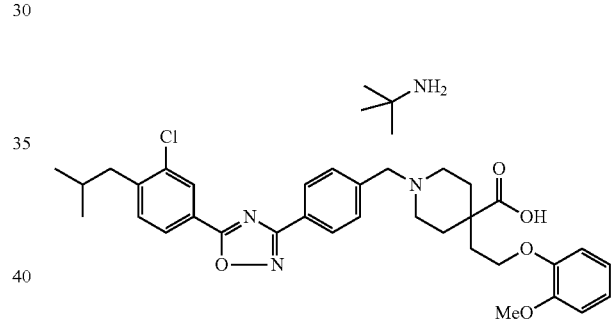

Examples 42-43 may be prepared in similar manner as that mentioned for Example 9.

Example 42

1-{4-[5-(3-Chloro-4-isobutyl-phenyl)-[1,2,4]-oxadiazol-3-yl]-benzyl}-4-pyridin-3-ylmethyl-piperidine-4-carboxylic acid tert-butyl amine salt

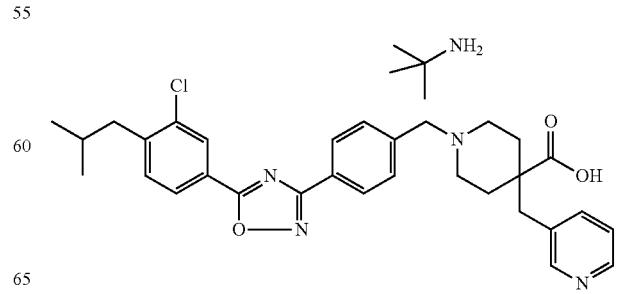

Example 43

1-{4-[5-(3-Chloro-4-isobutyl-phenyl)-[1,2,4]-oxadiazol-3-yl]-benzyl}-4-pyridin-4-ylmethyl-piperidine-4-carboxylic acid tert-butyl amine salt

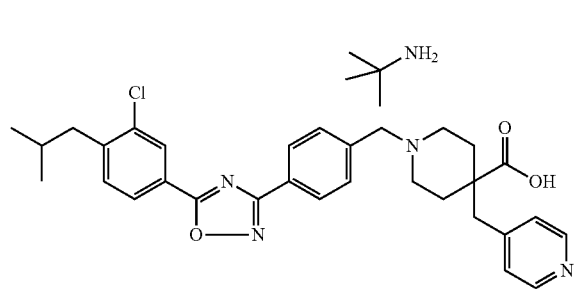

Examples 44-47 may be prepared in similar manner as that mentioned for Example 2.

Example 44

1-{4-[5-(3-Chloro-4-isopropoxy-phenyl)-[1,2,4]-oxadiazol-3-yl]-benzyl}-4-methyl-piperidine-4-carboxylic acid tert-butyl amine salt

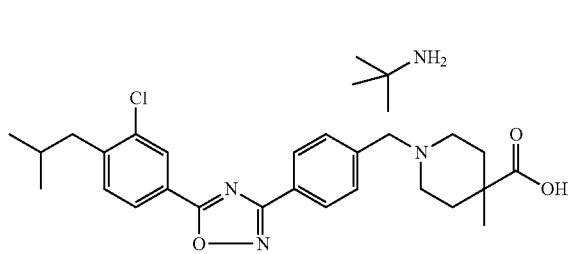

Example 45

1-{4-[5-(4-tert-Butyl-3-chloro-phenyl)-[1,2,4]-oxadiazol-3-yl]-benzyl}-4-methyl-piperidine-4-carboxylic acid tert-butyl amine salt

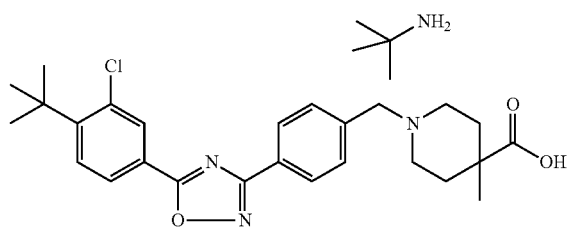

Example 46

1-{4-[5-(3-Chloro-4-propyl-phenyl)-[1,2,4]-oxadiazol-3-yl]-benzyl}-4-methyl-piperidine-4-carboxylic acid tert-butyl amine salt

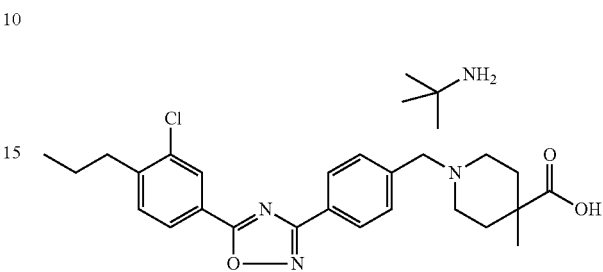

Example 47

1-{4-[5-(3-Chloro-4-isopropoxy-phenyl)-[1,2,4]-oxadiazol-3-yl]-benzyl}-4-(2-methoxy-ethoxymethyl)-piperidine-4-carboxylic acid tert-butyl amine salt

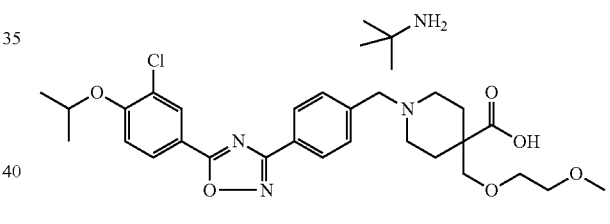

Examples 48-58 may be prepared in similar manner as that mentioned for Example 9

Example 48

1-{4-[5-(3-Chloro-4-isopropoxy-phenyl)-[1,2,4]-oxadiazol-3-yl]-benzyl}-4-ethyl-piperidine-4-carboxylic acid tert-butyl amine salt

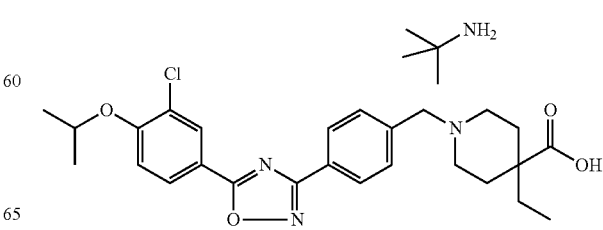

Example 49

4-Allyl-1-{4-[5-(3-chloro-4-isopropoxy-phenyl)-[1,2,4]-oxadiazol-3-yl]-benzyl}-piperidine-4-carboxylic acid tert-butyl amine salt

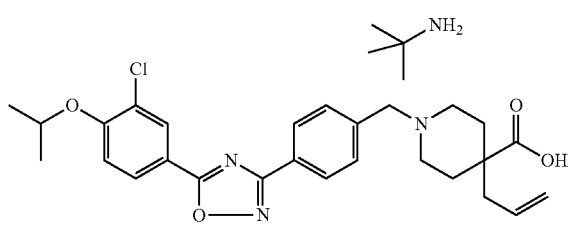

Example 50

1-{4-[5-(2-Chloro-biphenyl-4-yl)-[1,2,4]-oxadiazol-3-yl]-benzyl}-4-pyridin-2-ylmethyl-piperidine-4-carboxylic acid tert-butyl amine salt

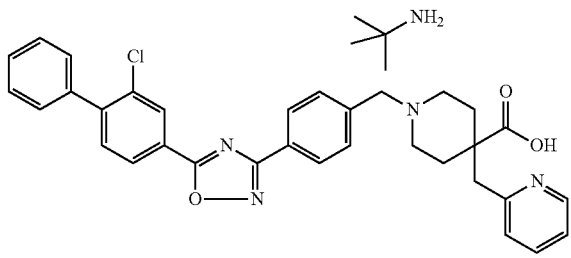

Example 51

1-{4-[5-(2-Chloro-biphenyl-4-yl)-[1,2,4]-oxadiazol-3-yl]-benzyl}-4-(4-methoxy-benzyl)-piperidine-4-carboxylic acid tert-butyl amine salt

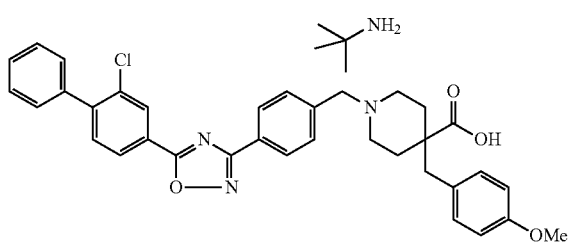

Example 52

1-{4-[5-(2-Chloro-biphenyl-4-yl)-[1,2,4]-oxadiazol-3-yl]-benzyl}-4-(4-fluoro-benzyl)-piperidine-4-carboxylic acid tert-butyl amine salt

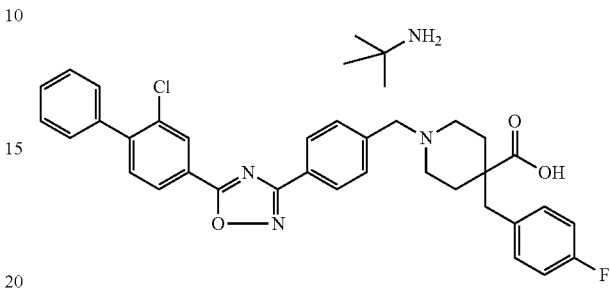

Example 53

1-{4-[5-(3-Chloro-4-cyclohexylphenyl)-[1,2,4]-oxadiazol-3-yl]-benzyl}-4-(4-methoxy-benzyl)-piperidine-4-carboxylic acid tert-butyl amine salt

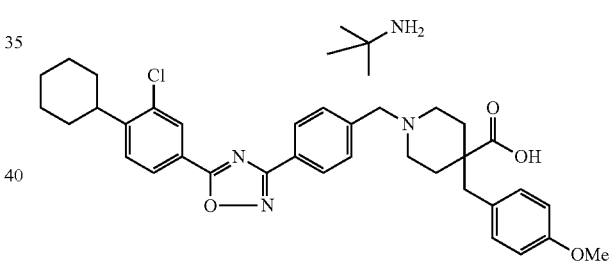

Example 54

1-{4-[5-(3-Chloro-4-cyclohexylphenyl)-[1,2,4]-oxadiazol-3-yl]-benzyl}-4-ethyl-piperidine-4-carboxylic acid tert-butyl amine salt

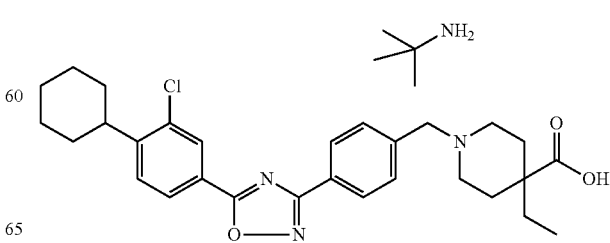

Example 55

4-Benzyl-1-{4-[5-(2-chloro-biphenyl-4-yl)-[1,2,4]-oxadiazol-3-yl]-benzyl}-piperidine-4-carboxylic acid tert-butyl amine salt

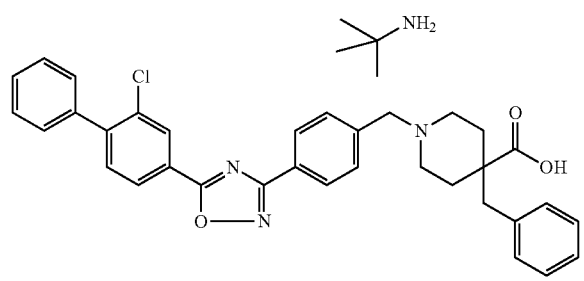

Example 56

1-{4-[5-(3-Chloro-4-cyclohexyl-phenyl)-[1,2,4]-oxadiazol-3-yl]-benzyl}-4-pyridin-2-ylmethyl-piperidine-4-carboxylic acid tert-butyl amine salt

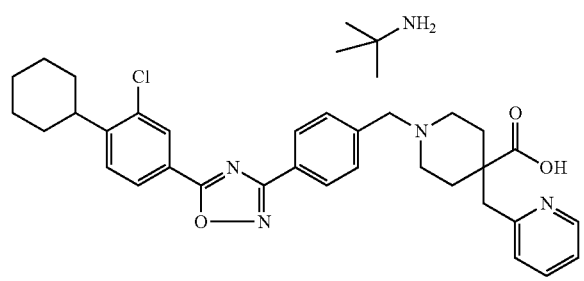

Example 57

1-{4-[5-(3-Chloro-4-isopropoxy-phenyl)-[1,2,4]-oxadiazol-3-yl]-benzyl}-4-methoxymethyl-piperidine-4-carboxylic acid tert-butyl amine salt

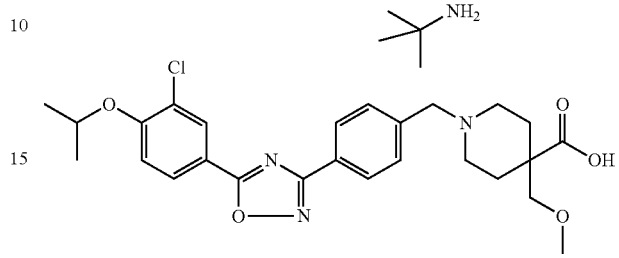

Example 58

1-{4-[5-(2-Chloro-biphenyl-4-yl)-[1,2,4]-oxadiazol-3-yl]-benzyl}-4-pyridin-3-ylmethyl-piperidine-4-carboxylic acid tert-butyl amine salt

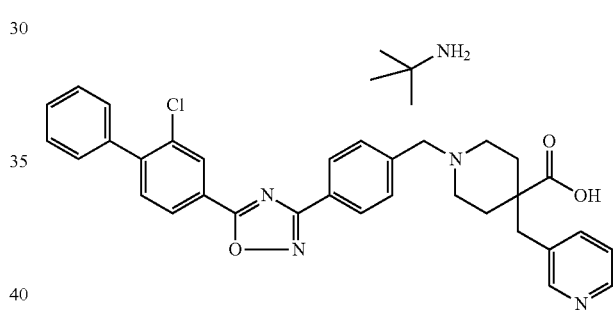

Example 59 may be prepared in similar manner as that mentioned for Example 2.

Example 59

1-{4-[5-(3-Chloro-4-isobutyl-phenyl)-[1,2,4]-oxadiazol-3-yl]-benzyl}-4-(2-ethoxy-ethoxymethyl)-piperidine-4-carboxylic acid tert-butyl amine salt

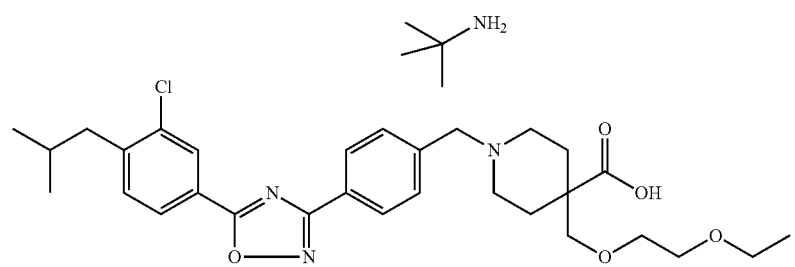

Examples 60 may be prepared in similar manner as that mentioned for Example 9.

Example 60

1-{4-[5-(3-Chloro-4-isobutyl-phenyl)-[1,2,4]-oxadiazol-3-yl]-benzyl}-4-isopropoxy methyl-piperidine-4-carboxylic acid tert-butyl amine salt

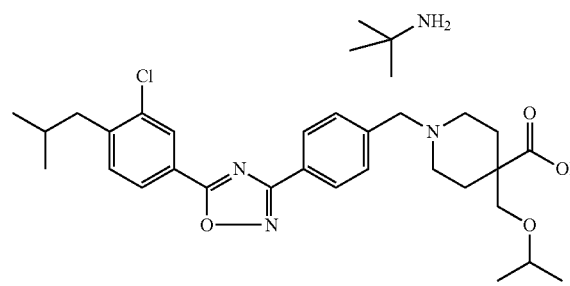

Examples 61 may be prepared in similar manner as that mentioned for Example 32.

Example 61

1-{4-[5-(3-Chloro-4-isobutyl-phenyl)-[1,2,4]-oxadiazol-3-yl]-benzyl}-4-cyclopentyloxymethyl-piperidine-4-carboxylic acid tert-butyl amine salt

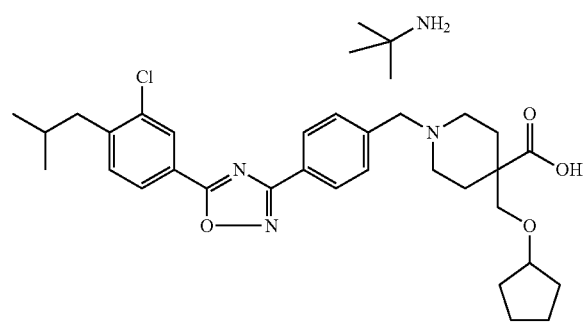

Examples 62 may be prepared in similar manner as that mentioned for Example 9.

Example 62

1-{4-[5-(3-Chloro-4-isobutyl-phenyl)-[1,2,4]-oxadiazol-3-yl]-benzyl}-4-thiophen-2-ylmethyl-piperidine-4-carboxylic acid tert-butyl amine salt

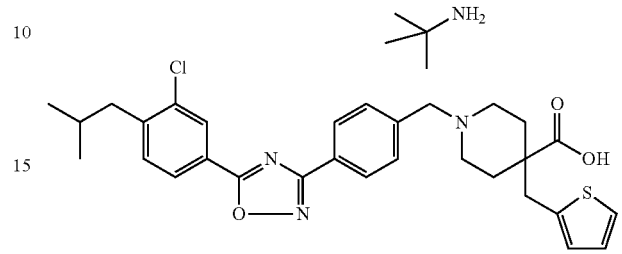

Examples 63 may be prepared in similar manner as that mentioned for Example 30.

Example 63

1-{4-[5-(3-Chloro-4-isobutyl-phenyl)-[1,2,4]-oxadiazol-3-yl]-benzyl}-4-cyclopropylmethyl-piperidine-4-carboxylic acid tert-butyl amine salt

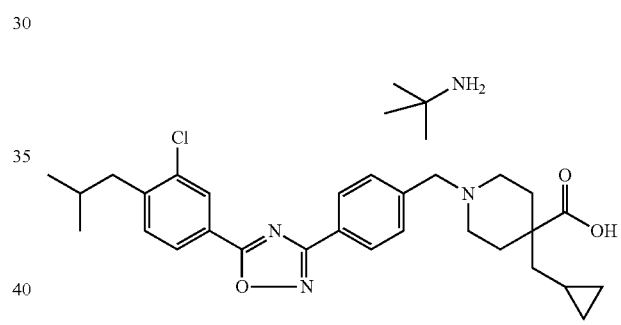

Examples 64-66 may be prepared in similar manner as that mentioned for Example 9.

Example 64

1-{4-[5-(3-Chloro-4-isobutyl-phenyl)-[1,2,4]-oxadiazol-3-yl]-benzyl}-4-(2-morpholin-4-yl-ethyl)-piperidine-4-carboxylic acid

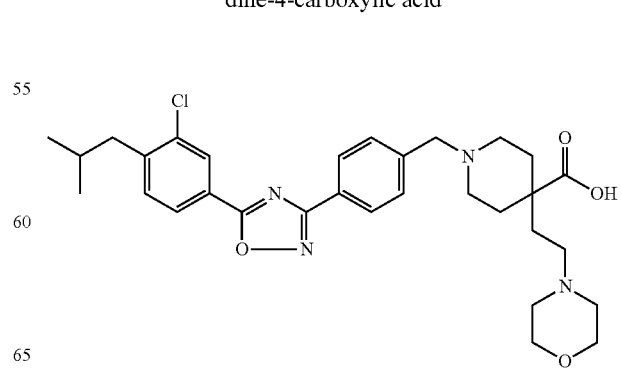

Example 65

1-{4-[5-(3-Chloro-4-isobutyl-phenyl)-[1,2,4]-oxadiazol-3-yl]-benzyl}-4-(3-piperidin-1-yl-propyl)-piperidine-4-carboxylic acid tert-butyl amine salt

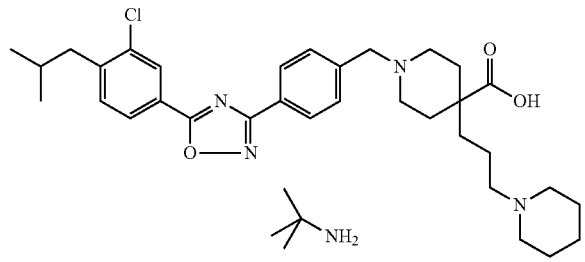

Example 66

1-{4-[5-(3-Chloro-4-isobutyl-phenyl)-[1,2,4]-oxadiazol-3-yl]-benzyl}-4-(3-pyrrolidin-1-yl-propyl)-piperidine-4-carboxylic acid tert-butyl amine salt

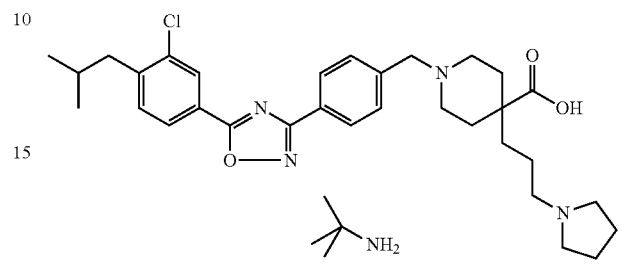

| Ex. No. | Structure | (MS) (ES+) | NMR data |
|---|---|---|---|
| 1 | 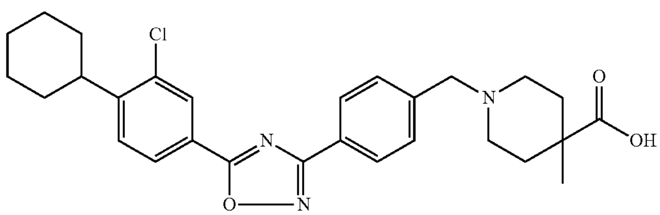 [SMILES: CC1(C(=O)O)CCN(Cc2ccc(-c3noc(-c4ccc(C5CCCCC5)c(Cl)c4)n3)cc2)CC1] | 494.24 | as free form<br>PMR: (CDCl$_3$ + CD$_3$OD + TFA; 400.13 MHz; ppm)<br>1.25-1.60 (s merged in m, 9H); 1.75-2.02 (br m, 6H); 2.40 (d, J = 14.64 Hz, 2H); 2.83-3.07 (br t, 2H); 3.07-3.19 (br t, 1H); 3.54-3.68 (br d, 2H); 4.33 (s, 2H); 7.42-7.62 (m, 3H); 8.05 (d, J = 7.78 Hz, 1H); 8.17-8.27 (br d, 3H)<br>One exchangeable proton |
| 3 | 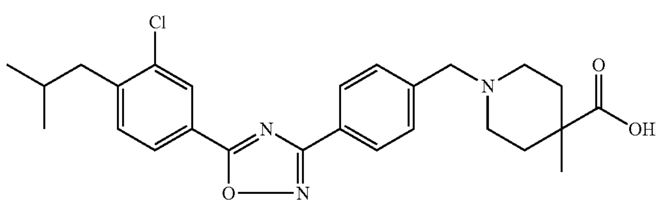 [SMILES: CC(C)Cc1ccc(-c2nc(-c3ccc(CN4CCC(C)(C(=O)O)CC4)cc3)no2)cc1Cl] | 468.23 | as free form<br>PMR: (CDCl$_3$ + CD$_3$OD + TFA; 400.13 MHz; ppm)<br>0.97 (d, J = 5.99 Hz, 6H); 1.30 (s, 3H); 1.74-1.88 (br t, 2H); 2.00-2.12 (br m, 1H); 2.35 (d, J = 14.49 Hz, 2H); 2.69-2.77 (br d, 2H); 2.89-3.01 (br t, 2H); 3.48-3.59 (br d, 2H); 4.28 (s, 2H); 7.48-7.43 (br d, 1H); 7.54-7.62 (br d, 2H); 7.99-8.05 (br d, 1H); 8.18-8.27 (br d, 3H)<br>One exchangeable proton |
| 7 | 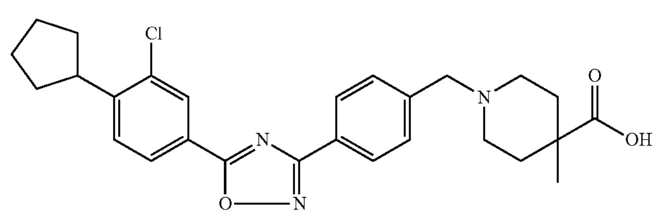 [SMILES: CC1(C(=O)O)CCN(Cc2ccc(-c3noc(-c4ccc(C5CCCC5)c(Cl)c4)n3)cc2)CC1] | 480.23 | As free form<br>PMR: (CDCl$_3$ + CD$_3$OD + TFA; 500.13 MHz; ppm)<br>1.29 (s, 3H); 1.57-1.67 (br m, 2H); 1.72-1.92 (br m, 6H); 2.12-2.22 (br m, 2H); 2.31 (d, J = 14.60 Hz, 2H); 2.88 (t, J = 12.50 Hz, 2H); 3.48-3.58 (br m, 3H); 4.36 (s, 2H); 7.50 (d, J = 7.15 Hz, 1H); 7.55 (d, J = 7.95 Hz, 2H); 8.04 (d, J = 8.00 Hz, 1H); 8.18-8.26 (br m, 3H)<br>One exchangeable proton |
| 8 | 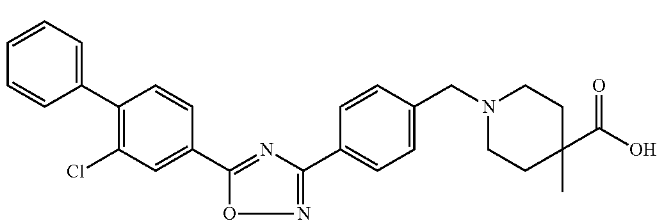 [SMILES: CC1(C(=O)O)CCN(Cc2ccc(-c3noc(-c4ccc(-c5ccccc5)c(Cl)c4)n3)cc2)CC1] | 488.24 | As free form<br>PMR: CDCl$_3$ + CD$_3$OD + TFA; 500.13 MHz; δ ppm)<br>1.29 (s, 3H); 1.81-1.90 (br t, 2H); 2.31 (d, J = 14.40 Hz, 2H); 2.86-2.95 (br t, 2H); 3.46-3.53 (br d, 2H); 4.26 (s, 2H); 7.43-7.53 (br m, 5H); 7.55-7.64 (m, 3H); 8.16 (dd, J$_1$ = 7.90 Hz, J$_2$ = 1.00 Hz, 1H); 8.25 (d, J = 8.05 Hz, 2H); 8.35 (s, J = 0.90 Hz, 1H);<br>One exchangeable proton |

-continued

| Ex. No. | Structure | (MS) (ES+) | NMR data |
|---|---|---|---|
| 9 | 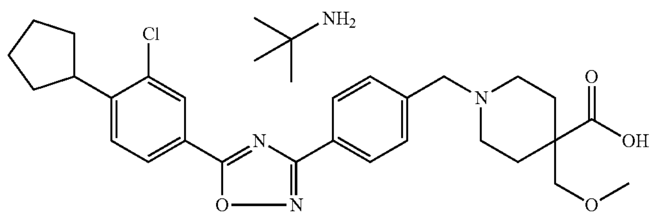 | 510.21 | as t-butyl amine salt<br>PMR: (CDCl₃ + D₂O; 500.13 MHz; δ ppm)<br>1.28 (s, 9H); 1.55-1.65 (br m, 4H); 1.71-1.80 (br m, 2H); 1.80-1.89 (br m, 2H); 2.10-2.18 (br m, 4H); 2.38-2.46 (br t, 2H); 2.71-2.77 (br d, 2H); 3.29 (s, 3H); 3.41 (s, 2H); 3.46-3.56 (m, 1H); 3.63 (s, 2H); 7.44-7.51 (m, 3H); 8.01 (d, J = 8.30 Hz, 1H); 8.08 (d, J = 8.05 Hz, 2H); 8.18 (d, J = 0.90 Hz, 1H)<br>Three exchangeable protons |
| 10 | 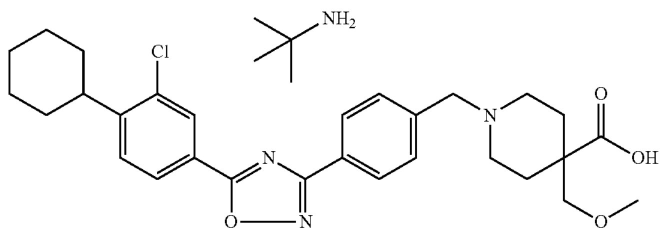 | 524.21 | as t-butyl amine salt<br>PMR: (CDCl₃ + CD₃OD; 500.13 MHz; δ ppm)<br>1.29-1.31 (s merged in m, 10H); 1.37-1.54 (m, 4H); 1.54-1.63 (m, 2H); 1.78-1.85 (br d, 1H); 1.91 (t, J = 13.20 Hz, 4H); 2.13 (d, J = 13.45 Hz, 2H); 2.37 (t, J = 10.20 Hz, 2H); 2.74-2.82 (br d, 2H); 3.06-3.14 (m, 1H); 3.30 (s, 3H); 3.40 (s, 2H); 3.64 (s, 2H); 7.46-7.52 (m, 3H); 8.05 (dd, J₁ = 8.20 Hz, J₂ = 1.50 Hz, 1H); 8.10 (d, J = 8.15 Hz, 2H); 8.19 (d, J = 1.35 Hz, 1H)<br>Three exchangeable protons |
| 11 | 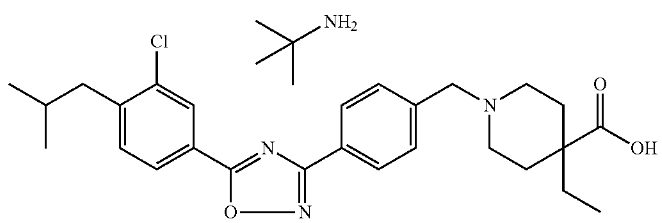 | 481.94 | as t-butyl amine salt<br>PMR: (CDCl₃ + CD₃OD; 500.13 MHz; δ ppm)<br>0.85 (t, J = 7.45 Hz, 3H); 0.97 (d, J = 6.60 Hz, 6H); 1.26 (s, 9H); 1.42-1.57 (m, 4H); 2.01-2.08 (m, 1H); 2.12 (d, J = 13.40 Hz, 2H); 2.27 (t, J = 11.00 Hz, 2H); 2.71 (d, J = 7.20 Hz, 2H); 2.75-2.82 (br d, 2H); 3.60 (s, 2H); 7.38 (d, J = 8.00 Hz, 1H); 7.48 (d, J = 8.05 Hz, 2H); 8.02 (dd, J₁ = 7.90 Hz, J₂ = 1.40 Hz, 1H); 8.10 (d, J = 8.05 Hz, 2H); 8.20 (d, J = 1.10 Hz, 1H)<br>Three exchangeable protons |
| 12 | 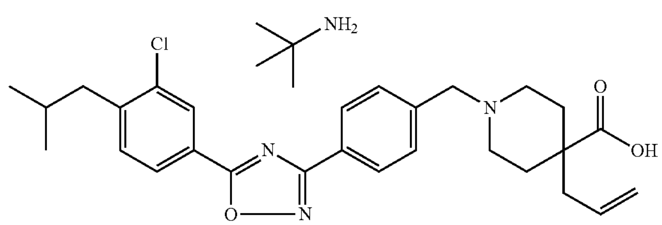 | 493.94 | as t-butyl amine salt<br>PMR: (CDCl₃ + CD₃OD; 500.13 MHz; δ ppm)<br>0.97 (d, J = 6.55 Hz, 6H); 1.26 (s, 9H); 1.48-1.56 (br t, 2H); 2.00-2.13 (m, 3H); 2.24-2.34 (m, 4H); 2.70 (d, J = 7.20 Hz, 2H); 2.72-2.79 (br d, 2H); 3.60 (s, 2H); 4.98-5.06 (m, 2H); 5.73-5.83 (m, 1H); 7.38 (d, J = 7.95 Hz, 1H); 7.48 (d, J = 8.10 Hz, 2H); 8.01 (dd, J₁ = 7.90 Hz, J₂ = 1.15 Hz, 1H); 8.10 (d, J = 8.10 Hz, 2H); 8.20 (d, J = 1.25 Hz, 1H)<br>Three exchangeable protons |
| 13 | 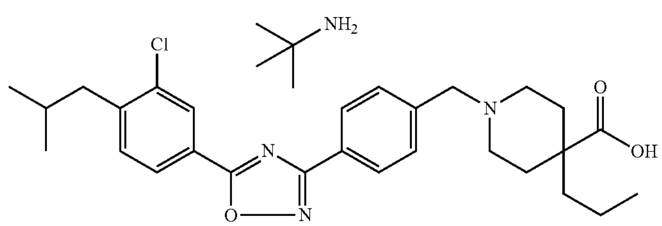 | 495.95 | as t-butyl amine salt<br>PMR: (CDCl₃ + CD₃OD; 500.13 MHz; δ ppm)<br>0.79 (t, J = 7.10 Hz, 3H); 0.89 (d, J = 6.55 Hz, 6H); 1.15 (s, 9H); 1.16-1.24 (br m, 2H); 1.33-1.45 (br m, 4H); 1.92-2.00 (m, 1H); 2.00-2.07 (br d, 2H); 2.12 (br t, 2H); 2.63 (d, J = 7.20 Hz, 2H); 2.64-2.71 (br d, 2H); 3.50 (s, 2H); 7.30 (d, J = 7.95 Hz, 1H); 7.39 (d, J = 7.95 Hz, 2H); 7.94 (d, J = 7.95 Hz, 1H); 8.02 (d, J = 8.00 Hz, 2H); 8.12 (s, 1H)<br>Three exchangeable protons |

| Ex. No. | Structure | (MS) (ES+) | NMR data |
|---|---|---|---|
| 14 | 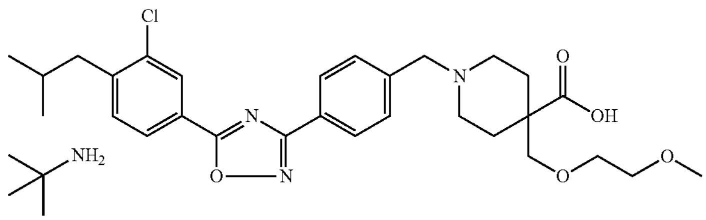 | 542.04 | as t-butyl amine salt<br>PMR: (CDCl₃; 400.13 MHz; δ ppm)<br>0.96 (d, J = 6.61 Hz, 6H); 1.26 (s, 9H); 1.53-1.63 (br t, 2H); 1.98-2.08 (m, 1H); 2.13-2.22 (br d, 2H); 2.35-2.44 (br t, 2H); 2.69 (d, J = 7.19 Hz, 2H); 2.73-2.80 (br d, 2H); 3.36 (s, 3H); 3.49 (s, 2H); 3.42-3.60 (br d, 4H); 3.62 (s, 2H); 7.35 (7.97 Hz, 1H); 7.48 (d, J = 8.04 Hz, 2H); 8.00 (dd, J₁ = 7.99 Hz, J₂ = 1.17 Hz, 1H); 8.09 (d, J = 8.08 Hz, 2H); 8.20 (d, J = 1.03 Hz, 1H)<br>Three exchangeable protons |
| 15 | 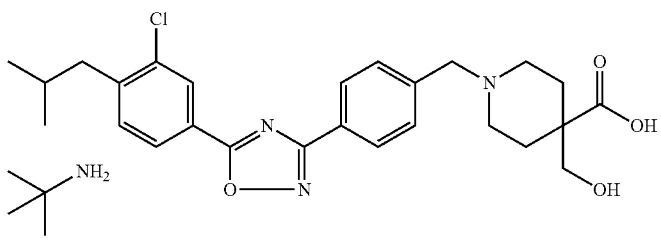 | 483.96 | as t-butyl amine salt<br>PMR: (CDCl₃ + CD₃OD + TFA; 500.13 MHz; ppm)<br>0.97 (d, J = 6.60 Hz, 6H); 1.39 (s, 9H); 1.84-1.95 (br t, 2H); 2.00-2.11 (m, 1H); 2.31 (d, J = 14.60 Hz, 2H); 2.71 (d, J = 7.20 Hz, 2H); 3.02 (d, J = 12.60 Hz, 2H); 3.54 (d, J = 11.80 Hz, 2H); 3.66 (s, 2H); 4.27 (s, 2H); 7.39 (d, J = 7.95 Hz, 1H); 7.58 (d, J = 8.10 Hz, 2H); 8.01 (dd, J₁ = 7.95 Hz, J₂ = 1.55 Hz, 1H); 8.19-8.25 (m, 3H)<br>Four exchangeable protons |
| 16 | 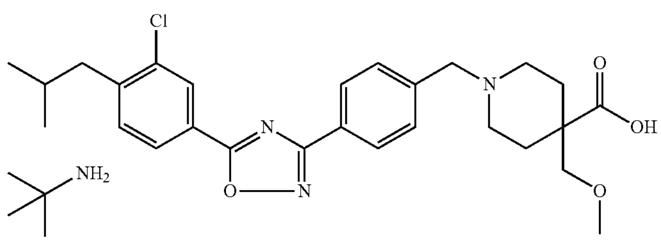 | 498.19 | as t-butyl amine salt<br>PMR: (CDCl₃ + CD₃OD; 500.13 MHz; δ ppm)<br>0.97 (d, J = 6.62 Hz, 6H); 1.29 (s, 9H); 1.53-1.63 (br m, 2H); 1.98-2.09 (m, 1H); 2.09-2.17 (br d, 2H); 2.37 (t, J = 10..67 Hz, 2H); 2.70 (d, J = 7.21 Hz, 2H); 2.74-2.82 (br d, 2H); 3.30 (s, 3H): 3.39 (s, 2H); 3.63 (s, 2H); 7.38 (d, J = 7.99 Hz, 1H); 7.49 (d, J = 8.10 Hz, 2H); 8.01 (dd, J₁ = 7.91 Hz, J₂ = 1.36 Hz, 1H); 8.10 (d, J = 8.10 Hz, 2H); 8.20 (d, J = 1.28 Hz, 1H)<br>Three exchangeable protons |
| 17 | 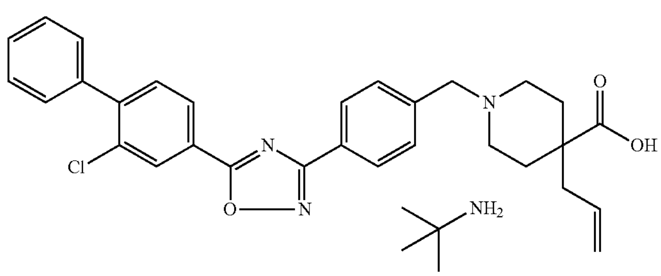 | 513.93 | as t-butyl amine salt<br>PMR: (CDCl₃ + CD₃OD; 500.13 MHz; δ ppm)<br>1.28 (s, 9H); 1.50-1.58 (br t, 2H); 2.11 (d, J = 13.40 Hz, 2H); 2.26 (d, J = 7.25 Hz, 2H); 2.28-2.36 (br t, 2H); 2.76-2.83 (br d, 2H); 3.63 (s, 2H); 4.99-5.07 (m, 2H); 5.73-5.82 (m, 1H); 7.43-7.52 (m, 7H); 7.55 (d, J = 8.05 Hz, 1H); 8.12 (d, J = 8.15 Hz, 2H); 8.16 (dd, J₁ = 8.00 Hz, J₂ = 1.60 Hz, 1H); 8.34 (d, J = 1.50 Hz, 1H)<br>Three exchangeable protons |
| 18 | 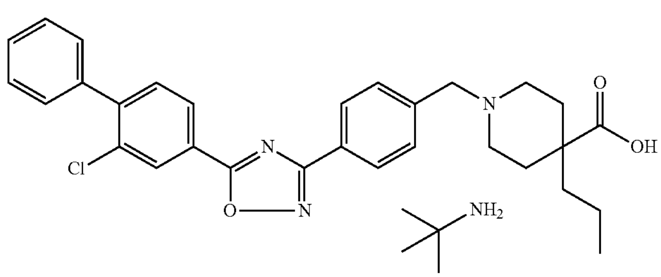 | 515.95 | as t-butyl amine salt<br>PMR: (CDCl₃ + CD₃OD; 500.13 MHz; δ ppm)<br>0.88 (t, J = 7.15 Hz, 3H); 1.25 (s, 9H); 1.27-1.34 (m, 2H); 1.43-1.55 (m, 4H); 2.13 (d, J = 13.40 Hz, 2H); 2.26 (t, J = 10.90 Hz, 2H); 2.74-2.82 (br d, 2H); 3.60 (s, 2H); 7.43-7.52 (m, 7H); 7.55 (d, J = 7.95 Hz, 1H); 8.12 (d, J = 8.00 Hz, 2H); 8.16 (dd, J₁ = 8.00 Hz, J₂ = 1.45 Hz, 1H); 8.34 (d, J = 1.25 Hz, 1H)<br>Three exchangeable protons |

-continued

| Ex. No. | Structure | (MS) (ES+) | NMR data |
|---|---|---|---|
| 19 | 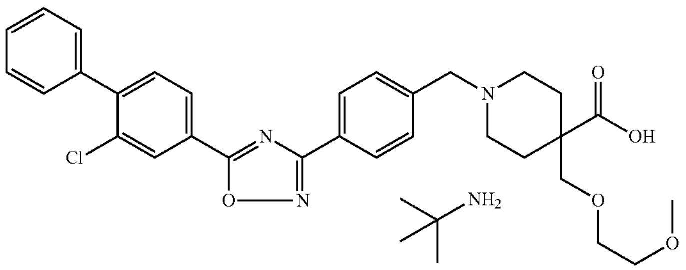 | 561.99 | as t-butyl amine salt<br>PMR: (CDCl₃; 400.13 MHz; δ ppm)<br>1.31 (s, 9H); 1.52-1.62 (br t, 2H); 2.13-2.22 (br d, 2H); 2.34-2.45 (br t, 2H); 2.73-2.82 (br d, 2H); 3.37 (s, 3H); 3.48 (s, 2H); 3.52-3.59 (br s, 4H); 3.62 (s, 2H); 7.41-7.56 (m, 8H); 8.09-8.17 (m, 3H); 8.34 (s, 1H)<br>Three exchangeable protons |
| 20 | 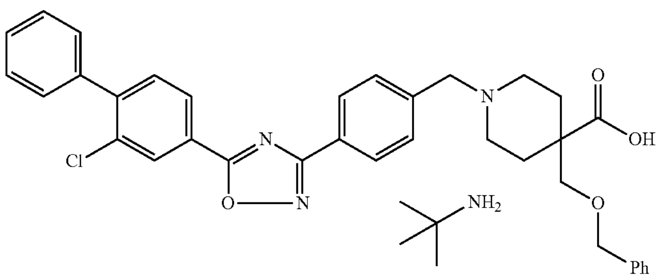 | 594.00 | as t-butyl amine salt<br>PMR: (CDCl₃; 500.13 MHz; δ ppm)<br>1.21 (s, 9H); 1.60-1.68 (br t, 2H); 2.17 (d, J = 13.45 Hz, 2H); 2.37-2.47 (br t, 2H); 2.71-2.78 (br d, 2H); 3.49 (s, 2H); 3.62 (s, 2H); 4.48 (s, 2H); 7.28-7.32 (m, 5H); 7.43-7.50 (m, 7H); 7.52 (d, J = 8.00 Hz, 1H); 8.09 (d, J = 8.20 Hz, 2H); 8.13 (dd, J₁ = 8.00 Hz, J₂ = 1.70 Hz, 1H); 8.32 (d, J = 1.50 Hz, 1H)<br>Three exchangeable protons |
| 21 | 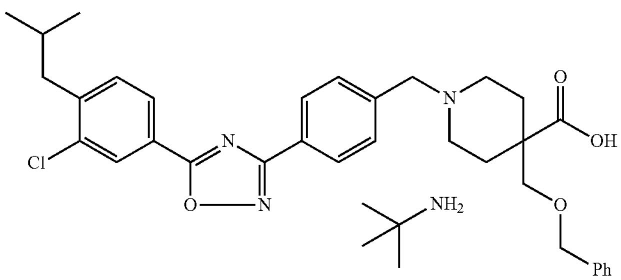 | 574.03 | as t-butyl amine salt<br>PMR: (CDCl₃ + CD₃OD + D₂O; 500.13 MHz; ppm)<br>0.96 (d, J = 6.60 Hz, 6H); 1.21 (s, 9H); 1.57-1.66 (br t, 2H); 1.98-2.07 (m, 1H); 2.15 (d, J = 13.15 Hz, 2H); 2.38-2.48 (br t, 2H); 2.66-2.75 (d merged in m, 4H); 3.49 (s, 2H); 3.61 (s, 2H); 4.47 (s, 2H); 7.23-7.31 (m, 5H); 7.35 (d, J = 8.10 Hz, 1H); 7.46 (d, J = 8.10 Hz, 2H); 7.99 (dd, J1 = 7.95 Hz, J2 = 1.15 Hz, 1H); 8.07 (d, J = 8.15 Hz, 2H); 8.19 (d, J = 1.45 Hz, 1H)<br>Three exchanaeable protons |
| 22 | 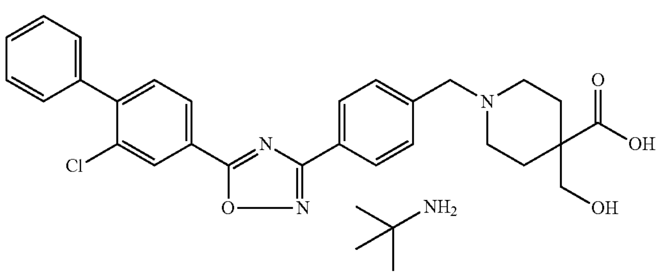 | 503.91 | as t-butyl amine salt<br>PMR: CDCl₃ + CD₃OD + TFA; 500.13 MHz; δ ppm)<br>1.38 (s, 9H); 1.87-1.97 (br t, 2H); 2.30 (d, J = 14.55 Hz, 2H); 2.99 (t, J = 12.50 Hz, 2H); 3.53 (d, J = 12.05 Hz, 2H); 3.65 (s, 2H); 4.26 (s, 2H); 7.43-7.50 (m, 5H); 7.56 (d, J = 8.00 Hz, 1H); 7.60 (d, J = 8.10 Hz, 2H); 8.16 (dd, J₁ = 8.00 Hz, J₂ = 1.35 Hz, 1H); 8.25 (d, J = 8.15 Hz, 2H); 8.35 (d, J = 1.50 Hz, 1H)<br>Four exchangeable protons |
| 23 | 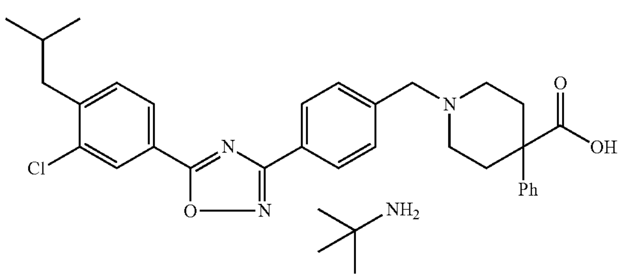 | 530.19 | as t-butyl amine salt<br>PMR: CDCl₃ + CD₃OD + TFA; 500.13 MHz; δ ppm)<br>0.98 (d, J = 6.65 Hz, 6H); 1.37 (s, 9H); 2.01-2.11 (m, 1H); 2.18-2.27 (br dt, 2H); 2.72 (d, J = 7.20 Hz, 2H); 2.81 (d, J = 13.90 Hz, 2H); 3.05 (t, J = 12.90 Hz, 2H); 3.65-3.72 (br d, 2H); 4.32 (s, 2H); 7.33-7.39 (m, 5H); 7.40 (d, J = 8.05 Hz, 1H); 7.60 (d, J = 8.20 Hz, 2H); 8.03 (dd, J₁ = 7.90 Hz, J₂ = 1.60 Hz, 1H); 8.20-8.27 (m, 3H)<br>Three exchangeable protons |

| Ex. No. | Structure | (MS) (ES+) | NMR data |
|---|---|---|---|
| 24 | 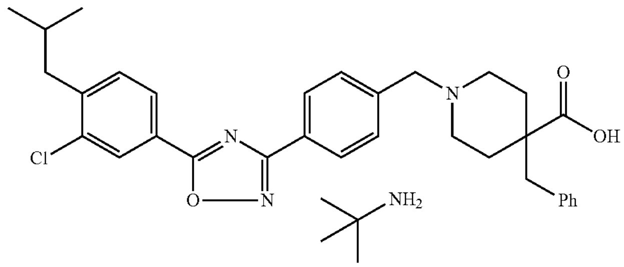 | 544.22 | as t-butyl amine salt<br>PMR: CDCl$_3$ + CD$_3$OD + TFA;<br>500.13 MHz; δ ppm)<br>0.86 (d, J = 6.50 Hz, 6H); 1.31 (s, 9H);<br>1.82-1.98 (m, 3H); 2.21-2.27 (br d, 2H);<br>2.61 (d, J = 7.15 Hz, 2H); 2.71-2.84 (s merged in m, 4H); 3.50-3.57 (br d, 2H);<br>4.17 (s, 2H); 6.92-6.98 (br d, 2H); 7.13-7.17 (br s, 3H); 7.29 (d, J = 7.95 Hz, 1H);<br>7.42 (d, J = 7.85 Hz, 2H); 7.90 (d, J = 7.80 Hz, 1H); 8.10 (d, J = 3.55 Hz, 3H)<br>Three exchangeable protons |
| 25 | 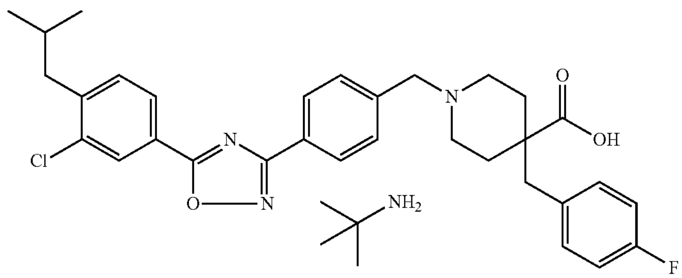 | 562.17 | as t-butyl amine salt<br>PMR: (CDCl$_3$ + CD$_3$OD + TFA;<br>500.13 MHz; δ ppm)<br>0.98 (d, J = 6.65 Hz, 6H); 1.40 (s, 9H);<br>1.83-1.93 (br dt, 2H); 2.02-2.10 (m, 1H);<br>2.30-2.35 (br d, 2H); 2.74 (d, J = 7.25 Hz, 2H); 2.88 (s, 2H); 2.96 (t, J = 13.05 Hz, 2H); 3.52-3.58 (br d, 2H); 4.28 (s, 2H);<br>6.96 (t, J = 8.65 Hz, 2H); 7.04-7.09 (m, 2H); 7.42 (d, J = 7.95 Hz, 1H); 7.57 (d, J = 8.20 Hz, 2H); 8.03 (dd, J$_1$ = 7.85 Hz, J$_2$ = 1.75 Hz, 1H); 8.20-8.24 (m, 3H)<br>Three exchangeable protons |
| 26 | 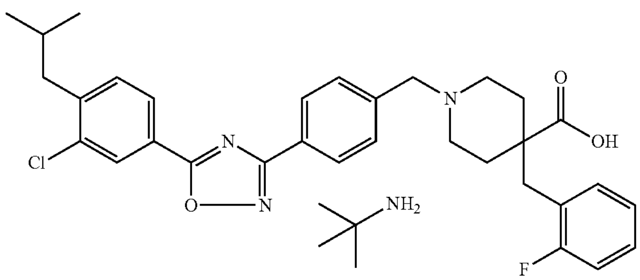 | 562.19 | as t-butyl amine salt<br>PMR: (CDCl$_3$ + CD$_3$OD; 500.13 MHz;<br>δ ppm)<br>0.97 (d, J = 6.60 Hz, 6H); 1.26 (s, 9H);<br>1.53-1.61 (br t, 2H); 2.01-2.13 (m, 3H);<br>2.22-2.28 (br t, 2H); 2.71 (d, J = 7.25 Hz, 2H); 2.77-2.84 (br d, 2H); 2.88 (s, 2H); 3.57 (s, 2H); 6.95-7.04 (m, 2H); 7.13-7.22 (m, 2H); 7.38 (d, J = 7.95 Hz, 1H); 7.46 (d, J = 8.15 Hz, 2H); 8.02 (dd, J$_1$ = 7.90 Hz, J$_2$ = 1.40 Hz, 1H); 8.08 (d, J = 8.15 Hz, 2H);<br>8.20 (d, J = 1.40 Hz, 1H)<br>Three exchangeable protons |
| 27 | 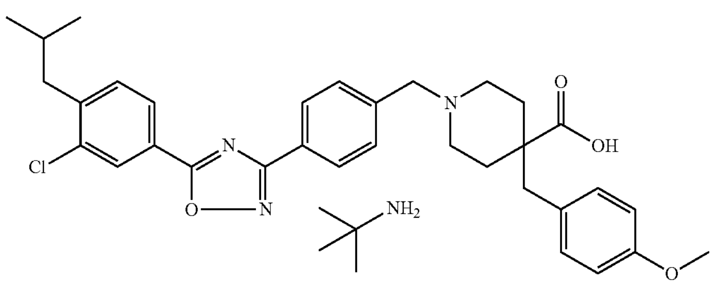 | 574.23 | as t-butyl amine salt<br>PMR: (CDCl$_3$ + CD$_3$OD + TFA;<br>500.13 MHz; δ ppm)<br>0.98 (d, J = 6.45 Hz, 6H); 1.37 (s, 9H);<br>1.82-1.91 (m, 2H); 2.03-2.10 (m, 1H);<br>2.27-2.34 (br d, 2H); 2.73 (d, J = 7.10 Hz, 2H); 2.84 (s, 2H); 2.88-2.97 (br t, 2H);<br>3.47-3.53 (br d, 2H); 3.78 (s, 3H); 4.25 (s, 2H); 6.81 (d, J = 8.35 Hz, 2H); 7.02 (d, J = 8.25 Hz, 2H); 7.40-7.44 (br d, 1H);<br>7.57 (d, J = 8.05 Hz, 2H); 8.03 (d, J = 7.90 Hz, 1H); 8.20-8.25 (br d, 3H)<br>Three exchangeable protons |
| 28 | 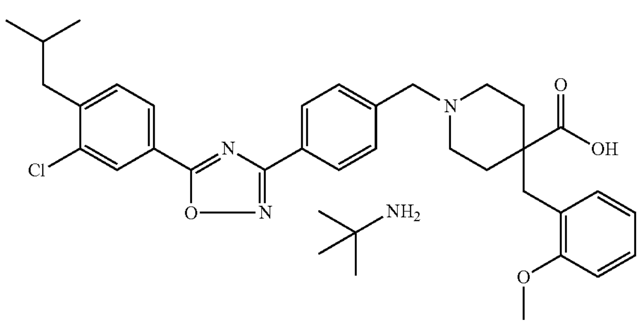 | 574.23 | as t-butyl amine salt<br>PMR: (CDCl$_3$ + CD$_3$OD; 500.13 MHz;<br>δ ppm)<br>0.97 (d, J = 6.55 Hz, 6H); 1.26 (s, 9H);<br>1.53-1.61 (br t, 2H); 2.01-2.10 (m, 3H);<br>2.20-2.26 (br t, 2H); 2.70 (d, J = 7.20 Hz, 2H); 2.78-2.82 (br d, 2H); 2.90 (s, 2H); 3.56 (s, 2H); 3.76 (s, 3H); 6.80-6.85 (m, 2H);<br>7.10-7.18 (m, 2H); 7.37 (d, J = 8.00 Hz, 1H); 7.45 (d, J = 8.05 Hz, 2H); 8.01 (d, J = 7.95 Hz, 1H); 8.08 (d, J = 8.00 Hz, 2H); 8.20 (s, 1H)<br>Three exchangeable protons |

| Ex. No. | Structure | (MS) (ES+) | NMR data |
|---|---|---|---|
| 29 | (structure) | 518.17 | as t-butyl amine salt<br>PMR: (CDCl$_3$ + CD$_3$OD; 400.13 MHz; δ ppm)<br>1.30 (s, 9H); 1.53-1.64 (br m, 2H); 2.10-2.18 (br d, 2H); 2.33-2.42 (br t, 2H); 2.74-2.82 (br d, 2H); 3.31 (s, 3H); 3.37-3.43 (br s, 2H); 3.64 (s, 2H); 7.42-7.53 (m, 7H); 7.53 (d, J = 10.31 Hz, 1H); 8.11-8.18 (m, 3H); 8.34 (d, J = 1.17 Hz, 1H)<br>Three exchangeable protons |
| 30 | (structure) | 502.19 | as t-butyl amine salt<br>PMR: (CDCl$_3$ + CD$_3$OD + TFA; 400.13 MHz; δ ppm)<br>0.88 (t, J = 7.34 Hz, 3H); 1.40 (s, 9H); 1.60-1.70 (m, 2H); 1.73-1.85 (br t, 2H); 2.37 (d, J = 14.65 Hz, 2H); 2.93 (t, J = 12.51 Hz, 2H); 3.57 (d, J = 12.32 Hz, 2H); 4.29 (s, 2H); 7.43-7.54 (br m, 4H); 7.56-7.62 (m, 3H); 8.23-8.28 (br d, 2H); 8.34-8.37 (br s, 1H)<br>Two protons are merged between 8.1-8.2, Three exchangeable protons |
| 31 | (structure) | 434.18 | as t-butyl amine salt<br>PMR: (CDCl$_3$ + CD$_3$OD; 500.13 MHz; δ ppm)<br>0.93 (d, J = 6.50 Hz, 6H); 1.16 (s, 3H); 1.28 (s, 9H); 1.46-1.55 (br m, 2H); 1.89-1.99 (m, 1H); 2.09-2.15 (br d, 2H); 2.31-2.39 (br t, 2H); 2.58 (d, J = 7.25 Hz, 2H); 2.70-2.78 (br d, 2H); 3.64 (s, 2H); 7.34 (d, J = 7.15 Hz, 2H); 7.48 (d, J = 8.15 Hz, 2H); 8.09-8.14 (m, 4H)<br>Three exchangeable protons |
| 32 | (structure) | 540.23 | as t-butyl amine salt<br>PMR: (CDCl$_3$ + CD$_3$OD; 500.13 MHz; δ ppm)<br>0.97 (d, J = 6.56 Hz, 6H); 1.26 (s, 9H); 1.29-1.36 (br m, 2H); 1.41-1.58 (m, 6H); 2.00-2.09 (m, 1H); 2.11-2.18 (br d, 2H); 2.21-2.29 (br t, 2H); 2.71 (d, J = 7.19 Hz, 2H); 2.74-2.81 (br d, 2H); 3.31 (s, 3H); 3.36-3.40 (br m, 2H); 3.59 (s, 2H); 7.39 (d, J = 8.02 Hz, 1H); 7.47 (d, J = 8.04 Hz, 2H); 8.02 (d, J = 6.90 Hz, 1H); 8.10 (d, J = 8.04 Hz, 2H); 8.21 (s, 1H)<br>Three exchangeable protons |
| 33 | (structure) | 542.04 | As potassium salt:<br>PMR: (CDCl$_3$ + CD$_3$OD; 500.13 MHz; δ ppm)<br>0.96 (d, J = 6.60 Hz, 6H); 1.39-1.46 (br t, 2H); 2.00-2.09 (m, 1H); 2.10-2.16 (br d, 2H); 2.22-2.30 (br t, 2H); 2.65-2.72 (d merged in m, 4H); 3.35 (s, 3H); 3.43 (s, 2H); 3.50-3.56 (m, 6H); 7.37 (d, J = 7.95 Hz, 1H); 7.46 (d, J = 8.05 Hz, 2H); 8.01 (dd, J$_1$ = 7.90 Hz, J$_2$ = 1.45 Hz, 1H); 8.09 (d, J = 8.10 Hz, 2H); 8.20 (d, J = 1.40 Hz, 1H) |

| Ex. No. | Structure | (MS) (ES+) | NMR data |
|---|---|---|---|
| 34 | 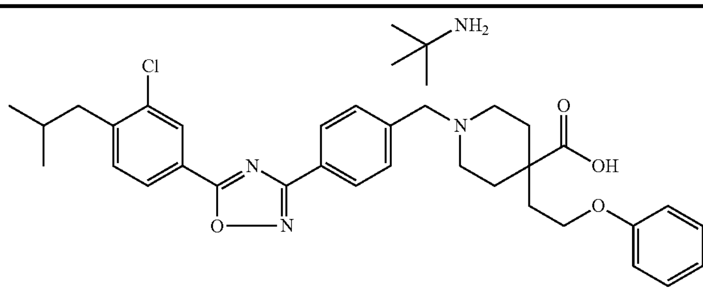 | 574.21 | as t-butyl amine salt<br>PMR: (CDCl$_3$ + CD$_3$OD + TFA; 400.13 MHz; δ ppm)<br>0.96 (d, J = 6.53 Hz, 6H); 1.41 (s, 9H); 1.86-1.98 (br t, 2H); 1.98-2.10 (m, 1H); 2.13-2.20 (br t, 2H); 2.50-2.58 (br d, 2H); 2.71 (d, J = 7.16 Hz, 2H); 3.06 (t, J = 13.04 Hz, 2H); 3.60-3.67 (br d, 2H); 4.02-4.09 (br t, 2H); 4.33 (s, 2H); 6.78 (d, J = 8.13 Hz, 2H); 6.95 (t, J = 7.27 Hz, 1H); 7.21-7.27 (br t, 2H); 7.41 (d, J = 8.01 Hz, 1H); 7.56 (d, J = 7.84 Hz, 2H); 8.00 (d, J = 7.87 Hz, 1H); 8.16-8.22 (m, 3H)<br>Three exchangeable protons |
| 35 | 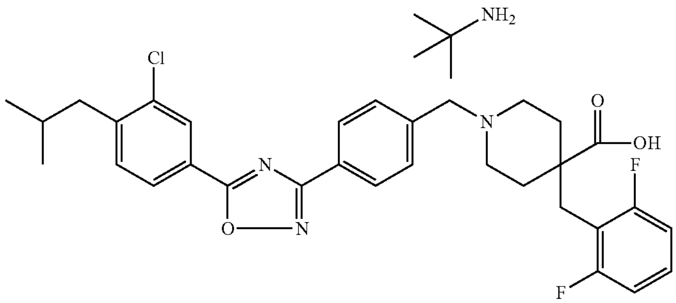 | 580.18 | as t-butyl amine salt<br>PMR: (CDCl$_3$ + CD$_3$OD; 500.13 MHz; δ ppm)<br>0.97 (d, J = 6.55 Hz, 6H); 1.28 (s, 9H); 1.49-1.57 (br t, 2H); 2.00-2.07 (m, 1H); 2.12-2.22 (m, 4H); 2.70 (d, J = 7.15 Hz, 2H); 2.80-2.85 (br d, 2H); 2.90 (s, 2H); 3.55 (s, 2H); 6.83 (t, J = 7.40 Hz, 2H); 7.11-7.19 (m, 1H); 7.38 (d, J = 8.00 Hz, 1H); 7.44 (d, J = 8.00 Hz, 2H); 8.01 (dd, J$_1$ = 7.90 Hz, J2 = 1.40 Hz, 1H); 8.07 (d, J = 8.00 Hz, 2H); 8.20 (s, 1H)<br>Three exchangeable protons |
| 36 | 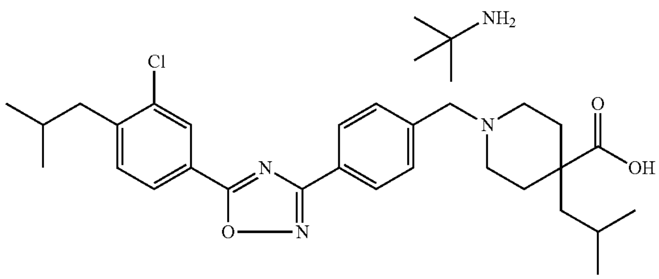 | 510.28 | as t-butyl amine salt<br>PMR: (CDCl$_3$ + CD$_3$OD; 500.13 MHz; δ ppm)<br>0.89 (d, J = 6.65 Hz, 6H); 0.97 (d, J = 6.60 Hz, 6H); 1.30 (s, 9H); 1.46 (d, J = 5.85 Hz, 2H); 1.48-1.56 (m, 2H); 1.68-1.77 (m, 1H); 2.00-2.09 (m, 1H); 2.12-2.09 (br d, 2H); 2.27-2.35 (br t, 2H); 2.71 (d, J = 7.20 Hz, 2H); 2.75-2.81 (br d, 2H); 3.61 (s, 2H); 7.39 (d, J = 8.00 Hz, 1H); 7.49 (d, J = 8.15 Hz, 2H); 8.02 (dd, J$_1$ = 7.95 Hz, J$_2$ = 1.60 Hz, 1H); 8.11 (d, J = 8.10 Hz, 2H); 8.21 (d, J = 1.45 Hz, 1H)<br>Three exchangeable protons |
| 37 | 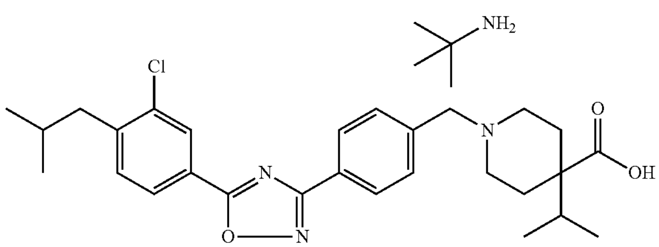 | 496.28 | as t-butyl amine salt<br>PMR: (CDCl$_3$ + CD$_3$OD + TFA; 500.13 MHz; δ ppm)<br>0.94 (d, J = 6.80 Hz, 6H); 0.97 (d, J = 6.60 Hz, 6H); 1.43 (s, 9H); 1.83-1.92 (m, 1H); 1.95-2.10 (m, 3H); 2.33 (d, J = 14.25 Hz, 2H); 2.72 (d, J = 7.20 Hz, 2H); 2.83-2.94 (br t, 2H); 3.57-3.64 (br d, 2H); 4.29 (s, 2H); 7.40 (d, J = 8.00 Hz, 1H); 7.62-7.66 (br d, 2H); 8.01 (dd, J$_1$ = 7.95 Hz, J$_2$ = 1.55 Hz, 1H); 8.20-8.24 (br m, 3H)<br>Three exchangeable protons |
| 38 | 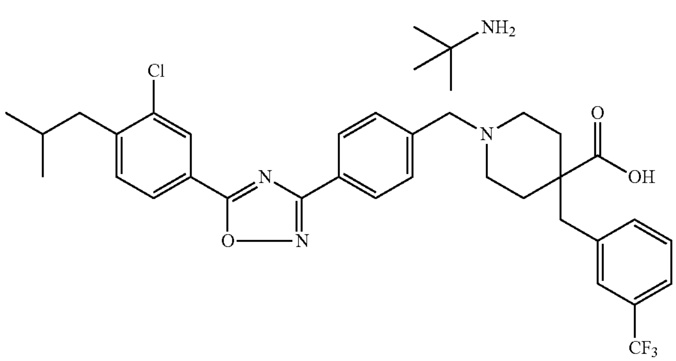 | 612.20 | as t-butyl amine salt<br>PMR: (CDCl$_3$ + CD$_3$OD + TFA; 500.13 MHz; δ ppm)<br>0.98 (d, J = 6.60 Hz, 6H); 1.42 (s, 9H); 1.96-2.10 (m, 3H); 2.31 (d, J = 14.50 Hz, 2H); 2.71 (d, J = 7.20 Hz, 2H); 2.85 (t, J = 12.25 Hz, 2H); 2.98 (s, 2H); 3.59-3.65 (br d, 2H); 4.26 (s, 2H); 7.26-7.33 (m, 1H); 7.35-7.37 (br s, 1H); 7.38-7.44 (m, 2H); 7.51-7.56 (br d, 3H); 8.02 (dd, J$_1$ = 7.90 Hz, J$_2$ = 1.25 Hz, 1H); 8.20-8.25 (br d, 3H)<br>Three exchangeable protons |

-continued

| Ex. No. | Structure | (MS) (ES+) | NMR data |
|---|---|---|---|
| 39 | 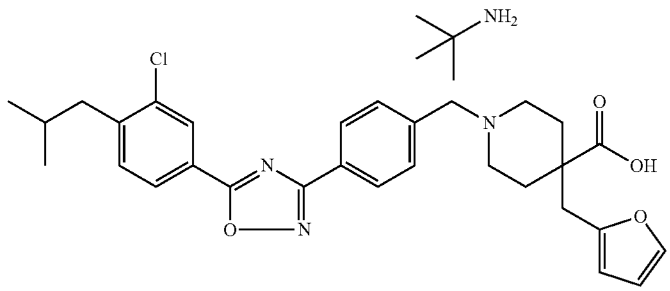 | 534.14 | as t-butyl amine salt<br>PMR: (CDCl$_3$ + CD$_3$OD; 500.13 MHz; δ ppm)<br>0.97 (d, J = 6.60 Hz, 6H); 1.26 (s, 9H); 1.54-1.62 (br t, 2H); 2.00-2.08 (m, 1H); 2.08-2.14 (br d, 2H); 2.27-2.36 (br t, 2H); 2.71 (d, J = 7.25 Hz, 2H); 2.73-2.79 (br d, 2H); 2.87 (s, 2H); 3.38 (s, 2H); 6.04 (d, J = 3.05 Hz, 1H); 6.23-6.27 (m, 1H); 7.27 (d, J = 0.95 Hz, 1H); 7.38 (d, J = 7.95 Hz, 1H); 7.47 (d, J = 8.10 Hz, 2H); 8.02 (dd, J$_1$ = 7.95 Hz, J$_2$ = 1.55 Hz, 1H); 8.09 (d, J = 8.15 Hz, 2H), 8.21 (d, J = 1.30 Hz, 1H)<br>Three exchangeable protons |
| 40 | 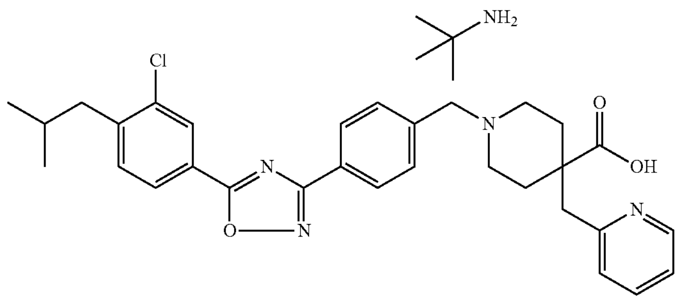 | 545.13 | as t-butyl amine salt<br>PMR: (CDCl$_3$ + CD$_3$OD; 500.13 MHz; δ ppm)<br>0.97 (d, J = 6.50 Hz, 6H); 1.27 (s, 9H); 1.54-1.62 (br t, 2H); 2.00-2.08 (m, 1H); 2.08-2.14 (br d, 2H); 2.29-2.38 (br t, 2H); 2.70 (d, J = 7.25 Hz. 2H); 2.75-2.83 (br d, 2H); 3.00 (s, 2H); 3.61 (s, 2H); 7.14-7.19 (m, 1H); 7.23 (d, J = 7.80 Hz, 1H); 7.38 (d, J = 7.95 Hz, 1H); 7.46 (d, J = 8.10 Hz, 2H); 7.62 (dt, J$_1$ = 7.75 Hs, J$_2$ = 1.45 Hz, 1H); 8.01 (dd, J$_1$ = 7.85 Hz, J$_2$ = 1.30 Hz, 1H); 8.09 (d, J = 8.15 Hz, 2H); 8.20-8.22 (br s, 1H); 8.39-8.42 (br d, 1H)<br>Three exchangeable protons |
| 41 | 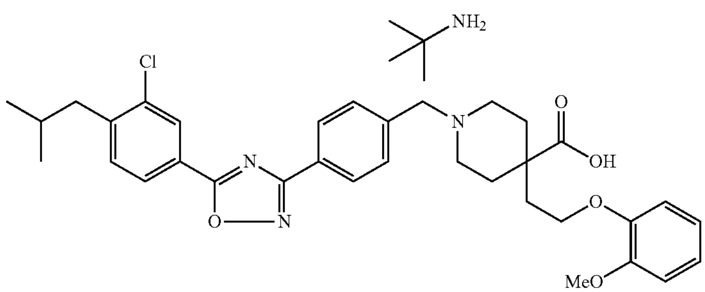 | 604.12 | as t-butyl amine salt<br>PMR: (CDCl$_3$ + CD$_3$OD; 500.13 MHz; δ ppm)<br>0.97 (d, J = 6.60 Hz, 6H); 1.28 (s, 9H); 1.56-1.66 (br m, 2H); 2.00-2.10 (m, 3H); 2.16-2.23 (br d, 2H); 2.29-2.37 (br t, 2H); 2.71 (d, J = 7.25 Hz, 2H); 2.74-2.82 (br d, 2H); 3.61 (s, 2H); 3.83 (s, 3H); 4.08 (t, J = 7.65 Hz, 2H); 6.84-6.92 (m, 4H); 7.38 (d, J = 7.95 Hz, 1H); 7.48 (d, J = 8.05 Hz, 2H); 8.01 (dd, J$_1$ = 7.90 Hz, J$_2$ = 1.10 Hz, 1H); 8.10 (d, J = 8.05 Hz, 2H); 8.20 (d, J = 1.00 Hz, 1H)<br>Three exchangeable protons |
| 42 | 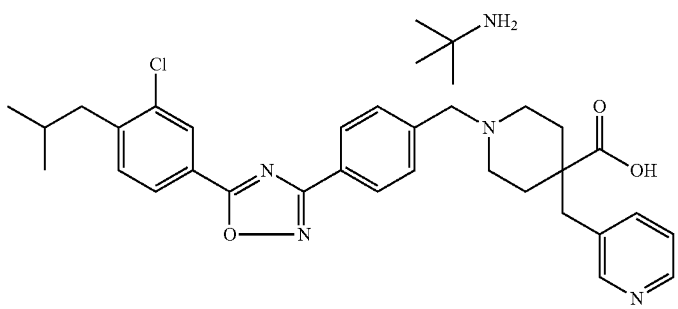 | 545.16 | as t-butyl amine salt<br>PMR: (Pyridine-d$_5$; 500.13 MHz; δ ppm)<br>0.90 (d, J = 6.60 Hz, 6H); 1.23 (s, 9H); 1.72-1.81 (m, 2H); 1.92-2.02 (m, 1H); 2.39-2.51 (br m, 4H); 2.62 (d, J = 7.25 Hz, 2H); 2.81-2.89 (br m, 2H); 3.05 (s, 2H); 3.53 (s, 2H); 7.17-7.21 (m, 1H); 7.36 (d, J = 7.95 Hz, 1H); 7.64 (d, J = 8.05 Hz, 2H); 7.67-7.70 (br d, 1H); 8.08 (dd, J$_1$ = 7.95 Hz, J$_2$ = 1.65 Hz, 1H); 8.32 (d, J = 1-60 Hz, 1H); 8.40 (d, J = 8.05 Hz, 2H); 8.61-8.64 (br m, 1H); 8.82-8.85 (br d, 1H)<br>Three exchangeable protons |
| 43 | 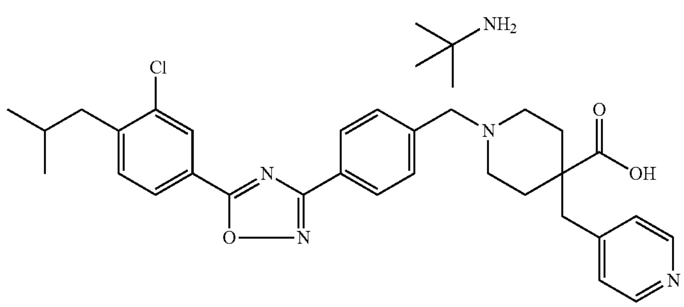 | 545.14 | as t-butyl amine salt<br>PMR: (Pyridine-d$_5$; 500.13 MHz; δ ppm)<br>0.90 (d, J = 6.65 Hz, 6H); 1.21 (s, 9H); 1.72-1.81 (m, 2H); 1.92-2.02 (m, 1H); 2.39-2.47 (br d, 2H); 2.49 (t, J = 11.10 Hz, 2H); 2.62 (d, J = 7.25 Hz, 2H); 2.82-2.89 (br m, 2H); 3.04 (s, 2H); 3.54 (s, 2H); 7.32 (d, J = 5.80 Hz, 2H); 7.37 (d, J = 8.00 Hz, 1H); 7.65 (d, J = 8.05 Hz, 2H); 8.08 (dd, J$_1$ = 7.85 Hz, J$_2$ = 1.50 Hz, 1H); 8.32 (d, J = 1.45 Hz, 1H); 8.40 (d, J = 8.00 Hz, 2H); 8.67 (d, J = 5.70 Hz, 2H);<br>Three exchangeable protons |

| Ex. No. | Structure | (MS) (ES+) | NMR data |
|---|---|---|---|
| 44 | 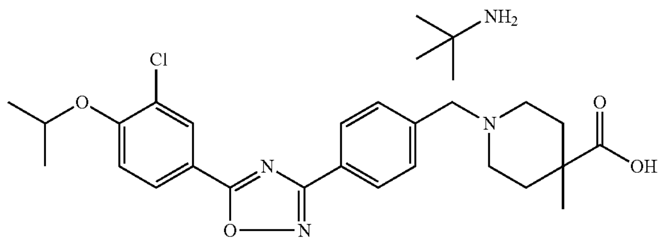 | 470.11 | as t-butyl amine salt<br>PMR: (CDCl₃ + CD₃OD; 500.13 MHz; δ ppm)<br>1.18 (s, 3H); 1.26 (s, 9H); 1.45 (d, J = 6.05 Hz, 6H); 1.47-1.53 (br m, 2H); 2.09-2.16 (br d, 2H); 2.27-2.36 (br t, 2H); 2.68-2.76 (br d, 2H); 3.60 (s, 2H); 4.74 (quintet, J = 6.10 Hz, 1H); 7.09 (d, J = 8.80 Hz, 1H); 7.47 (d, J = 8.10 Hz, 2H); 8.06-8.12 (m, 3H); 8.23 (d, J = 2.00 Hz, 1H);<br>Three exchangeable protons |
| 45 | 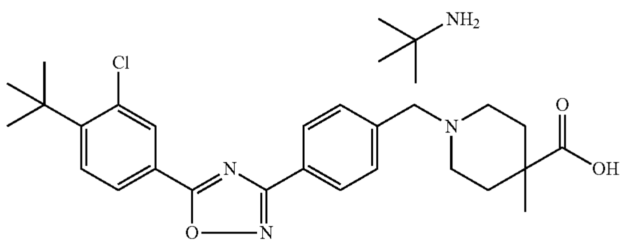 | 468.11 | as t-butyl amine salt<br>PMR: (CDCl₃ + CD₃OD; 500.13 MHz; δ ppm)<br>1.16 (s, 3H); 1.28 (s, 9H); 1.46-1.54 (m, 2H); 1.54 (s, 9H); 2.08-2.16 (br d, 2H); 2.30-2.38 (br t, 2H); 2.70-2.77 (br s, 2H); 3.63 (s, 2H); 7.49 (d, J = 8.15 Hz, 2H); 7.63 (d, J = 8.35 Hz, 1H); 8.02 (dd, J₁ = 8.30 Hz, J₂ = 1.75 Hz, 1H); 8.11 (d, J = 8.05 Hz, 2H); 8.19 (d, J = 1.80 Hz, 1H)<br>Three exchangeable protons |
| 46 | 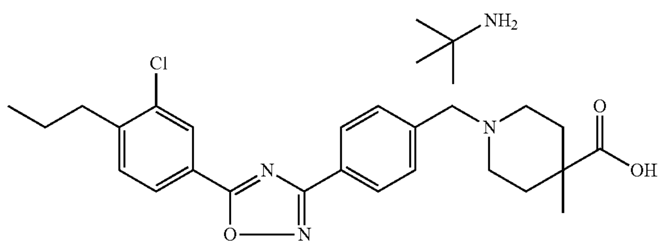 | 454.12 | as t-butyl amine salt<br>PMR: (CDCl₃ + CD₃OD; 200.13 MHz; δ ppm)<br>1.02 (t, J = 7.26 Hz, 3H); 1.17 (s, 3H); 1.27 (s, 9H); 1.40-1.58 (br m, 2H); 1.61-1.81 (m, 2H); 2.03-2.19 (br d, 2H); 2.23-2.40 (br t, 2H); 2.62-2.87 (br m, 4H); 3.61 (s, 2H); 7.42 (d, J = 8.08 Hz, 1H); 7.48 (d, J = 8.26 Hz, 2H); 8.02 (d, J₁ = 7.94 Hz J₂ = 1.72 Hz, 1H); 8.10 (d, J = 8.20 Hz, 2H); 8.20 (d, J = 1.68 Hz, 1H)<br>Three exchangeable protons |
| 47 | 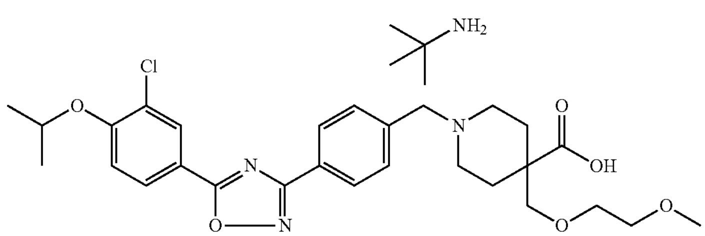 | 544.15 | as t-butyl amine salt<br>PMR: (CDCl₃ + CD₃OD + D₂O; 200.13 MHz; δ ppm)<br>1.29 (s, 9H); 1.45 (d, J = 6.02 Hz, 6H); 1.50-1.63 (br d, 2H); 2.06-2.21 (br d, 2H); 2.28-2.44 (br t, 2H); 2.63-2.79 (br d, 2H); 3.35 (s, 3H); 3.44-3.62 (two singlets merged in triplet, 8H); 4.73 (septate, J = 6.08 Hz, 1H); 7.08 (d, J = 8.84 Hz, 1H); 7.48 (d, J = 8.16 Hz, 2H); 8.02-8.13 (m, 3H); 8.22 (d, J = 2.10 Hz, 1H);<br>Three exchangeable protons |
| 48 | 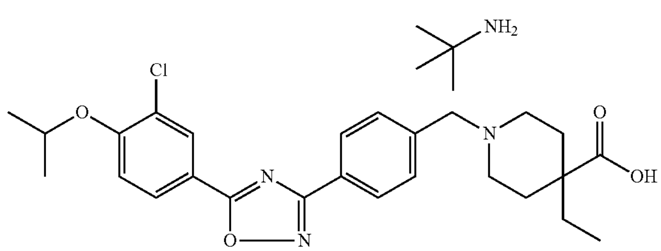 | 484.16 | as t-butyl amine salt<br>PMR: (CDCl₃ + CD₃OD; 200.13 MHz; δ ppm)<br>0.85 (t, J = 7.32 Hz, 3H); 1.26 (s, 9H); 1.43 (d, J = 6.02 Hz, 6H); 1.49-1.61 (m, 4H); 2.03-2.20 (br d, 2H); 2.20-2.36 (br t, 2H); 2.70-2.86 (br d, 2H); 3.60 (s, 2H); 4.74 (pentate, J = 5.92 Hz, 1H); 7.09 (d, J = 8.74 Hz, 1H); 7.47 (d, J = 8.16 Hz, 2H); 8.03-8.13 (m, 3H); 8.23 (d, J = 2.10 Hz, 1H)<br>Three exchangeable protons |

| Ex. No. | Structure | (MS) (ES+) | NMR data |
|---|---|---|---|
| 49 | 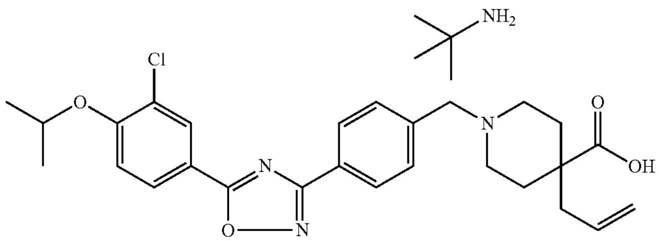 | 496.12 | as t-butyl amine salt<br>PMR: (CDCl$_3$ + CD$_3$OD; 200.13 MHz; δ ppm)<br>1.26 (s, 9H); 1.45 (d, J = 6.04 Hz, 6H); 1.49-1.62 (br d, 2H); 2.03-2.18 (br d, 2H); 2.23-2.39 (br m, 4H); 2.71-2.83 (br m, 2H); 3.62 (s, 2H); 4.72 (pentate, J = 6.10 Hz, 1H); 4.95-5.01 (br s, 1H); 5.01-5.10 (br d, 1H); 5.66-5.90 (m, 1H); 7.06 (d, J = 8.90 Hz, 1H); 7.48 (d, J = 8.24 Hz, 2H); 8.01-8.13 (m, 3H); 8.22 (d, J = 2.14 Hz, 1H);<br>Three exchangeable protons |
| 50 | 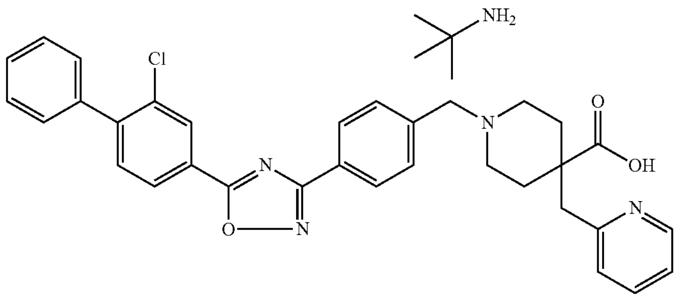 | 565.12 | as t-butyl amine salt<br>PMR: (CDCl$_3$ + CD$_3$OD; 200.13 MHz; δ ppm)<br>1.28 (s, 9H); 1.50-1.69 (br m, 2H); 2.01-2.18 (br d, 2H); 2.23-2.42 (br t, 2H); 2.73-2.87 (br d, 2H); 3.00 (s, 2H); 3.61 (s, 2H); 7.12-7.27 (m, 2H); 7.42-7.53 (br m, 7H); 7.55 (d, J = 8.04 Hz, 1H); 7.63 (dt, J$_1$ = 7.68 Hz, J$_2$ = 1.82 Hz, 1H); 8.07-8.19 (m, 3H); 8.34 (d, J = 1.64 Hz, 1H); 8.38-8.44 (br d, 1H)<br>Three exchangeable protons |
| 51 | 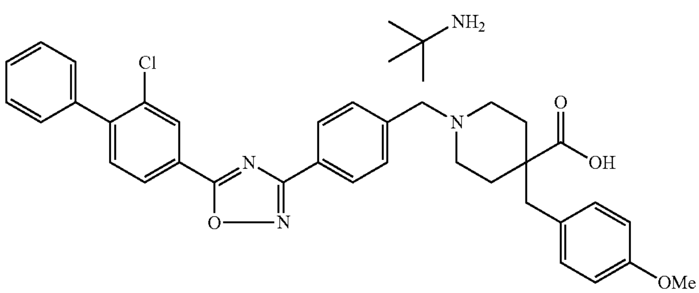 | 594.12 | as t-butyl amine salt<br>PMR: (CDCl$_3$ + CD$_3$OD + TFA; 500.13 MHz; δ ppm)<br>1.42 (s, 9H); 1.84-1.94 (br t, 2H); 2.33-2.40 (br d, 2H); 2.87 (s, 2H); 2.94-3.02(br t, 2H); 3.57-3.63 (br d, 2H); 3.80 (s, 3H);4.30 (s, 3H); 6.83 (d, J = 8.50 Hz, 2H); 7.01 (d, J = 8.50 Hz, 2H); 7.44-7.50 (m, 1H); 7.50-7.54 (m, 3H); 7.56 (d, J = 8.10 Hz, 2H); 7.60 (d, J = 8.00 Hz, 1H); 8.17 (dd, J$_1$ = 8.05 Hz, J$_2$ = 1.40 Hz, 1H); 8.23 (d, J = 8.15 Hz, 2H); 8.35 (d, J = 1.40 Hz, 1H)<br>Three exchangeable protons |
| 52 | 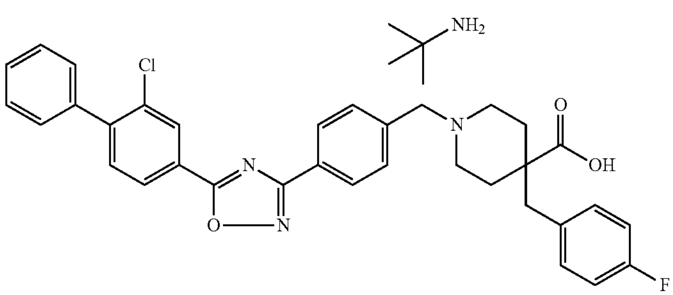 | 582.08 | as t-butyl amine salt<br>PMR: (CDCl$_3$ + CD$_3$OD; 400.13 MHz; δ ppm)<br>1.18 (s, 9H); 1.42-1.52 (br t, 2H); 1.98 (d, J = 13.14 Hz, 2H); 2.18-2.28 (br t, 2H); 2.68-2.78 (s merged in m, 4H); 3.52 (s, 2H); 6.83 (t, J = 8.61 Hz, 2H); 7.00-7.07 (m, 2H); 7.34-7.45 (m, 7H); 7.47 (d, J = 8.01 Hz, 1H); 8.03 (d, J = 7.99 Hz, 2H); 8.07 (d, J = 8.58 Hz, 1H); 8.26 (s, 1H)<br>Three exchangeable protons |
| 53 | 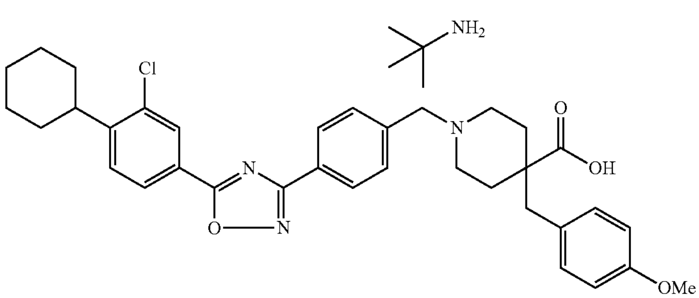 | 600.12 | as t-butyl amine salt<br>PMR: (CDCl$_3$ + CD$_3$OD + TFA; 400.13 MHz; δ ppm)<br>1.25-1.55 (s merged in m, 15H); 1.78-1.97 (m, 6H); 2.27 (d, J = 14.32 Hz, 2H); 2.81-2.91 (s merged in m, 4H); 3.07-3.16 (br t, 1H); 3.49-3.56 (br d, 2H); 3.77 (s, 3H); 4.23 (s, 2H); 6.79 (d, J = 8.37 Hz, 2H); 7.48 (d, J = 8.17 Hz, 1H); 7.54 (d, J = 8.03 Hz, 2H); 8.05 (d, J = 8.03 Hz, 1H); 8.19-8.25 (s merged in d, 3H)<br>Two protons are merged between 6.94-7.03<br>Three exchangeable protons |

-continued

| Ex. No. | Structure | (MS) (ES+) | NMR data |
|---|---|---|---|
| 54 | 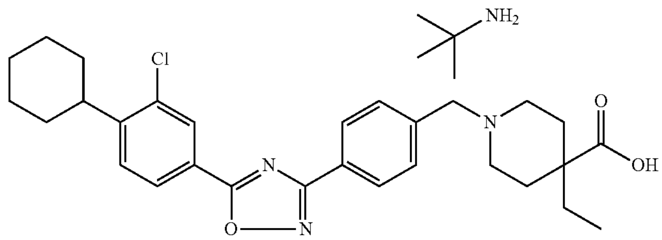 | 508.07 | as t-butyl amine salt<br>PMR: (Pyridine-d$_5$; 400.13 MHz; δ ppm)<br>1.01 (t, J = 7.38 Hz, 3H); 1.17 (s, 9H); 1.27-1.43 (br m, 5H); 1.60-1.71 (br m, 3H) 1.71-1.80 (br m, 5H); 1.80-1.86 (br d, 2H); 2.42-2.52 (br t, 2H); 2.78-2.87 (br d, 2H); 3.03-3.12 (br t, 1H); 3.53 (s, 2H); 7.47 (d, J = 8.13 Hz, 1H); 7.65 (d, J = 7.92 Hz, 2H); 8.14 (d, J = 8.10 Hz, 1H); 8.32 (s, 1H); 8.39 (d, J = 8.00 Hz, 2H)<br>Three exchangeable protons |
| 55 | 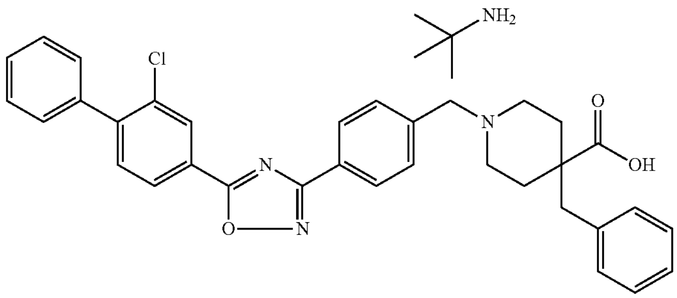 | 564.12 | as t-butyl amine salt<br>PMR: (CDCl$_3$ + CD$_3$OD; 500.13 MHz; δ ppm)<br>1.26 (s, 9H); 1.53-1.61 (br t, 2H); 2.05-2.12 (br d, 2H); 2.22-2.29 (br t, 2H); 2.76-2.83 (br d, 2H); 2.84 (s, 2H); 3.58 (s, 2H); 7.13-7.20 (m, 3H); 7.20-7.25 (m, 2H); 7.43-7.53 (m, 7H); 7.56 (d, J = 8.00 Hz, 1H); 8.11 (d, J = 8.05 Hz, 2H); 8.16 (dd, J$_1$ = 7.95 Hz, J$_2$ = 1.45 Hz, 1H); 8.34 (d, J = 1.30 Hz, 1H)<br>Three exchangeable protons |
| 56 | 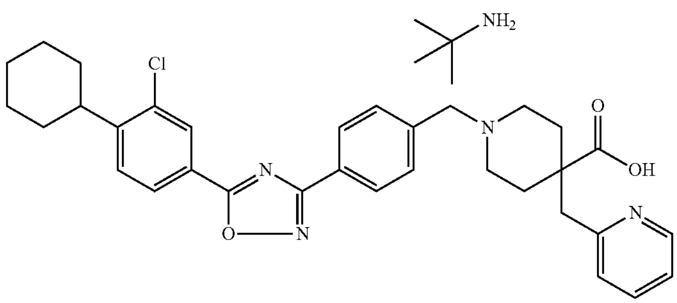 | 571.15 | as t-butyl amine salt<br>PMR: (Pyridine-d$_5$; 400.13 MHz; δ ppm)<br>1.18 (s, 9H); 1.27-1.40 (br m, 5H); 1.63-1.71 (br d, 1H); 1.71-1.87 (br m, 4H); 1.91-2.12 (br t, 2H); 2.48-2.58 (br t, 4H); 2.82-2.92 (br d, 2H); 3.03-3.12 (br t, 1H); 3.39 (s, 2H); 3.53 (s, 2H); 7.04-7.10 (m, 1H); 7.35 (d, J = 7.71 Hz, 1H); 7.47 (d, J = 8.17 Hz, 1H); 7.52 (t, J = 7.63 Hz, 1H); 7.62 (d, J = 7.95 Hz, 2H); 8.15 (d, J = 7.19 Hz, 1H); 8.32 (d, J = 1.12 Hz, 1H); 8.37 (d, J = 8.00 Hz, 2H); 8.65 (d, J = 3.80 Hz, 1H)<br>Three exchangeable protons |
| 57 | 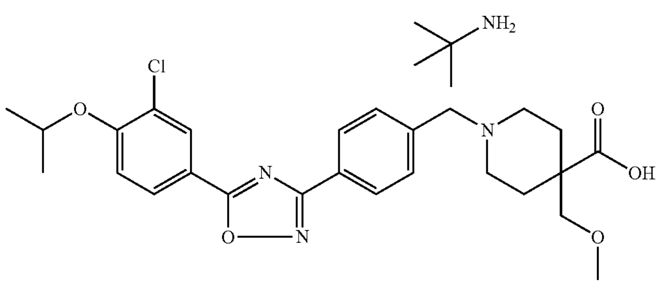 | 500.12 | as t-butyl amine salt<br>PMR: (CDCl$_3$ + CD$_3$OD; 400.13 MHz; δ ppm)<br>1.26 (s, 9H); 1.45 (d, J = 6.00 Hz, 6H); 1.53-1.61 (m, 2H); 2.10-2.17 (br d, 2H); 2.35 (t, J = 10.90 Hz, 2H); 2.72-2.81 (br d, 2H); 3.31 (s, 3H); 3.40 (s, 2H); 3.62 (s, 2H); 4.75 (septate, J = 6.10 Hz, 1H); 7.10 (d, J = 8.85 Hz, 1H); 7.48 (d, J = 8.20 Hz, 2H); 8.06-8.12 (m, 3H); 8.23 (d, J = 1.95 Hz, 1H)<br>Three exchangeable protons |
| 58 | 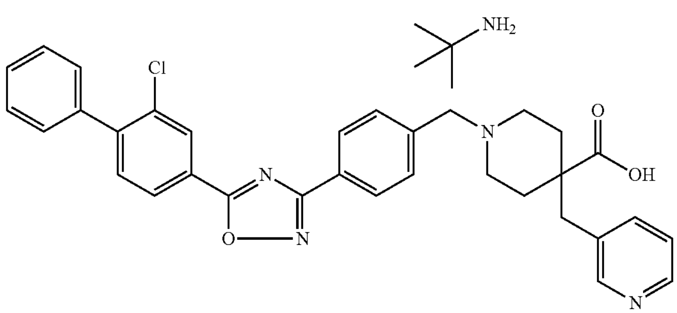 | 565.11 | as t-butyl amine salt<br>PMR: (Pyridine-d$_5$; 500.13 MHz; δ ppm)<br>1.15 (s, 9H); 1.77 (t, J = 10.85 Hz, 2H); 2.40-2.47 (br m, 4H); 2.84-2.87 (br d, 2H); 3.04 (s, 2H); 3.53 (s, 2H); 7.18-7.20 (br m, 1H); 7.45-7.60 (br m, 6H); 7.64-7.68 (br m, 3H); 8.20 (dd, J$_1$ = 7.95 Hz, J$_2$ = 1.7 Hz, 1H); 8.41-8.45 (br m, 3H); 8.63 (dd, J$_1$ = 4.75 Hz, J$_2$ = 1.55 Hz, 1H); 8.83 (d, J = 1.75 Hz, 1H)<br>Three exchangeable protons |

| Ex. No. | Structure | (MS) (ES+) | NMR data |
|---|---|---|---|
| 59 | 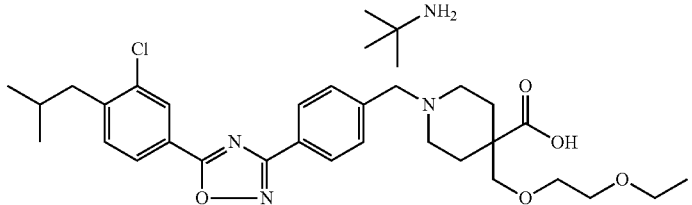 | 556.18 | as t-butyl amine salt<br>PMR: (CDCl₃ + CD₃OD; 500.13 MHz; δ ppm)<br>0.97 (d, J = 6.60 Hz, 6H); 1.19 (t, J = 7.05 Hz, 3H); 1.29 (s, 9H); 1.53-1.62 (br t, 2H); 2.00-2.10 (m, 1H); 2.10-2.16 (br d, 2H); 2.36 (t, J = 10.85 Hz, 2H); 2.71 (d, J = 7.25 Hz, 2H); 2.73-2.80 (br d, 2H); 3.48 (s, 2H); 3.53 (q, J = 7.05 Hz, 2H); 3.55-3.58 (br s, 4H); 3.62 (s, 2H); 7.39 (d, J = 8.00 Hz, 1H); 7.49 (d, J = 8.05 Hz, 2H); 8.02 (d, J = 7.95 Hz, 1H); 8.10 (d, J = 8.10 Hz, 2H); 8.21 (d, J = 1.10 Hz, 1H)<br>Three exchangeable protons |
| 60 | 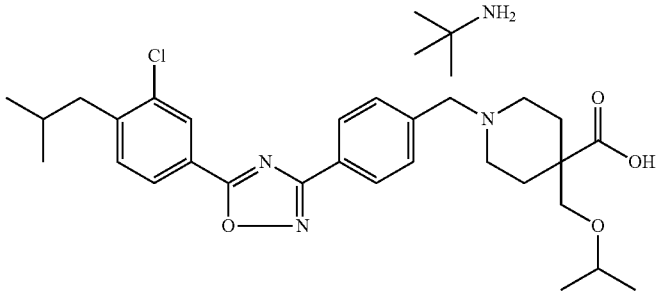 | 526.18 | as t-butyl amine salt<br>PMR: (CDCl₃ + CD₃OD; 400.13 MHz; δ ppm)<br>0.97 (d, J = 6.64 Hz, 6H); 1.10 (d, J = 6.08 Hz, 6H); 1.27 (s, 9H); 1.56-1.66 (br m, 2H); 1.99-2.08 (m, 1H); 2.07-2.14 (br d, 2H); 2.30-2.39 (br t, 2H); 2.71 (d, J = 7.20 Hz, 2H); 2.73-2.80 (br d, 2H); 3.38 (pentate, J = 1.64 Hz, 1H); 3.44 (s, 2H); 3.61 (s, 2H); 7.38 (d, J = 8.00 Hz, 1H); 7.48 (d, J = 8.24 Hz, 2H); 8.02 (dd, J₁ = 7.92 Hz, J₂ = 1.72 Hz, 1H); 8.10 (d, J = 8.24 Hz, 2H); 8.21 (d, J = 1.68 Hz, 1H)<br>Three exchangeable protons |
| 61 | 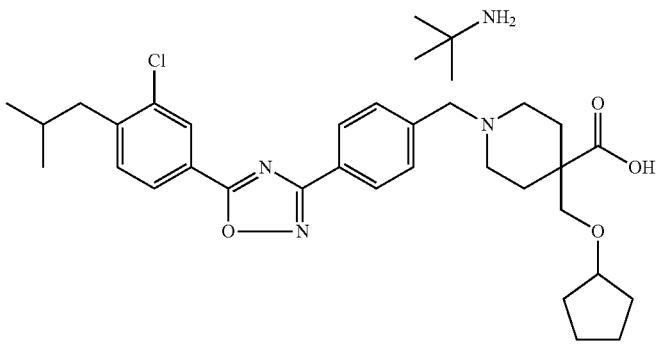 | 552.17 | as t-butyl amine salt<br>PMR: (CDCl₃ + CD₃OD; 500.13 MHz; δ ppm)<br>0.97 (d, J = 6.60 Hz, 6H); 1.27 (s, 9H); 1.44-1.50 (br m, 2H); 1.57-1.69 (br m, 8H); 1.99-2.07 (m, 1H); 2.07-2.13 (br d, 2H); 2.32-2.39 (br t, 2H); 2.70 (d, J = 7.20 Hz, 2H); 2.72-2.79 (br m, 2H); 3.40 (s, 2H); 3.62 (s, 2H); 3.81-3.86 (br m, 1H); 7.37 (d, J = 8.00 Hz, 1H); 7.48 (d, J = 8.20 Hz, 2H); 8.01 (dd, J₁ = 7.95 Hz, J2 = 1.65 Hz, 1H); 8.10 (d, J = 8.15 Hz, 2H); 8.21 (d, J = 1.55 Hz, 1H)<br>Three exchangeable protons |
| 62 | 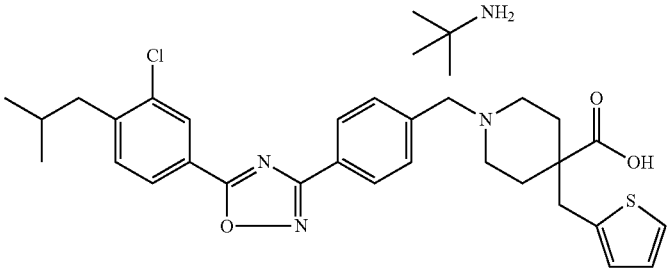 | 550.11 | as t-butyl amine salt<br>PMR: (CDCl₃ + CD₃OD; 500.13 MHz; δ ppm)<br>0.97 (d, J = 6.60 Hz, 6H); 1.28 (s, 9H); 1.56-1.64 (br m, 2H); 2.05 (septate, J = 6.75 Hz, 1H); 2.09-2.16 (br d, 2H); 2.33-2.42 (br t, 2H); 2.71 (d, J = 7.25 Hz, 2H); 2.75-2.82 (br d, 2H); 3.14 (s, 2H); 3.62 (s, 2H); 6.81 (d, J = 3.35 Hz, 1H); 6.89 (t, J = 3.65 Hz, 1H); 7.10 (d, J = 5.25 Hz, 1H); 7.39 (d, J = 8.00 Hz, 1H); 7.48 (d, J = 8.10 Hz, 2H); 8.02 (dd, J₁ = 7.95 Hz, J₂ = 1.45 Hz, 1H); 8.10 (d, J = 8.05 Hz, 2H); 8.20 (d, J = 1.30 Hz, 1H)<br>Three exchangeable protons |

| Ex. No. | Structure | (MS) (ES+) | NMR data |
|---|---|---|---|
| 63 | 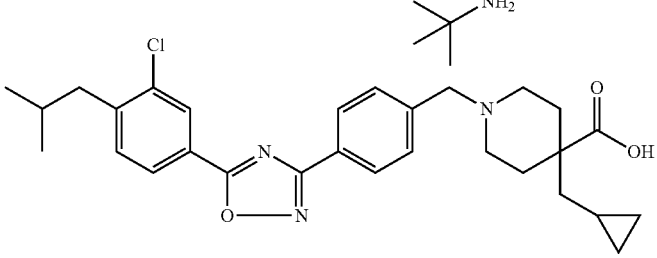 | 508.18 | as t-butyl amine salt<br>PMR: (CDCl$_3$ + CD$_3$OD; 500.13 MHz; δ ppm)<br>0.01-0.06 (br m, 2H); 0.38-0.44 (br m, 2H); 0.64-0.73 (br m, 1H); 0.97 (d, J = 6.65 Hz, 6H); 1.28 (s, 9H); 1.44 (d, J = 6.70 Hz, 2H); 1.53-1.62 (br t, 2H); 2.05 (septate, J = 6.85 Hz, 1H); 2.17-2.24 (br d, 2H); 2.27-2.37 (br t, 2H); 2.71 (d, J = 7.20 Hz, 2H); 2.78-2.85 (br d, 2H); 3.63 (s, 2H); 7.40 (d, J = 6.50 Hz, 1H); 7.49 (d, J = 8.15 Hz, 2H); 8.02 (dd, J$_1$ = 7.90 Hz, J$_2$ = 1.65 Hz, 1H); 8.10 (d, J = 8.10 Hz, 2H); 8.20 (d, J = 1.60 Hz, 1H)<br>Three exchangeable protons |
| 64 | 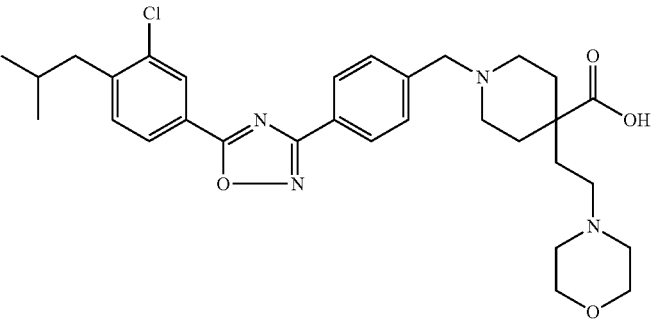 [SMILES: CC(C)Cc1ccc(-c2nc(-c3ccc(CN4CCC(CCN5CCOCC5)(C(=O)O)CC4)cc3)no2)cc1Cl] | 567.16 | as free form<br>PMR: (CDCl$_3$ + CD$_3$OD + D$_2$O; 500.13 MHz; δ ppm)<br>0.97 (d, J = 6.65 Hz, 6H); 1.45-1.53 (br dt, 2H); 1.77 (t, J = 7.35 Hz, 2H); 2.04 (septate, J = 6.75 Hz, 1H); 2.10-2.16 (br d, 2H): 2.27 (t, J = 10.70 Hz, 2H); 2.61 (t, J = 7.30 Hz, 2H); 2.66-2.75 (br d merged with m, 8H); 3.57 (s, 2H); 3.74-3.80 (br t, 4H); 7.36 (d, J = 8.00 Hz, 1H); 7.46 (d, J = 8.05 Hz, 2H); 8.01 (dd, J$_1$ = 7.94 Hz, J$_2$ = 1.55 Hz, 1H); 8.10 (d, J = 8.15Hz, 2H); 8.21 (d, J = 1.55 Hz, 1H)<br>One exchangeable protons |
| 65 | 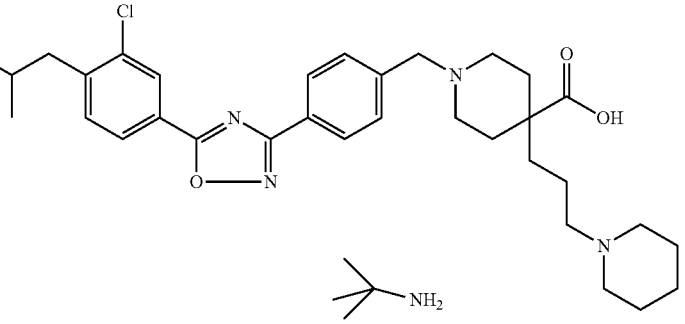 | 579.18 | as t-butyl amine salt<br>PMR: (CDCl$_3$; 400.13 MHz; δ ppm)<br>0.96 (d, J = 6.64 Hz, 6H); 1.21 (s, 9H); 1.32-1.43 (br m, 4H); 1.60-1.76 (br m, 8H); 2.04 (septate, J = 6.84 Hz, 1H); 2.14-2.24 (br m, 8H); 2.61-2.68 (br m, 2H); 2.70 (d, J = 7.20 Hz, 2H); 2.72-2.79 (br m, 2H); 3.58 (s, 2H); 7.36 (d, J = 8.00 Hz, 1H); 7.44 (d, J = 8.24 Hz, 2H); 8.01 (dd, J$_1$ = 7.96 Hz, J$_2$ = 1.76 Hz, 1H); 8.08 (d, J = 8.28 Hz, 2H); 8.20 (d, J = 1.72 Hz, 1H)<br>Three exchangeable protons |
| 66 | 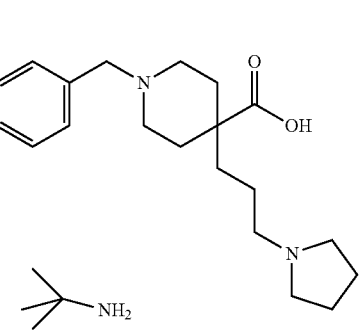 | 565.23 | as t-butyl amine salt<br>PMR: (CDCl$_3$; 400.13 MHz; δ ppm)<br>0.96 (d, J = 6.64 Hz, 6H); 1.20 (s, 9H); 1.30-1.41 (br m, 4H); 1.59-1.70 (br m, 2H); 1.83-1.91 (br s, 6H); 1.98-2.09 (m, 1H); 2.09-2.20 (br m, 6H); 2.70 (d, J = 7.20 Hz, 2H); 2.71-2.83 (m, 4H); 3.57 (s, 2H); 7.36 (d, J = 8.00 Hz, 1H); 7.43 (d, J = 8.20 Hz, 2H); 8.01 (dd, J$_1$ = 7.92 Hz, J$_2$ = 1.68 Hz, 1H); 8.07 (d, J = 8.20 Hz, 2H); 8.21 (d, J = 1.64 Hz, 1H)<br>Three exchangeable protons |

Biological Activity

Some of the representative compounds of the present invention were tested for in-vitro and in-vivo efficacy as mentioned below.

a) 35S-GTPγS Binding Assay

GTP-γ-$^{35}$S binding was performed using □15 μg protein of cell membranes suspended in 50 mM tris-HCl pH 7.5 containing 10 mM MgCl$_2$, 100 mM NaCl and 10 μM GDP. The radioligand was 0.025 nM [$^{35}$S] GTP-γ-S and non specific binding determined in the presence of 10 μM non-radioactive GTP-γ-S. Agonists of S1P receptors can be discriminated in the [$^{35}$S] GTP-γ-S binding assay. S1P and receptor agonists enhance the specific binding whereas inverse agonists reduce it. The maximal stimulation elicited by S1P was taken as a reference to define full or partial agonism and calculate the intrinsic activity (i.a.) of compounds.

Typical results shown in Table 1a indicate that compounds of the invention are able to activate S1P1 receptors with a potency similar to that of S1P itself (i.e. with full intrinsic activity and at nanomolar concentrations) without affecting significantly S1P2 and S1P3 receptors.

Table 1 b summarizes the half maximal effective concentration (EC50) for the examples of the present application.

Furthermore, we settled a binding assay on HEK293-EDG-1 cells on these membranes using [3H]dihydroS1P. By Scatchard analysis we identified one binding site for [3H]dihydroS1P. Both S1P and dihydroS1P (an S1P biometabolite) compete with [3H]dihydroS1P on transfected HEK293 cells with an 1050 closed to 5± nM and a maximum binding capacity Bmax of 13 μmol/mg of protein.

b) Assessment of Lymphopenia

Lymphopenia was assessed in vivo. Experiments were done in non-fasted/fasted Swiss mice and/or: Sprague Dawley rats, Wistar rats, Beagle dogs, Cynomolgus monkeys. Compounds were administered orally in suspension in carboxymethyl-cellulose 0.5-1% in water (W/V). Blood was taken on anesthetized/non anaesthetized animal (4% isoflurane) and samples collected in EDTA-containing vacuum tubes from 1 h 30 to 72 hours post administration for lymphopenia measurement.

After 10 minutes stirring, cells were counted using ABC Vet haemocytometer (Scil vet animal Care) for rodent and dog or ADVIA 120 hematology analyzer for monkeys. Pharmacodynamic effect was measured by the decrease in circulating lymphocytes by test item treatment in comparison with haematological parameters of control animals or versus pre-dosing in the same animals.

c) Evaluation of Activity for hERG Blockade Liability

HEK293 cells were stably transfected with the human hERG receptor gene. Binding assays were performed using 5 μg of cell membranes expressing hERG channel resuspended in 10 mM Hepes pH 7.4, 135 mM NaCl, 60 mM DL-Aspartic Acid Potassium, 1 mM EGTA, 0.8 mM MgCl$_2$, 10 mM (D+) Glucose, 0.01% BSA, in a final volume of 200 μL. For [$^3$H] Dofetilide binding, the incubation volume was 200 μL and incubation was performed 60 minutes at room temperature under continuous stirring. Non specific binding was estimated in the presence of 1 μM Astemizole. The reaction was terminated by filtration through Durapore BV 1.2 μm filters pre-soaked in 3% polyethyleneimine 10 minutes at room temperature. Filters were rinsed 2 times with 250 μL of ice cold 25 mM Tris-HCl pH 7.4 buffer. The filter-bound radioactivity was measured in a liquid scintillation counter with 50 μL of scintillation fluid. [$^3$H] Dofetilide was used at concentrations in the range of 5 nM.

The hERG binding investigated by use of [$^3$H] Dofetilide gives a Bmax=3.09 pmoles/mg protein and a Kd=4.24 nM.

No binding was detectable in wild type HEK293 cell membranes.

Tables 1 (Table 1a and 1b) and 2 show the results of the in vitro and the in vivo tests on some of the representative compounds of the present invention.

Table 1: In Vitro Evaluation

TABLE 1a

| Ex. No. | Structure | EC50 (nM) EDG1 | EDG3 | EDG5 | hERG (dofetilide) Ki (μM) |
|---|---|---|---|---|---|
| 1 | 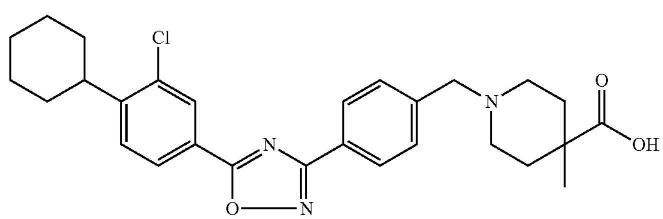 [SMILES: CC1(C(=O)O)CCN(Cc2ccc(-c3noc(-c4ccc(C5CCCCC5)c(Cl)c4)n3)cc2)CC1] | <1 | >1000 | >1000 | >10 |
| 2 | 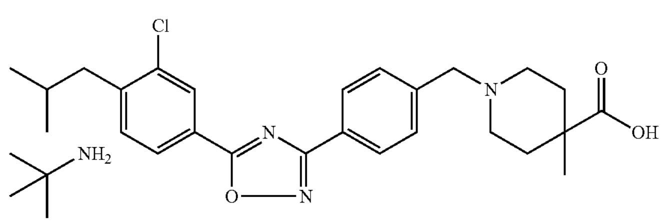 | <1 | — | — | >10 |
| 7 | 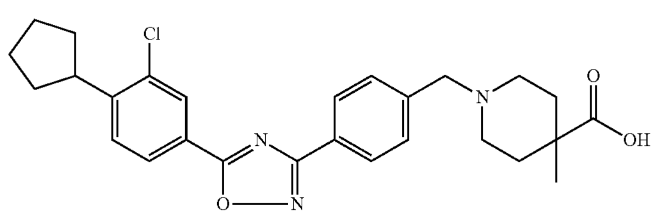 [SMILES: CC1(C(=O)O)CCN(Cc2ccc(-c3noc(-c4ccc(C5CCCC5)c(Cl)c4)n3)cc2)CC1] | <1 | 581 | >1000 | >10 |

TABLE 1a-continued

| Ex. No. | Structure | EC50 (nM) EDG1 | EC50 (nM) EDG3 | EC50 (nM) EDG5 | hERG (dofetilide) Ki (μM) |
|---|---|---|---|---|---|
| 9 | 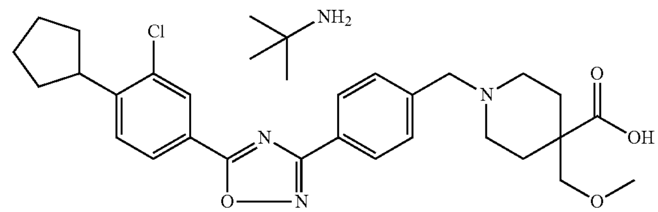 | <1 | >1000 | >1000 | >10 |
| 10 | 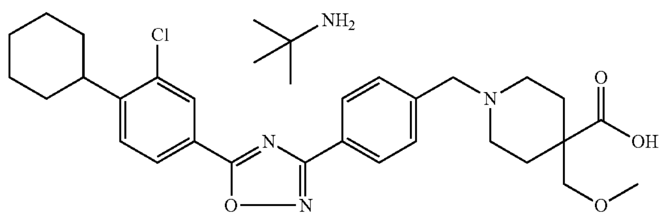 | <1 | 610 | — | >10 |
| 11 | 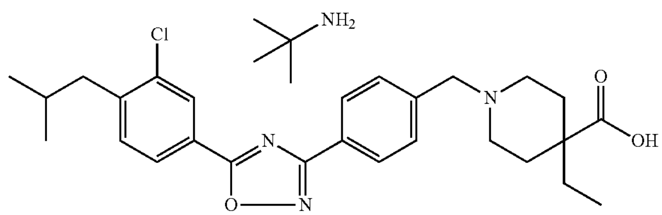 | <1 | 198 | >1000 | >10 |
| 12 | 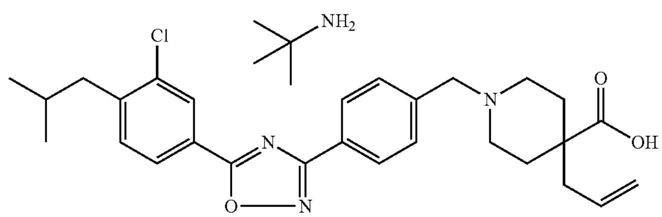 | <1 | >1000 | >1000 | >10 |
| 13 | 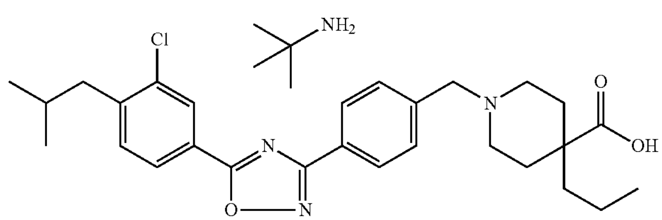 | <1 | >1000 | >1000 | >10 |
| 14 | 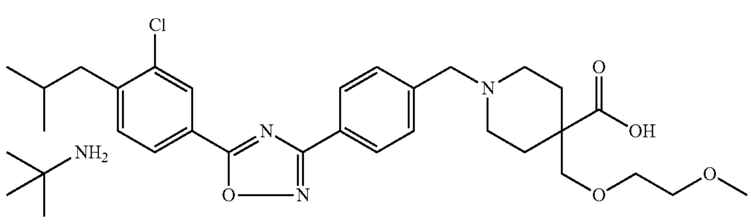 | <1 | >1000 | >1000 | >10 |
| 15 | 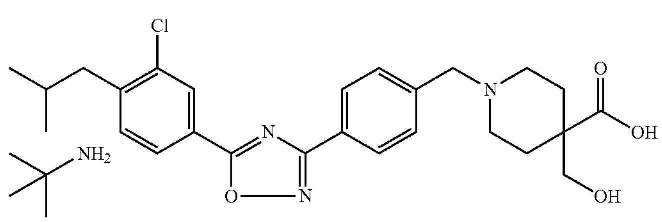 | <1 | >1000 | >1000 | >10 |

TABLE 1b

| Ex | EDG1 EC50 | Ex | EDG1 EC50 | Ex | EDG1 EC50 | Ex | EDG1 EC50 | Ex | EDG1 EC50 |
|---|---|---|---|---|---|---|---|---|---|
| 1 | <1 | 2 | <1 | 4 | <1 | 5 | <1 | 6 | <1 |
| 7 | <1 | 8 | <1 | 9 | <1 | 10 | <1 | 11 | <1 |
| 12 | <1 | 13 | <1 | 14 | <1 | 15 | <1 | 16 | <1 |
| 17 | <1 | 18 | <1 | 19 | <1 | 20 | <1 | 21 | <1 |
| 22 | <1 | 23 | <10 | 24 | <10 | 25 | <1 | 26 | <1 |
| 27 | <1 | 28 | <1 | 29 | <1 | 30 | <1 | 31 | <10 |
| 32 | <1 | 33 | <1 | 34 | <1 | 35 | <1 | 36 | <10 |
| 37 | <1 | 38 | <10 | 39 | <10 | 40 | <1 | 41 | <1 |
| 42 | <1 | 43 | <1 | 44 | <10 | 45 | <10 | 46 | <1 |
| 47 | <1 | 48 | <10 | 49 | <1 | 50 | <1 | 51 | <1 |
| 52 | <1 | 53 | <1 | 54 | <1 | 55 | <1 | 56 | <1 |
| 57 | <10 | 58 | <1 | 59 | <1 | 60 | <1 | 61 | <1 |
| 62 | <1 | 63 | <1 | 64 | <10 | 65 | <10 | 66 | <10 |

TABLE 2 in vivo evaluation

| Ex. No. | Structure | Lymphopenia in rats % lymphopenia at given dose at 24 hrs | Species |
|---|---|---|---|
| 2 | [structure] | 76% (0.3 mpk) | SD F |
| 11 | [structure] | 75% (0.3 mpk) | W F |
| 12 | [structure] | 66% (0.3 mpk) | W F |
| 14 | [structure] | 72% (0.3 mpk) | W M |
| 15 | [structure] | 69% (0.3 mpk) | SD F |

W: Wistar
SD: Sprague-Dawley
M: male
F: female

The results above show that the compounds of the present invention are S1P agonists and have high affinity for human EDG1 receptors (EC50 about 2 nM). More preferred compounds of the invention have EC50 less than 1 nM. The compounds of the present invention possess about 500 fold selectivity for EDG1 receptors over EDG3 receptor. Furthermore, the compounds of present invention have about 400 fold selectivity for EDG1 receptor over hERG channel and hence are expected to demonstrate a better side effect profile.

The preferred compounds of the present invention were found to exhibit lymphopenic activity in-vivo when administered orally to animal models. More preferably, the compounds of the invention exhibited lymphopenic activity of more than 50% at 8 hours and did not bind to hERG channel, even at a concentration as high as 5 μM.

Most preferably, the compounds of the invention which possessed EC50 of less than 1 nM, have >1000 fold selectivity for EDG1 receptor over EDG3, exhibited in-vivo lymphopenic activity of more than 50% at 24 hours and did not bind to hERG even at a concentration as high as 10 μM.

Comparative Examples

The table below shows that the WO2008/152149 monosubstituted carboxylate derivatives are poorly active in vitro as agonist on the human EDG1 receptor and ineffective in producing lymphopenia in rat model.

| | Comparative compounds | EDG1 EC50 (nM) | Lymphopenia in rats % lymphopenia at 1 mpk/p.o dose | |
|---|---|---|---|---|
| | | | 8 Hrs | 24 Hrs |
| 1 | Example XXVIII of WO2008/152149 | 11.7-19.8 | 18% | −54% |
| 2 | Example XXXI of WO2008/152149 | 57.2 | −25% | −101% |
| 3 | Example XIL of WO2008/152149 | 56.6 | −24% | −58% |
| 4 | Example XXXVI of WO2008/152149 | 13.9 | 2% | −57% |

Moreover, preferred compounds of the present invention also display an outstanding bioavailability. Comparison with a compound of WO2003105771 is shown in the following table:

| | Structure | Pharmacokinetic parameters in Swiss mice after oral administration (1 mg/kg p.o.) (n = 4) | |
|---|---|---|---|
| | | $C_{max}$ (ng/mL) | $AUC_{(0-48\ h)}$ (ng/mL*h) |
| Comparative compound 5 | Example 1 of WO2003105771 | 495 | 4530 |
| Example 3 | 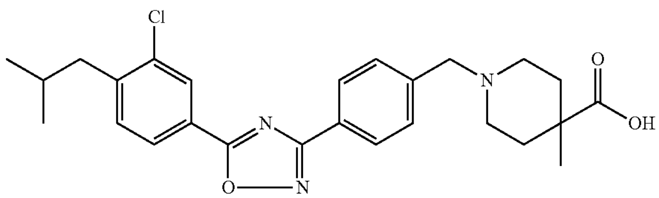 [SMILES: CC(C)Cc1ccc(-c2nc(-c3ccc(CN4CCC(C)(C(=O)O)CC4)cc3)no2)cc1Cl] | 798 | 13111 |
| Example 14 | 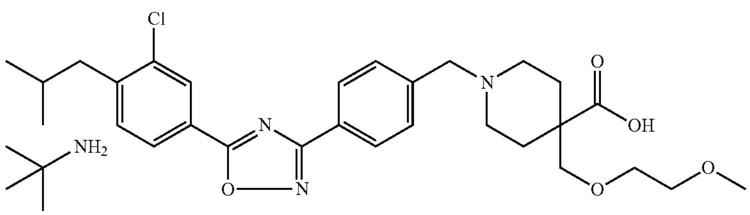 | 843 | 9241 |

It appears from the in vivo ED50 values below that the representative disubstituted monocarboxylate derivatives of the present invention exhibit improved in vivo lymphopenia activity over their corresponding dicarboxylate counterparts disclosed in WO 2008/152149:

| | | ED50 (EDG1) (In mice) |
|---|---|---|
| Example 8 | | 0.1 mg/kg |
| Comparative example 6 | Example 3 of WO 2008/152149 | 0.4 mg/kg |

-continued

| | | ED50 (EDG1) (In mice) |
|---|---|---|
| Example 3 | [structure: 3-methyl-4-isobutyl-chlorophenyl oxadiazole phenyl methylpiperidine 4-methyl-4-carboxylic acid] | 0.2 mg/kg |
| Example 14 | [structure: chloro-isobutyl-phenyl oxadiazole phenyl methylpiperidine carboxylic acid with methoxyethoxymethyl substituent, with tert-butylamine] | 0.2 mg/kg |
| Comparative example 7 | [structure: isobutylphenyl oxadiazole phenyl methylpiperidine dicarboxylic acid] Example 1 of WO 2008/152149 | 1.8 mg/kg |
| Example 10 | [structure: cyclohexyl-chloro-phenyl oxadiazole phenyl methylpiperidine carboxylic acid with methoxymethyl substituent, with tert-butylamine] | 0.2 mg/kg |
| Comparative example 8 | [structure: cyclohexylphenyl oxadiazole phenyl methylpiperidine dicarboxylic acid, HCl] Example 37 of WO 2008/152149 | 10 mg/kg |

The compounds of the invention show a better in vivo activity profile over their corresponding counterparts of WO 2007/132307, as evidenced below:

| | | ED50 (EDG1) |
|---|---|---|
| Compound of the invention | [structure: isobutylphenyl oxadiazole phenyl methylpiperidine 4-methyl-4-carboxylic acid] | 40% at 1 mg/kg |

| | | |
|---|---|---|
| | | ED50 (EDG1) |
| Comparative example 9 | 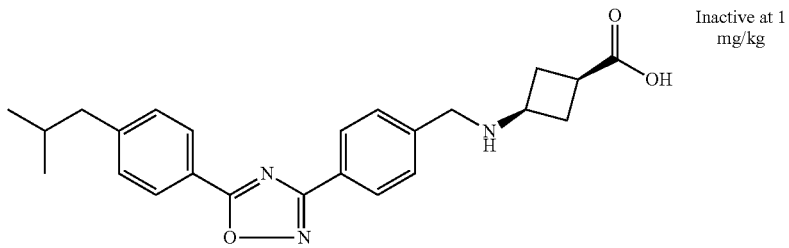 Example 7 of WO 2007/132307 | Inactive at 1 mg/kg |

The invention claimed is:

1. A compound of formula (I):

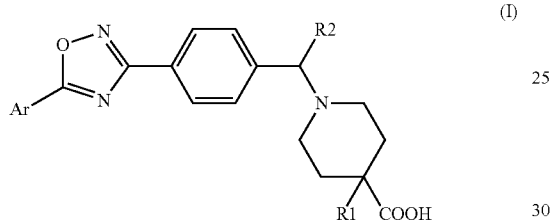

wherein:

Ar is a phenyl group optionally substituted by one or more identical or different group(s) selected from the group consisting of halogen, alkyl, cycloalkyl, —Oalkyl, and phenyl;

R1 represents —X—(Y)$_n$— where

—X— is selected from the group consisting of -alkyl-, -alkenyl-, -alkynyl-, -aryl-, and -alkylaryl-, each Y, identical or different is selected from the group consisting of H, OH, halogen, —Oalkyl, —Oalkylaryl, —OalkylOalkyl, —Oaryl, heteroaryl, —Oaryl (Oalkyl), —Ocycloalkyl, -cycloalkyl, and heterocyclyl;

n is 1 to 3; and where R1 is not —C(=O)OH; and

R2 is H or alkyl;

or one of its stereoisomers or salts thereof.

2. The compound according to claim 1, wherein Ar is a phenyl group substituted with two identical or different groups in addition to the oxadiazole group.

3. The compound according to claim 1 of formula (II):

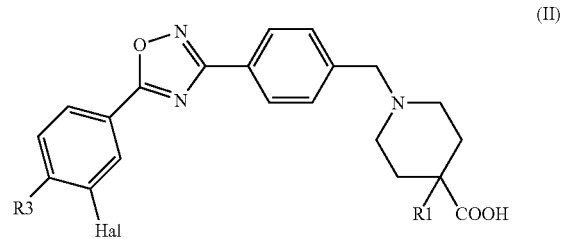

wherein:

R3 is selected from halogen, phenyl, cycloalkyl, alkyl, and —Oalkyl;

Hal represents a halogen atom.

4. The compound according to claim 1, wherein R1 is selected from:

methyl, ethyl, n-propyl, isopropyl, n-butyl, isobutyl, secondary butyl, tertiary butyl, n-pentyl, isopentyl, n-hexyl, isohexyl, hydroxymethyl, hydroxyethyl, hydroxypropyl, methoxymethyl, ethoxymethyl, methoxyethyl, vinyl, allyl, methoxyethoxymethyl, ethoxyethoxymethyl, ethoxyethoxyethyl, Phenyl, benzyl, benzyloxymethyl, benzyloxyethyl, —CH$_2$-[Ph(o-F)], —CH$_2$-[Ph(m-F)], —CH$_2$-[Ph(p-F)], —CH$_2$-[Ph(o-OMe)], —CH$_2$-[Ph(m-OMe)], or —CH$_2$-[Ph(p-OMe)], methoxybutyl, methoxyethoxymethyl, methoxyethoxyethyl, —CH$_2$-[Ph(o,o-F$_2$)], —CH$_2$-[Ph(m-CF$_3$)], —CH$_2$-furyl, —CH$_2$-pyridyl, (2-methoxy-phenoxy)-ethyl, 4-methoxy-benzyl, isopropoxy methyl, cyclopentyloxymethyl, thiophen-2-ylmethyl, cyclopropylmethyl, 2-morpholin-4-yl-ethyl, 3-piperidin-1-yl-propyl, 3-pyrrolidin-1-yl-propyl.

5. The compound according to claim 1, wherein R2 is H.

6. The compound according to claim 3, wherein R3 is selected from the group consisting of phenyl, cyclohexyl, cyclopentyl, isobutyl, and isopropoxy.

7. The compound according to claim 1 which is selected from the group consisting of:

1-{4-[5-(3-chloro-4-cyclohexylphenyl)-[1,2,4]-oxadiazol-3-yl]benzyl}-4-methylpiperidine-4-carboxylic acid 1-{4-[5-(3-chloro-4-isobutylphenyl)-[1,2,4]-oxadiazol-3-yl]benzyl}-4-methylpiperidine-4-carboxylic acid 1-{4-[5-(3-chloro-4-cyclopentylphenyl)-[1,2,4]-oxadiazol-3-yl]benzyl}-4-methylpiperidine-4-carboxylic acid 1-{4-[5-(2-Chlorobiphenyl-4-yl)-[1,2,4]-oxadiazol-3-yl]benzyl}-4-methylpiperidine-4-carboxylic acid 1-{4-[5-(3-chloro-4-cyclopentylphenyl)-[1,2,4]-oxadiazol-3-yl]benzyl}-4-methoxymethylpiperidine-4-carboxylic acid 1-{4-[5-(3-chloro-4-cyclohexylphenyl)-[1,2,4]-oxadiazol-3-yl]benzyl}-4-methoxymethylpiperidine-4-carboxylic acid 1-{4-[5-(3-chloro-4-isobutylphenyl)-[1,2,4]-oxadiazol-3-yl]benzyl}-4-ethylpiperidine-4-carboxylic acid 4-allyl-1-{4-[5-(3-chloro-4-isobutylphenyl)-[1,2,4]-oxadiazol-3-yl]benzyl}piperidine-4-carboxylic acid 1-{4-[5-(3-chloro-4-isobutylphenyl)-[1,2,4]-oxadiazol-3-yl]benzyl}-4-propylpiperidine-4-carboxylic acid
1-{4-[5-(3-chloro-4-isobutylphenyl)-[1,2,4]-oxadiazol-3-yl]benzyl}-4-(2-methoxyethoxymethyl)piperidine-4-carboxylic acid
1-{4-[5-(3-chloro-4-isobutylphenyl)-[1,2,4]-oxadiazol-3-yl]benzyl}-4-hydroxymethylpiperidine-4-carboxylic acid
1-{4-[5-(3-Chloro-4-isobutylphenyl)-[1,2,4]oxadiazol-3-yl]-benzyl}-4-methoxymethylpiperidine-4-carboxylic acid
4-Allyl-1-{4-[5-(2-chlorobiphenyl-4-yl)-[1,2,4]-oxadiazol-3-yl]-benzyl}piperidine-4-carboxylic acid
1-{4-[5-(2-Chlorobiphenyl-4-yl)-[1,2,4]-oxadiazol-3-yl]-benzyl}-4-propylpiperidine-4-carboxylic acid
1-{4-[5-(2-Chlorobiphenyl-4-yl)-[1,2,4]-oxadiazol-3-yl]-benzyl}-4-(2-methoxyethoxymethyl)piperidine-4-carboxylic acid
4-Benzyloxymethyl-1-{4-[5-(2-chlorobiphenyl-4-yl)-[1,2,4]-oxadiazol-3-yl]-benzyl}piperidine-4-carboxylic acid
4-Benzyloxymethyl-1-{4-[5-(3-chloro-4-isobutylphenyl)-[1,2,4]-oxadiazol-3-yl]-benzyl}piperidine-4-carboxylic acid
1-{4-[5-(2-Chlorobiphenyl-4-yl)-[1,2,4]-oxadiazol-3-yl]-benzyl}-4-hydroxymethylpiperidine-4-carboxylic acid
1-{4-[5-(3-Chloro-4-isobutylphenyl)-[1,2,4]-oxadiazol-3-yl]-benzyl}-4-phenylpiperidine-4-carboxylic acid
4-Benzyl-1-{4-[5-(3-chloro-4-isobutylphenyl)-[1,2,4]-oxadiazol-3-yl]benzyl}-piperidine-4-carboxylic acid
1-{4-[5-(3-Chloro-4-isobutyl-phenyl)-[1,2,4]oxadiazol-3-yl]-benzyl}-4-(4-fluoro-benzyl)-piperidine-4-carboxylic acid
1-{4-[5-(3-Chloro-4-isobutyl-phenyl)-[1,2,4]oxadiazol-3-yl]-benzyl}-4-(2-fluoro-benzyl)-piperidine-4-carboxylic acid
1-{4-[5-(3-Chloro-4-isobutyl-phenyl)-[1,2,4]oxadiazol-3-yl]-benzyl}-4-(4-methoxy-benzyl)-piperidine-4-carboxylic acid
1-{4-[5-(3-Chloro-4-isobutyl-phenyl)-[1,2,4]oxadiazol-3-yl]-benzyl}-4-(2-methoxy-benzyl)-piperidine-4-carboxylic acid
1-{4-[5-(2-chlorobiphenyl-4-yl)-[1,2,4]-oxadiazol-3-yl]benzyl}-4-methoxymethylpiperidine-4-carboxylic acid
1-{4-[5-(2-Chlorobiphenyl-4-yl)-[1,2,4]-oxadiazol-3-yl]-benzyl}-4-ethylpiperidine-4-carboxylic acid
1-{4-[5-(4-Isobutyl-phenyl)-[1,2,4]-oxadiazol-3-yl]-benzyl}-4-methyl-piperidine-4-carboxylic acid
1-{4-[5-(3-Chloro-4-isobutyl-phenyl)-[1,2,4]-oxadiazol-3-yl]-benzyl}-4-(4-methoxy-butyl)-piperidine-4-carboxylic acid
1-{4-[5-(3-chloro-4-isobutylphenyl)-[1,2,4]-oxadiazol-3-yl]benzyl}-4-(2-methoxyethoxymethyl)piperidine-4-carboxylic acid
1-{4-[5-(3-Chloro-4-isobutyl-phenyl)-[1,2,4]-oxadiazol-3-yl]-benzyl}-4-(2-phenoxy-ethyl)-piperidine-4-carboxylic acid
1-{4-[5-(3-Chloro-4-isobutyl-phenyl)-[1,2,4]-oxadiazol-3-yl]-benzyl}-4-(2,6-difluoro-benzyl)-piperidine-4-carboxylic acid
1-{4-[5-(3-Chloro-4-isobutyl-phenyl)-[1,2,4]-oxadiazol-3-yl]-benzyl}-4-isobutyl-piperidine-4-carboxylic acid
1-{4-[5-(3-Chloro-4-isobutyl-phenyl)-[1,2,4]-oxadiazol-3-yl]-benzyl}-4-isopropyl-piperidine-4-carboxylic acid
1-{4-[5-(3-Chloro-4-isobutyl-phenyl)-[1,2,4]-oxadiazol-3-yl]-benzyl}-4-(3-trifluoro methyl-benzyl)-piperidine-4-carboxylic acid
1-{4-[5-(3-Chloro-4-isobutyl-phenyl)-[1,2,4]oxadiazol-3-yl]-benzyl}-4-furan-2-ylmethyl-piperidine-4-carboxylic acid
1-{4-[5-(3-Chloro-4-isobutyl-phenyl)-[1,2,4]-oxadiazol-3-yl]-benzyl}-4-pyridin-2-ylmethyl-piperidine-4-carboxylic acid
1-{4-[5-(3-Chloro-4-isobutyl-phenyl)-[1,2,4]-oxadiazol-3-yl]-benzyl}-4-[2-(2-methoxy-phenoxy)-ethyl]-piperidine-4-carboxylic acid
1-{4-[5-(3-Chloro-4-isobutyl-phenyl)-[1,2,4]-oxadiazol-3-yl]-benzyl}-4-pyridin-3-ylmethyl-piperidine-4-carboxylic acid
1-{4-[5-(3-Chloro-4-isobutyl-phenyl)-[1,2,4]-oxadiazol-3-yl]-benzyl}-4-pyridin-4-ylmethyl-piperidine-4-carboxylic acid
1-{4-[5-(3-Chloro-4-isopropoxy-phenyl)-[1,2,4]-oxadiazol-3-yl]-benzyl}-4-methyl-piperidine-4-carboxylic acid
1-{4-[5-(4-tert-Butyl-3-chloro-phenyl)-[1,2,4]-oxadiazol-3-yl]-benzyl}-4-methyl-piperidine-4-carboxylic acid
1-{4-[5-(3-Chloro-4-propyl-phenyl)-[1,2,4]-oxadiazol-3-yl]-benzyl}-4-methyl-piperidine-4-carboxylic acid
1-{4-[5-(3-Chloro-4-isopropoxy-phenyl)-[1,2,4]-oxadiazol-3-yl]-benzyl}-4-(2-methoxy-ethoxymethyl)-piperidine-4-carboxylic acid
1-{4-[5-(3-Chloro-4-isopropoxy-phenyl)-[1,2,4]-oxadiazol-3-yl]-benzyl}-4-ethyl-piperidine-4-carboxylic acid
4-Allyl-1-{4-[5-(3-chloro-4-isopropoxy-phenyl)-[1,2,4]-oxadiazol-3-yl]-benzyl}-piperidine-4-carboxylic acid
1-{4-[5-(2-Chloro-biphenyl-4-yl)-[1,2,4]-oxadiazol-3-yl]-benzyl}-4-pyridin-2-ylmethyl-piperidine-4-carboxylic acid
1-{4-[5-(2-Chloro-biphenyl-4-yl)-[1,2,4]-oxadiazol-3-yl]-benzyl}-4-(4-methoxy-benzyl)-piperidine-4-carboxylic acid
1-{4-[5-(2-Chloro-biphenyl-4-yl)-[1,2,4]-oxadiazol-3-yl]-benzyl}-4-(4-fluoro-benzyl)-piperidine-4-carboxylic acid
1-{4-[5-(3-Chloro-4-cyclohexylphenyl)-[1,2,4]-oxadiazol-3-yl]-benzyl}-4-(4-methoxy-benzyl)-piperidine-4-carboxylic acid
1-{4-[5-(3-Chloro-4-cyclohexylphenyl)-[1,2,4]-oxadiazol-3-yl]-benzyl}-4-ethyl-piperidine-4-carboxylic acid
4-Benzyl-1-{4-[5-(2-chloro-biphenyl-4-yl)-[1,2,4]-oxadiazol-3-yl]-benzyl}-piperidine-4-carboxylic acid
1-{4-[5-(3-Chloro-4-cyclohexyl-phenyl)-[1,2,4]-oxadiazol-3-yl]-benzyl}-4-pyridin-2-ylmethyl-piperidine-4-carboxylic acid
1-{4-[5-(3-Chloro-4-isopropoxy-phenyl)-[1,2,4]-oxadiazol-3-yl]-benzyl}-4-methoxymethyl-piperidine-4-carboxylic acid
1-{4-[5-(2-Chloro-biphenyl-4-yl)-[1,2,4]-oxadiazol-3-yl]-benzyl}-4-pyridin-3-ylmethyl-piperidine-4-carboxylic acid
1-{4-[5-(3-Chloro-4-isobutyl-phenyl)-[1,2,4]-oxadiazol-3-yl]-benzyl}-4-(2-ethoxy-ethoxymethyl)-piperidine-4-carboxylic acid
1-{4-[5-(3-Chloro-4-isobutyl-phenyl)-[1,2,4]-oxadiazol-3-yl]-benzyl}-4-isopropoxy methyl-piperidine-4-carboxylic acid 1-{4-[5-(3-Chloro-4-isobutyl-phenyl)-[1,2,4]-oxadiazol-3-yl]-benzyl}-4-cyclopentyloxymethyl-piperidine-4-carboxylic acid 1-{4-[5-(3-Chloro-4-isobutyl-phenyl)-[1,2,4]-oxadiazol-3-yl]-benzyl}-4-thiophen-2-ylmethyl-piperidine-4-carboxylic acid 1-{4-[5-(3-Chloro-4-isobutyl-phenyl)-[1,2,4]-oxadiazol-3-yl]-benzyl}-4-cyclopropylmethyl-piperidine-4-carboxylic acid 1-{4-[5-(3-Chloro-4-isobutyl-phenyl)-[1,2,4]-oxadiazol-3-yl]-benzyl}-4-(2-morpholin-4-yl-ethyl)-piperidine-4-carboxylic acid 1-{4-[5-(3-Chloro-4-isobutyl-phenyl)-[1,2,4]oxadiazol-3-yl]-benzyl}-4-(3-piperidin-1-yl-propyl)-piperidine-4-carboxylic acid 1-{4-[5-(3-Chloro-4-isobutyl-phenyl)-[1,2,4]oxadiazol-3-yl]-benzyl}-4-(3-pyrrolidin-1-yl-propyl)-piperidine-4-carboxylic acid and their pharmaceutically acceptable salts thereof.

8. The compound or salt thereof according to claim 1 which is selected from the group consisting of:

1-{4-[5-(3-chloro-4-cyclohexylphenyl)-[1,2,4]-oxadiazol-3-yl]benzyl}-4-methylpiperidine-4-carboxylic acid 1-{4-[5-(3-chloro-4-isobutylphenyl)-[1,2,4]-oxadiazol-3-yl]benzyl}-4-methylpiperidine-4-carboxylic acid, tert-butylamine salt 1-{4-[5-(3-chloro-4-isobutylphenyl)-[1,2,4]-oxadiazol-3-yl]benzyl}-4-methylpiperidine-4-carboxylic acid 1-{4-[5-(3-chloro-4-isobutylphenyl)-[1,2,4]-oxadiazol-3-yl]benzyl}-4-methylpiperidine-4-carboxylic acid, sodium salt 1-{4-[5-(3-chloro-4-isobutylphenyl)-[1,2,4]-oxadiazol-3-yl]benzyl}-4-methylpiperidine-4-carboxylic acid, arginine salt 1-{4-[5-(3-chloro-4-isobutylphenyl)-[1,2,4]-oxadiazol-3-yl]benzyl}-4-methylpiperidine-4-carboxylic acid, potassium salt 1-{4-[5-(3-chloro-4-cyclopentylphenyl)-[1,2,4]-oxadiazol-3-yl]benzyl}-4-methylpiperidine-4-carboxylic acid 1-{4-[5-(2-Chlorobiphenyl-4-yl)-[1,2,4]-oxadiazol-3-yl]benzyl}-4-methylpiperidine-4-carboxylic acid 1-{4-[5-(3-chloro-4-cyclopentylphenyl)-[1,2,4]-oxadiazol-3-yl]benzyl}-4-methoxymethylpiperidine-4-carboxylic acid, tert-butylamine salt 1-{4-[5-(3-chloro-4-cyclohexylphenyl)-[1,2,4]-oxadiazol-3-yl]benzyl}-4-methoxymethylpiperidine-4-carboxylic acid tert-butylamine salt 1-{4-[5-(3-chloro-4-isobutylphenyl)-[1,2,4]-oxadiazol-3-yl]benzyl}-4-ethylpiperidine-4-carboxylic acid tert-butylamine salt 4-allyl-1-{4-[5-(3-chloro-4-isobutylphenyl)-[1,2,4]-oxadiazol-3-yl]benzyl}piperidine-4-carboxylic acid tert-butylamine salt 1-{4-[5-(3-chloro-4-isobutylphenyl)-[1,2,4]-oxadiazol-3-yl]benzyl}-4-propylpiperidine-4-carboxylic acid tert-butylamine salt 1-{4-[5-(3-chloro-4-isobutylphenyl)-[1,2,4]-oxadiazol-3-yl]benzyl}-4-(2-methoxyethoxymethyl)piperidine-4-carboxylic acid tert-butylamine salt 1-{4-[5-(3-chloro-4-isobutylphenyl)-[1,2,4]-oxadiazol-3-yl]benzyl}-4-hydroxymethylpiperidine-4-carboxylic acid tert-butylamine salt 1-{4-[5-(3-Chloro-4-isobutylphenyl)-[1,2,4]oxadiazol-3-yl]-benzyl}-4-methoxymethylpiperidine-4-carboxylic acid tert-butylamine salt 4-Allyl-1-{4-[5-(2-chlorobiphenyl-4-yl)-[1,2,4]-oxadiazol-3-yl]-benzyl}piperidine-4-carboxylic acid tert-butylamine salt 1-{4-[5-(2-Chlorobiphenyl-4-yl)-[1,2,4]-oxadiazol-3-yl]-benzyl}-4-propylpiperidine-4-carboxylic acid tert-butylamine salt 1-{4-[5-(2-Chlorobiphenyl-4-yl)-[1,2,4]-oxadiazol-3-yl]-benzyl}-4-(2-methoxyethoxymethyl)piperidine-4-carboxylic acid tert-butylamine salt 4-Benzyloxymethyl-1-{4-[5-(2-chlorobiphenyl-4-yl)-[1,2,4]-oxadiazol-3-yl]-benzyl}piperidine-4-carboxylic acid tert-butylamine salt 4-Benzyloxymethyl-1-{4-[5-(3-chloro-4-isobutylphenyl)-[1,2,4]-oxadiazol-3-yl]-benzyl}piperidine-4-carboxylic acid tert-butylamine salt 1-{4-[5-(2-Chlorobiphenyl-4-yl)-[1,2,4]-oxadiazol-3-yl]-benzyl}-4-hydroxymethylpiperidine-4-carboxylic acid tert-butylamine salt 1-{4-[5-(3-Chloro-4-isobutylphenyl)-[1,2,4]-oxadiazol-3-yl]-benzyl}-4-phenylpiperidine-4-carboxylic acid tert-butylamine salt 4-Benzyl-1-{4-[5-(3-chloro-4-isobutylphenyl)-[1,2,4]-oxadiazol-3-yl]benzyl}-piperidine-4-carboxylic acid tert-butylamine salt 1-{4-[5-(3-Chloro-4-isobutyl-phenyl)-[1,2,4]oxadiazol-3-yl]-benzyl}-4-(4-fluoro-benzyl)-piperidine-4-carboxylic acid tert-butylamine salt 1-{4-[5-(3-Chloro-4-isobutyl-phenyl)-[1,2,4]oxadiazol-3-yl]-benzyl}-4-(2-fluoro-benzyl)-piperidine-4-carboxylic acid tert-butylamine salt 1-{4-[5-(3-Chloro-4-isobutyl-phenyl)-[1,2,4]oxadiazol-3-yl]-benzyl}-4-(4-methoxy-benzyl)-piperidine-4-carboxylic acid tert-butylamine salt 1-{4-[5-(3-Chloro-4-isobutyl-phenyl)-[1,2,4]oxadiazol-3-yl]-benzyl}-4-(2-methoxy-benzyl)-piperidine-4-carboxylic acid tert-butylamine salt 1-{4-[5-(2-chlorobiphenyl-4-yl)-[1,2,4]-oxadiazol-3-yl]benzyl}-4-ethoxymethylpiperidine-4-carboxylic acid tert-butylamine salt 1-{4-[5-(2-Chlorobiphenyl-4-yl)-[1,2,4]-oxadiazol-3-yl]-benzyl}-4-ethylpiperidine-4-carboxylic acid tert-butylamine salt, 1-{4-[5-(4-Isobutyl-phenyl)-[1,2,4]-oxadiazol-3-yl]-benzyl}-4-methyl-piperidine-4-carboxylic acid tert-butyl amine salt 1-{4-[5-(3-Chloro-4-isobutyl-phenyl)-[1,2,4]-oxadiazol-3-yl]-benzyl}-4-(4-methoxy-butyl)-piperidine-4-carboxylic acid tert-butyl amine salt 1-{4-[5-(3-chloro-4-isobutylphenyl)-[1,2,4]-oxadiazol-3-yl]benzyl}-4-(2-methoxyethoxymethyl)piperidine-4-carboxylic acid potassium salt 1-{4-[5-(3-Chloro-4-isobutyl-phenyl)-[1,2,4]-oxadiazol-3-yl]-benzyl}-4-(2-phenoxy-ethyl)-piperidine-4-carboxylic acid tert-butyl amine salt 1-{4-[5-(3-Chloro-4-isobutyl-phenyl)-[1,2,4]-oxadiazol-3-yl]-benzyl}-4-(2,6-difluoro-benzyl)-piperidine-4-carboxylic acid tert-butyl amine salt 1-{4-[5-(3-Chloro-4-isobutyl-phenyl)-[1,2,4]-oxadiazol-3-yl]-benzyl}-4-isobutyl-piperidine-4-carboxylic acid tert-butyl amine salt 1-{4-[5-(3-Chloro-4-isobutyl-phenyl)-[1,2,4]-oxadiazol-3-yl]-benzyl}-4-isopropyl-piperidine-4-carboxylic acid tert-butyl amine salt 1-{4-[5-(3-Chloro-4-isobutyl-phenyl)-[1,2,4]-oxadiazol-3-yl]-benzyl}-4-(3-trifluoro methyl-benzyl)-piperidine-4-carboxylic acid tert-butyl amine salt 1-{4-[5-(3-Chloro-4-isobutyl-phenyl)-[1,2,4]oxadiazol-3-yl]-benzyl}-4-furan-2-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-pyridin-2-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-[2-(2-methoxy-phenoxy)-ethyl]-piperidine-4-carboxylic acid tert-butyl amine salt
1-{4-[5-(3-Chloro-4-isobutyl-phenyl)-[1,2,4]-oxadiazol-3-yl]-benzyl}-4-pyridin-3-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-pyridin-4-ylmethyl-piperidine-4-carboxylic acid tert-butyl amine salt
1-{4-[5-(3-Chloro-4-isopropoxy-phenyl)-[1,2,4]-oxadiazol-3-yl]-benzyl}-4-methyl-piperidine-4-carboxylic acid tert-butyl amine salt
1-{4-[5-(4-tert-Butyl-3-chloro-phenyl)-[1,2,4]-oxadiazol-3-yl]-benzyl}-4-methyl-piperidine-4-carboxylic acid tert-butyl amine salt
1-{4-[5-(3-Chloro-4-propyl-phenyl)-[1,2,4]-oxadiazol-3-yl]-benzyl}-4-methyl-piperidine-4-carboxylic acid tert-butyl amine salt
1-{4-[5-(3-Chloro-4-isopropoxy-phenyl)-[1,2,4]-oxadiazol-3-yl]-benzyl}-4-(2-methoxy-ethoxymethyl)-piperidine-4-carboxylic acid tert-butyl amine salt
1-{4-[5-(3-Chloro-4-isopropoxy-phenyl)-[1,2,4]-oxadiazol-3-yl]-benzyl}-4-ethyl-piperidine-4-carboxylic acid tert-butyl amine salt
4-Allyl-1-{4-[5-(3-chloro-4-isopropoxy-phenyl)-[1,2,4]-oxadiazol-3-yl]-benzyl}-piperidine-4-carboxylic acid tert-butyl amine salt
1-{4-[5-(2-Chloro-biphenyl-4-yl)-[1,2,4]-oxadiazol-3-yl]-benzyl}-4-pyridin-2-ylmethyl-piperidine-4-carboxylic acid tert-butyl amine salt
1-{4-[5-(2-Chloro-biphenyl-4-yl)-[1,2,4]-oxadiazol-3-yl]-benzyl}-4-(4-methoxy-benzyl)-piperidine-4-carboxylic acid tert-butyl amine salt
1-{4-[5-(2-Chloro-biphenyl-4-yl)-[1,2,4]-oxadiazol-3-yl]-benzyl}-4-(4-fluoro-benzyl)-piperidine-4-carboxylic acid tert-butyl amine salt
1-{4-[5-(3-Chloro-4-cyclohexylphenyl)-[1,2,4]-oxadiazol-3-yl]-benzyl}-4-(4-methoxy-benzyl)-piperidine-4-carboxylic acid tert-butyl amine salt
1-{4-[5-(3-Chloro-4-cyclohexylphenyl)-[1,2,4]-oxadiazol-3-yl]-benzyl}-4-ethyl-piperidine-4-carboxylic acid tert-butyl amine salt
4-Benzyl-1-{4-[5-(2-chloro-biphenyl-4-yl)-[1,2,4]-oxadiazol-3-yl]-benzyl}-piperidine-4-carboxylic acid tert-butyl amine salt
1-{4-[5-(3-Chloro-4-cyclohexyl-phenyl)-[1,2,4]-oxadiazol-3-yl]-benzyl}-4-pyridin-2-ylmethyl-piperidine-4-carboxylic acid tert-butyl amine salt
1-{4-[5-(3-Chloro-4-isopropoxy-phenyl)-[1,2,4]-oxadiazol-3-yl]-benzyl}-4-methoxymethyl-piperidine-4-carboxylic acid tert-butyl amine salt
1-{4-[5-(2-Chloro-biphenyl-4-yl)-[1,2,4]-oxadiazol-3-yl]-benzyl}-4-pyridin-3-ylmethyl-piperidine-4-carboxylic acid tert-butyl amine salt
1-{4-[5-(3-Chloro-4-isobutyl-phenyl)-[1,2,4]-oxadiazol-3-yl]-benzyl}-4-(2-ethoxy-ethoxymethyl)-piperidine-4-carboxylic acid tert-butyl amine salt
1-{4-[5-(3-Chloro-4-isobutyl-phenyl)-[1,2,4]-oxadiazol-3-yl]-benzyl}-4-isopropoxy methyl-piperidine-4-carboxylic acid tert-butyl amine salt
1-{4-[5-(3-Chloro-4-isobutyl-phenyl)-[1,2,4]-oxadiazol-3-yl]-benzyl}-4-cyclopentyloxymethyl-piperidine-4-carboxylic acid tert-butyl amine salt
1-{4-[5-(3-Chloro-4-isobutyl-phenyl)-[1,2,4]-oxadiazol-3-yl]-benzyl}-4-thiophen-2-ylmethyl-piperidine-4-carboxylic acid tert-butyl amine salt and
1-{4-[5-(3-Chloro-4-isobutyl-phenyl)-[1,2,4]-oxadiazol-3-yl]-benzyl}-4-cyclopropylmethyl-piperidine-4-carboxylic acid tert-butyl amine salt, or one of their stereoisomers.

9. A process of preparation of a compound according to claim 1 comprising saponifying a compound of formula (III)

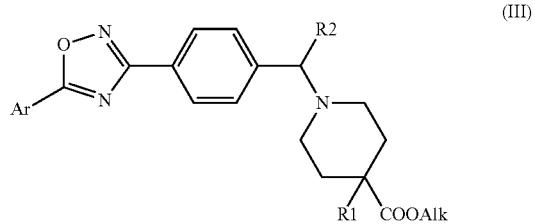

(III)

where Alk represents a C1-C6 alkyl group, optionally followed by forming the desired addition salt.

10. The process according to claim 9 which further comprises the step of preparing the compound of formula (III) by coupling a compound of formula (IV):

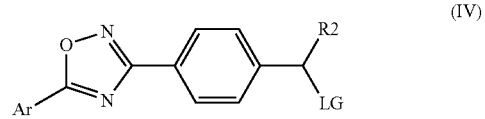

(IV)

with a corresponding compound of formula (V):

(V)

where LG is a leaving group.

11. The process according to claim 10 further comprising the step of preparing the compound of formula (IV) wherein LG is a halide or mesylate, by converting a compound of formula (VI):

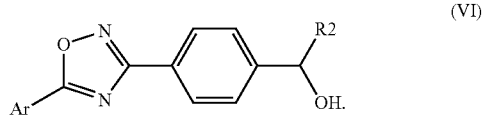

(VI)

12. A process of preparation of a compound according to claim 1 comprising reacting a compound of formula (VII):

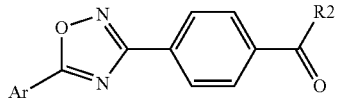
(VII)

with a compound of formula (VIII)

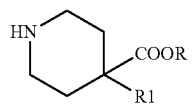
(VIII)

where R may be alkyl, optionally followed by forming the desired addition salt.

13. The process according to claim 12 further comprising the step of preparing the compound of formula (VII) by oxidizing a compound of formula (VI):

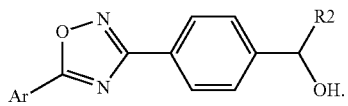
(VI)

14. The process according to claim 11 further comprising:
(a) preparing the compound of formula (VI) wherein R2 is H, by reacting a compound of formula (IX):

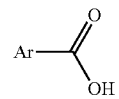
(IX)

with N-hydroxy-4-hydroxymethylbenzamidine, optionally in the presence of one or more of activating and/or coupling agent,
optionally followed by
(b) oxidizing the obtained compound of formula (VI) (wherein R2 is H) followed by its reaction with alkylmagnesiumhalide.

15. The process according to claim 9 further comprising the additional step of isolating the obtained compound.

16. A method for the treatment of a condition selected from the group consisting of transplant rejection, tissue graft rejection, auto-immune diseases, autoimmune uveitis, ischemia, rheumatoid arthritis, asthma, pollinosis, psoriasis, Alzheimer's disease, myocarditis, atopic dermatitis, lymphocytic leukemias, lymphomas, sepsis, multiple sclerosis, lupus erythematosus, inflammatory bowel diseases, diabetes mellitus, glomerulonephritis, atherosclerosis, multiorgan failure, pneumonia, ischemia reperfusion injury, chronic obstructive pulmonary disease, viral inflammation, hepatitis, chronic bronchitis and granulomatous disease, comprising administering a compound according to claim 1 to patient in need of treatment thereof.

17. The combination comprising a compound according to claim 1 with an immunosuppressant selected from the group consisting of adrenocortical steroids, cyclosporine, azathioprine, methotrexate, calcineurin inhibitors, IL-2 receptor blocking antibodies, T-cell and other immune cell depleting antibodies, anti-TNF, mycophenolate, and mTOR inhibitors.

18. A pharmaceutical composition comprising a compound according to claim 1.

* * * * *